United States Patent
Fujihara et al.

(10) Patent No.: US 12,389,911 B2
(45) Date of Patent: Aug. 19, 2025

(54) BENZIMIDAZOLE COMPOUND OR SALT THEREOF, AGRICULTURAL AND HORTICULTURAL INSECTICIDAL AND ACARICIDAL AGENT CONTAINING SAID COMPOUND, AND METHOD FOR USING SAME

(71) Applicant: NIHON NOHYAKU CO., LTD., Tokyo (JP)

(72) Inventors: Hirokazu Fujihara, Kawachinagano (JP); Kazuki Fujii, Kawachinagano (JP); Shunsuke Fuchi, Kawachinagano (JP); Ryosuke Tanaka, Kawachinagano (JP); Kenta Akimoto, Kawachinagano (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 734 days.

(21) Appl. No.: 17/780,853

(22) PCT Filed: Nov. 27, 2020

(86) PCT No.: PCT/JP2020/044267
§ 371 (c)(1),
(2) Date: May 27, 2022

(87) PCT Pub. No.: WO2021/107110
PCT Pub. Date: Jun. 3, 2021

(65) Prior Publication Data
US 2023/0056277 A1 Feb. 23, 2023

(30) Foreign Application Priority Data
Nov. 28, 2019 (JP) .................. 2019-215007

(51) Int. Cl.
*A01N 43/52* (2006.01)
*A01P 7/02* (2006.01)
*A01P 7/04* (2006.01)
*C07D 403/04* (2006.01)

(52) U.S. Cl.
CPC ............... *A01N 43/52* (2013.01); *A01P 7/02* (2021.08); *A01P 7/04* (2021.08); *C07D 403/04* (2013.01)

(58) Field of Classification Search
None
See application file for complete search history.

(56) References Cited

U.S. PATENT DOCUMENTS

| | | | |
|---|---|---|---|
| 4,987,146 A | 1/1991 | Rohde et al. |
| 8,759,345 B2 | 6/2014 | Hocutt et al. |
| 8,853,238 B2 | 10/2014 | Takyo et al. |
| 8,865,713 B2 | 10/2014 | Hocutt et al. |
| 9,018,134 B2 | 4/2015 | Takahashi et al. |
| 9,073,923 B2 | 7/2015 | Hocutt et al. |
| 9,120,823 B2 | 9/2015 | Takahashi et al. |
| 9,278,983 B2 | 3/2016 | Takyo et al. |
| 9,353,110 B2 | 5/2016 | Takahashi et al. |
| 9,403,771 B2 | 8/2016 | Takahashi et al. |
| 10,851,083 B2 | 12/2020 | Hocutt et al. |
| 2011/0046132 A1 | 2/2011 | Hocutt et al. |
| 2014/0005193 A1 | 1/2014 | Hocutt et al. |
| 2014/0018373 A1 | 1/2014 | Takyo et al. |
| 2014/0256722 A1 | 9/2014 | Hocutt et al. |
| 2014/0364444 A1 | 12/2014 | Takyo et al. |
| 2015/0197532 A1 | 7/2015 | Takahashi et al. |
| 2015/0284335 A1 | 10/2015 | Hocutt et al. |
| 2016/0009715 A1 | 1/2016 | Takahashi et al. |
| 2016/0159743 A1 | 6/2016 | Takahashi et al. |

(Continued)

FOREIGN PATENT DOCUMENTS

| | | | |
|---|---|---|---|
| DE | 3824658 A1 | 1/1990 |
| WO | WO 2009/134750 A1 | 11/2009 |

(Continued)

OTHER PUBLICATIONS

International Search Report for PCT/JP2020/044267 mailed on Feb. 2, 2021.

(Continued)

*Primary Examiner* — Adam C Milligan
*Assistant Examiner* — Jason Nolan
(74) *Attorney, Agent, or Firm* — Birch, Stewart, Kolasch & Birch, LLP

(57) ABSTRACT

The present invention provides a benzimidazole compound represented by the general formula (1)

[Formula 1]

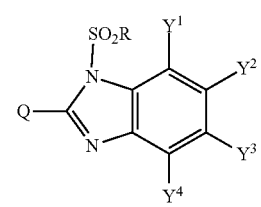

(1)

wherein R is an alkyl group or the like, $Y^1$, $Y^2$, $Y^3$, and $Y^4$ are a hydrogen atom or the like, Q is a 5-membered heterocyclic group optionally having a substituent such as a substituted imidazole bound at a nitrogen atom and a substituted pyrazole bound at a nitrogen atom, or a salt thereof, an agricultural and horticultural insecticidal and acaricidal agent having the compound or a salt thereof as an active ingredient, and a method for using the same.

9 Claims, No Drawings

(56) References Cited

U.S. PATENT DOCUMENTS

| | | |
|---|---|---|
| 2016/0168127 A1 | 6/2016 | Hocutt et al. |
| 2018/0022733 A1 | 1/2018 | Hocutt et al. |
| 2018/0215732 A9 | 8/2018 | Hocutt et al. |
| 2019/0367486 A1 | 12/2019 | Hocutt et al. |
| 2021/0078978 A1 | 3/2021 | Hocutt et al. |

FOREIGN PATENT DOCUMENTS

| | | |
|---|---|---|
| WO | WO 2012/086848 A1 | 6/2012 |
| WO | WO 2013/018928 A1 | 2/2013 |

OTHER PUBLICATIONS

Written Opinion of the International Searching Authority for PCT/JP2020/044267 mailed on Feb. 2, 2021.

Extended European Search Report for European Application No. 20891807.8, dated Oct. 12, 2023.

BENZIMIDAZOLE COMPOUND OR SALT THEREOF, AGRICULTURAL AND HORTICULTURAL INSECTICIDAL AND ACARICIDAL AGENT CONTAINING SAID COMPOUND, AND METHOD FOR USING SAME

TECHNICAL FIELD

The present invention relates to an agricultural and horticultural insecticidal and acaricidal agent containing a benzimidazole compound or a salt thereof as an active ingredient and a method for using the same.

BACKGROUND ART

Certain kinds of benzimidazole compounds have been documented as useful as insecticidal agents, medicines, and the like (e.g., see Patent Literatures 1 to 4). These literatures do not include any description about a benzimidazole compound wherein a sulfonyl group such as an alkylsulfonyl group is present at the 1-position nitrogen atom and a nitrogen atom of a nitrogen-containing heterocycle binds at position 2, and about an insecticidal effect thereof.

CITATION LIST

Patent Literature

Patent Literature 1: International Publication No. WO 2012/086848
Patent Literature 2: International Publication No. WO 2013/018928
Patent Literature 3: International Publication No. WO 2009/134750
Patent Literature 4: Publication No. DE3824658

SUMMARY OF INVENTION

Technical Problem

In crop production in the fields of agriculture, horticulture and the like, damages caused by pests and the like have been still serious, and there is a demand for developing an agricultural and horticultural insecticidal and acaricidal agent having a novel action, less impact on natural enemy useful insects, and imparted with penetration and translocation activity, from the viewpoints of emergence of resistant pests against existing drugs, impacts on environmental biology and labor saving of operation.

Solution to Problem

The present inventors conducted extensive studies to solve the above problem and found that a benzimidazole compound represented by general formula (1) wherein a nitrogen atom of a nitrogen-containing heterocyclic group binds at position 2 and a specific sulfonyl group is present at position 1 or a salt thereof demonstrates not only a good controlling effect on agricultural and horticultural pests but can solve the above problem, whereby the present invention has been accomplished.

More specifically, the present invention relates to [1] a benzimidazole compound represented by a general formula (1)

[Formula 1]

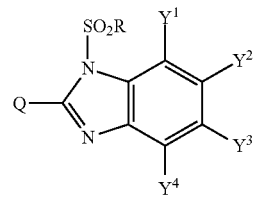

(1)

wherein R is
(a1) a $(C_1-C_6)$ alkyl group;
(a2) a $(C_3-C_6)$ cycloalkyl group;
(a3) a $(C_3-C_6)$ cycloalkyl $(C_1-C_6)$ alkyl group;
(a4) a halo $(C_1-C_6)$ alkyl group;
(a5) a $(C_2-C_6)$ alkenyl group; or
(a6) a $(C_2-C_6)$ alkynyl group,
$Y^1$, $Y^2$, $Y^3$ and $Y^4$, the same or different, are
(b1) a hydrogen atom;
(b2) a halogen atom;
(b3) a $(C_1-C_6)$ alkyl group; or
(b4) a halo $(C_1-C_6)$ alkyl group,
Q is selected from the following nitrogen-containing 5-membered heterocyclic groups,

[Formula 2]

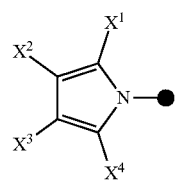

Q-1

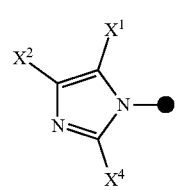

Q-2

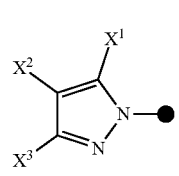

Q-3

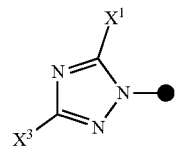

Q-4

-continued

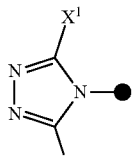
Q-5

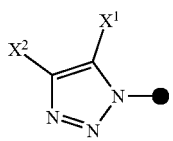
Q-6

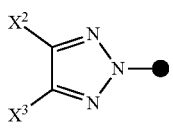
Q-7

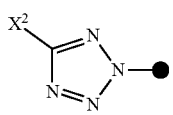
Q-8

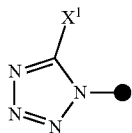
Q-9 wherein $X^1$ and $X^4$, the same or different, are
- (c1) a hydrogen atom; or
- (c2) a ($C_1$-$C_6$) alkyl group, $X^2$ is
- (d1) a hydrogen atom;
- (d2) a halogen atom;
- (d3) a cyano group;
- (d4) a ($C_1$-$C_{12}$) alkyl group;
- (d5) a ($C_3$-$C_6$) cycloalkyl group;
- (d6) a ($C_2$-$C_{12}$) alkenyl group;
- (d7) a ($C_2$-$C_{12}$) alkynyl group;
- (d8) a ($C_1$-$C_6$) alkoxy group;
- (d9) a halo ($C_1$-$C_6$) alkyl group;
- (d10) a halo ($C_1$-$C_6$) alkoxy group;
- (d11) a ($C_1$-$C_6$) alkylthio group;
- (d12) a ($C_1$-$C_6$) alkylsulfinyl group;
- (d13) a ($C_1$-$C_6$) alkylsulfonyl group;
- (d14) a halo ($C_1$-$C_6$) alkylthio group;
- (d15) a halo ($C_1$-$C_6$) alkylsulfinyl group;
- (d16) a halo ($C_1$-$C_6$) alkylsulfonyl group;
- (d17) a halo ($C_1$-$C_6$) alkoxy ($C_1$-$C_6$) alkyl group;
- (d18) a ($C_3$-$C_6$) cycloalkyl ($C_2$-$C_6$) alkynyl group;
- (d19) a ($C_1$-$C_6$) alkylcarbonyl group;
- (d20) a ($C_1$-$C_6$) alkoxycarbonyl group;
- (d21) a ($C_2$-$C_6$) alkynyloxycarbonyl group;
- (d22) a ($C_1$-$C_6$) alkylthiocarbonyl group;
- (d23) a ($C_1$-$C_6$) alkoxycarbonyl ($C_1$-$C_6$) alkyl group;
- (d24) a ($C_1$-$C_6$) alkoxycarbonyl ($C_2$-$C_6$) alkenyl group;
- (d25) an aryloxy ($C_1$-$C_6$) alkyl group;
- (d26) an aryloxy ($C_1$-$C_6$) alkyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;
- (d27) an aryloxycarbonyl group;
- (d28) an aryloxycarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;
- (d29) an arylcarbonyl group;
- (d30) an arylcarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;
- (d31) an aryl ($C_1$-$C_6$) alkyl group;
- (d32) an aryl ($C_1$-$C_6$) alkyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;
- (d33) an aryl ($C_1$-$C_6$) alkoxycarbonyl group;
- (d34) an aryl ($C_1$-$C_6$) alkoxycarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;
- (d35) an aryl ($C_2$-$C_6$) alkynyl group;
- (d36) an aryl ($C_2$-$C_6$) alkynyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;
- (d37) a $R^1R^2N$ group, wherein $R^1$ and $R^2$, the same or different, are (aa) a hydrogen atom, (ab) a ($C_1$-$C_6$) alkyl group, (ac) a ($C_1$-$C_6$) alkoxy group, (ad) a ($C_1$-$C_6$) alkoxycarbonyl group, (ae) a ($C_1$-$C_6$) alkylsulfonyl group, (af) a halo ($C_1$-$C_6$) alkylsulfonyl group, (ag) an aryl group, (ah) a ($C_3$-$C_6$) cycloalkyl group, (ai) a halo ($C_1$-$C_6$) alkyl group, or (aj) an aryl ($C_1$-$C_6$) alkyl group);
- (d38) a $R^1R^2N$ carbonyl group, wherein $R^1$ and $R^2$ have the same meaning as above;
- (d39) a $R^1R^2N$ sulfonyl group, wherein $R^1$ and $R^2$ have the same meaning as above;
- (d40) a halo ($C_1$-$C_6$) alkoxycarbonyl group;
- (d41) a halo ($C_1$-$C_6$) alkoxycarbonyl ($C_2$-$C_6$) alkenyl group;
- (d42) an aryl ($C_1$-$C_6$) alkoxycarbonyl ($C_2$-$C_6$) alkenyl group;

(d43) an aryl ($C_1$-$C_6$) alkoxycarbonyl ($C_2$-$C_6$) alkenyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(d44) a ($C_3$-$C_{12}$) cycloalkyl ($C_1$-$C_6$) alkoxycarbonyl ($C_2$-$C_6$) alkenyl group;

(d45) a heteroaryl ($C_2$-$C_6$) alkynyl group;

(d46) a heteroaryl ($C_2$-$C_6$) alkynyl group having the same or different one to four substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(d47) a ($C_3$-$C_6$) cycloalkyl ($C_1$-$C_6$) alkyl group;

(d48) a ($C_1$-$C_6$) alkoxy ($C_2$-$C_6$) alkynyl group;

(d49) a ($C_1$-$C_6$) alkoxy ($C_1$-$C_6$) alkyl group;

(d50) a ($C_1$-$C_6$) alkylcarbonyloxy ($C_2$-$C_6$) alkynyl group;

(d51) a ($C_1$-$C_6$) alkylcarbonyloxy ($C_1$-$C_6$) alkyl group;

(d52) a halo ($C_1$-$C_6$) alkoxy ($C_2$-$C_6$) alkynyl group;

(d53) an aryloxy ($C_2$-$C_6$) alkynyl group;

(d54) an aryloxy ($C_2$-$C_6$) alkynyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(d55) a 1-($C_1$-$C_6$) alkoxyimino ($C_1$-$C_6$) alkyl group;

(d56) a ($C_1$-$C_6$) alkylaminocarbonyl ($C_2$-$C_6$) alkenyl group;

(d57) a halo ($C_1$-$C_6$) alkylaminocarbonyl ($C_2$-$C_6$) alkenyl group;

(d58) an aryl ($C_1$-$C_6$) alkylthio group; or (d59) an aryl ($C_1$-$C_6$) alkylthio group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group, $X^3$ is (e1) a hydrogen atom;

(e2) a halogen atom;

(e3) a ($C_1$-$C_6$) alkyl group;

(e4) a halo ($C_1$-$C_6$) alkyl group;

(e5) a ($C_1$-$C_6$) alkoxy group;

(e6) a halo ($C_1$-$C_6$) alkoxy group;

(e7) a ($C_1$-$C_6$) alkoxycarbonyl ($C_2$-$C_6$) alkenyl group;

(e8) a ($C_1$-$C_6$) alkylthio group;

(e9) a ($C_1$-$C_6$) alkoxycarbonyl ($C_1$-$C_6$) alkoxy group;

(e10) a ($C_1$-$C_6$) alkoxycarbonyl group;

(e11) a ($C_2$-$C_6$) alkynyloxycarbonyl group;

(e12) an aryl ($C_1$-$C_6$) alkyl group;

(e13) an aryl ($C_1$-$C_6$) alkyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e14) an arylsulfonyl group;

(e15) an arylsulfonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e16) an aryloxycarbonyl group;

(e17) an aryloxycarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e18) an aryl ($C_1$-$C_6$) alkoxycarbonyl group;

(e19) an aryl ($C_1$-$C_6$) alkoxycarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e20) an aryl ($C_1$-$C_6$) alkoxy group;

(e21) an aryl ($C_1$-$C_6$) alkoxy group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e22) a ($C_3$-$C_6$) cycloalkyl group;

(e23) a ($C_3$-$C_6$) cycloalkyl ($C_2$-$C_6$) alkenyl group;

(e24) a ($C_3$-$C_6$) cycloalkyl ($C_1$-$C_6$) alkyl group;

(e25) a ($C_2$-$C_6$) alkenyl group;

(e26) an aryl ($C_2$-$C_6$) alkynyl group;

(e27) an aryl ($C_2$-$C_6$) alkynyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e28) a ($C_1$-$C_6$) alkoxy ($C_1$-$C_6$) alkyl group;

(e29) a ($C_2$-$C_6$) alkynyloxy group;

(e30) a cyano group;

(e31) a ($C_2$-$C_6$) alkynyl group;

(e32) a ($C_1$-$C_6$) alkoxycarbonyl ($C_1$-$C_6$) alkyl group;

(e33) a ($C_1$-$C_6$) alkoxy ($C_2$-$C_6$) alkynyl group;

(e34) a halo ($C_1$-$C_6$) alkoxy ($C_2$-$C_6$) alkynyl group;

(e35) a $R^1R^2N$ carbonyl group, wherein $R^1$ and $R^2$ have the same meaning as above;

(e36) a $R^1R^2N$ carbonyl $(C_1-C_6)$ alkoxy group, wherein $R^1$ and $R^2$ have the same meaning as above;
(e37) a $R^1R^2N$ carbonyl halo $(C_1-C_6)$ alkoxy group, wherein $R^1$ and $R^2$ have the same meaning as above, or $X^2$ and $X^3$ may be combined to form a 5- to 8-membered aliphatic ring together with the carbon atoms to which they are bound, and the aliphatic ring may have one to five substituents selected from a $(C_1-C_6)$ alkyl group and an oxo group, wherein the moiety at which the • mark is shown binds to benzimidazole;

or a salt thereof,

[2]

the benzimidazole compound according to [1], wherein R is (a1) a $(C_1-C_6)$ alkyl group; or
(a4) a halo $(C_1-C_6)$ alkyl group, $Y^1$, $Y^2$, $Y^3$ and $Y^4$, the same or different, are (b1) a hydrogen atom;
(b2) a halogen atom;
(b3) a $(C_1-C_6)$ alkyl group; or
(b4) a halo $(C_1-C_6)$ alkyl group, $X^1$ and $X^4$, the same or different, are (c1) a hydrogen atom; or
(c2) a $(C_1-C_6)$ alkyl group, $X^2$ is (d1) a hydrogen atom;
(d2) a halogen atom;
(d3) a cyano group;
(d4) a $(C_1-C_{12})$ alkyl group;
(d5) a $(C_3-C_6)$ cycloalkyl group;
(d6) a $(C_2-C_{12})$ alkenyl group;
(d7) a $(C_2-C_{12})$ alkynyl group;
(d9) a halo $(C_1-C_6)$ alkyl group;
(d11) a $(C_1-C_6)$ alkylthio group;
(d12) a $(C_1-C_6)$ alkylsulfinyl group;
(d13) a $(C_1-C_6)$ alkylsulfonyl group;
(d14) a halo $(C_1-C_6)$ alkylthio group;
(d17) a halo $(C_1-C_6)$ alkoxy $(C_1-C_6)$ alkyl group;
(d18) a $(C_3-C_6)$ cycloalkyl $(C_2-C_6)$ alkynyl group;
(d19) a $(C_1-C_6)$ alkylcarbonyl group;
(d20) a $(C_1-C_6)$ alkoxycarbonyl group;
(d21) a $(C_2-C_6)$ alkynyloxycarbonyl group;
(d22) a $(C_1-C_6)$ alkylthiocarbonyl group;
(d23) a $(C_1-C_6)$ alkoxycarbonyl $(C_1-C_6)$ alkyl group;
(d24) a $(C_1-C_6)$ alkoxycarbonyl $(C_2-C_6)$ alkenyl group;
(d25) an aryloxy $(C_1-C_6)$ alkyl group;
(d26) an aryloxy $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d27) an aryloxycarbonyl group;
(d28) an aryloxycarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d29) an arylcarbonyl group;
(d30) an arylcarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d31) an aryl $(C_1-C_6)$ alkyl group;
(d32) an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d35) an aryl $(C_2-C_6)$ alkynyl group;
(d36) an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d38) a $R^1R^2N$ carbonyl group, wherein $R^1$ and $R^2$ have the same meaning as above;
(d39) a $R^1R^2N$ sulfonyl group, wherein $R^1$ and $R^2$ have the same meaning as above;
(d40) a halo $(C_1-C_6)$ alkoxycarbonyl group;
(d41) a halo $(C_1-C_6)$ alkoxycarbonyl $(C_2-C_6)$ alkenyl group;
(d42) an aryl $(C_1-C_6)$ alkoxycarbonyl $(C_2-C_6)$ alkenyl group;
(d43) an aryl $(C_1-C_6)$ alkoxycarbonyl $(C_2-C_6)$ alkenyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d44) a $(C_3-C_{12})$ cycloalkyl $(C_1-C_6)$ alkoxycarbonyl $(C_2-C_6)$ alkenyl group;
(d45) a heteroaryl $(C_2-C_6)$ alkynyl group;
(d46) a heteroaryl $(C_2-C_6)$ alkynyl group having the same or different one to four substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d47) a $(C_3-C_6)$ cycloalkyl $(C_1-C_6)$ alkyl group;
(d48) a $(C_1-C_6)$ alkoxy $(C_2-C_6)$ alkynyl group;
(d49) a $(C_1-C_6)$ alkoxy $(C_1-C_6)$ alkyl group;
(d50) a $(C_1-C_6)$ alkylcarbonyloxy $(C_2-C_6)$ alkynyl group;
(d51) a $(C_1-C_6)$ alkylcarbonyloxy $(C_1-C_6)$ alkyl group;
(d52) a halo $(C_1-C_6)$ alkoxy $(C_2-C_6)$ alkynyl group;
(d53) an aryloxy $(C_2-C_6)$ alkynyl group;
(d54) an aryloxy $(C_2-C_6)$ alkynyl group having the same or different one to five substituents selected from (a) a halogen atom, (b) a $(C_1-C_6)$ alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(d56) a ($C_1$-$C_6$) alkylaminocarbonyl ($C_2$-$C_6$) alkenyl group;

(d57) a halo ($C_1$-$C_6$) alkylaminocarbonyl ($C_2$-$C_6$) alkenyl group;

(d58) an aryl ($C_1$-$C_6$) alkylthio group; or (d59) an aryl ($C_1$-$C_6$) alkylthio group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group, $X^3$ is (e1) a hydrogen atom;

(e2) a halogen atom;

(e3) a ($C_1$-$C_6$) alkyl group;

(e4) a halo ($C_1$-$C_6$) alkyl group;

(e5) a ($C_1$-$C_6$) alkoxy group;

(e6) a halo ($C_1$-$C_6$) alkoxy group;

(e7) a ($C_1$-$C_6$) alkoxycarbonyl ($C_2$-$C_6$) alkenyl group;

(e8) a ($C_1$-$C_6$) alkylthio group;

(e9) a ($C_1$-$C_6$) alkoxycarbonyl ($C_1$-$C_6$) alkoxy group;

(e10) a ($C_1$-$C_6$) alkoxycarbonyl group;

(e12) an aryl ($C_1$-$C_6$) alkyl group;

(e13) an aryl ($C_1$-$C_6$) alkyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e14) an arylsulfonyl group;

(e15) an arylsulfonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e20) an aryl ($C_1$-$C_6$) alkoxy group;

(e21) an aryl ($C_1$-$C_6$) alkoxy group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e22) a ($C_3$-$C_6$) cycloalkyl group;

(e23) a ($C_3$-$C_6$) cycloalkyl ($C_2$-$C_6$) alkenyl group;

(e24) a ($C_3$-$C_6$) cycloalkyl ($C_1$-$C_6$) alkyl group;

(e25) a ($C_2$-$C_6$) alkenyl group;

(e26) an aryl ($C_2$-$C_6$) alkynyl group;

(e27) an aryl ($C_2$-$C_6$) alkynyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

(e28) a ($C_1$-$C_6$) alkoxy ($C_1$-$C_6$) alkyl group;

(e29) a ($C_2$-$C_6$) alkynyloxy group;

(e30) a cyano group;

(e31) a ($C_2$-$C_6$) alkynyl group;

(e32) a ($C_1$-$C_6$) alkoxycarbonyl ($C_1$-$C_6$) alkyl group;

(e33) a ($C_1$-$C_6$) alkoxy ($C_2$-$C_6$) alkynyl group;

(e34) a halo ($C_1$-$C_6$) alkoxy ($C_2$-$C_6$) alkynyl group;

(e35) a $R^1R^2N$ carbonyl group, wherein $R^1$ and $R^2$ have the same meaning as above;

(e36) a $R^1R^2N$ carbonyl ($C_1$-$C_6$) alkoxy group, wherein $R^1$ and $R^2$ have the same meaning as above;

(e37) a $R^1R^2N$ carbonylhalo ($C_1$-$C_6$) alkoxy group, wherein $R^1$ and $R^2$ have the same meaning as above; or $X^2$ and $X^3$ may be combined to form a 5- to 8-membered aliphatic ring together with the carbon atoms to which they are bound, and the aliphatic ring may have one to five substituents selected from a ($C_1$-$C_6$) alkyl group and an oxo group; or a salt thereof,

[3] the benzimidazole compound or a salt thereof according to [1] or [2], wherein Q is Q-2, Q-3, or Q-4,

[4] an agricultural and horticultural insecticidal and acaricidal agent, comprising the benzimidazole compound or a salt thereof according to any of [1] to [3] as an active ingredient,

[5] a method for using an agricultural and horticultural insecticidal and acaricidal agent, comprising applying an effective amount of the benzimidazole compound or a salt thereof according to any of [1] to [3] to plants or soil;

[6] an ectoparasite control agent for animals, comprising the benzimidazole compound or a salt thereof according to any of [1] to [3] as an active ingredient;

[7] an endoparasite control agent for animals, comprising the benzimidazole compound or a salt thereof according to any of [1] to [3] as an active ingredient.

Advantageous Effects of Invention

The benzimidazole compound wherein a nitrogen atom of a nitrogen-containing heterocyclic group binds at position 2 and a specific sulfonyl group is present at position 1 of the present invention or a salt thereof has not only a good effect as an agricultural and horticultural insecticidal and acaricidal agent but also has an effect on pests parasitic in companion animals such as dogs and cats or domestic animals such as cows and sheep.

DESCRIPTION OF EMBODIMENTS

In the definition of the general formula (1) representing the benzimidazole compound wherein a nitrogen atom of a nitrogen-containing heterocyclic group binds at position 2 and a specific sulfonyl group is present at position 1 of the present invention or a salt thereof, the term "halo" means "a halogen atom" and refers to a fluorine atom, a chlorine atom, a bromine atom, or an iodine atom.

The term "($C_1$-$C_6$) alkyl group" refers to linear or branched alkyl groups having 1 to 6 carbon atoms such as a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 2,3-dimethylpropyl group, a 1-ethylpropyl group, a 1-methylbutyl group, a 2-methylbutyl group, a normal hexyl group, an isohexyl group, a 2-hexyl group, a 3-hexyl group, a 2-methylpentyl group, a 3-methylpentyl group, a 1,1,2-trimethylpropyl group, and a 3,3-dimethylbutyl group, the term "$(C_2$-$C_6)$ alkenyl group" refers to linear or branched alkenyl groups having 2 to 6 carbon atoms such as a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, and a 3,3-dimethyl-1-butenyl group, and the term "$(C_2$-$C_6)$ alkynyl group" refers to linear or branched alkynyl groups having 2 to 6 carbon atoms such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, and a 3,3-dimethyl-1-butynyl group.

The term "$(C_1$-$C_{12})$ alkyl group" refers to linear or branched alkyl groups having 1 to 12 carbon atoms such as a methyl group, an ethyl group, a normal propyl group, an isopropyl group, a normal butyl group, an isobutyl group, a secondary butyl group, a tertiary butyl group, a normal pentyl group, an isopentyl group, a tertiary pentyl group, a neopentyl group, a 2,3-dimethylpropyl group, a 1-ethylpropyl group, a 1-methylbutyl group, a normal hexyl group, an isohexyl group, a 1,1,2-trimethylpropyl group, a heptyl group, an octyl group, a nonyl group, a decyl group, an undecyl group, and a dodecyl group, the term "$(C_2$-$C_{12})$ alkenyl group" refers to linear or branched alkenyl groups having 2 to 12 carbon atoms such as s vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a heptenyl group, an octenyl group, a nonenyl group, a decenyl group, an undecenyl group, and a dodecenyl group, and the term "$(C_2$-$C_{12})$ alkynyl group" refers to linear or branched alkynyl groups having 2 to 12 carbon atoms such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a heptynyl group, an octynyl group, a nonynyl group, a decynyl group, an undesynyl group, and a dodecynyl group.

The term "$(C_3$-$C_6)$ cycloalkyl group" refers to cyclic alkyl groups having 3 to 6 carbon atoms such as a cyclopropyl group, a cyclobutyl group, a cyclopentyl group, and a cyclohexyl group, and the term "$(C_1$-$C_6)$ alkoxy group" refers to linear or branched alkoxy groups having 1 to 6 carbon atoms such as a methoxy group, an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group, an isohexyloxy group, and a 1,1,2-trimethylpropyloxy group.

The term "$(C_3$-$C_{12})$ cycloalkyl group" refers to cyclic alkyl groups having 3 to 12 carbon atoms such as a cyclopropyl group, a cyclobutyl group, a cyclopentyl group, a cyclohexyl group, a cycloheptyl group, a cyclooctyl group, a cyclononyl group, and a cyclodecyl group, and bridged cyclic alkyl groups such as a norbornyl group, and an adamantyl group.

The term "$(C_1$-$C_6)$ alkylthio group" refers to linear or branched alkylthio groups having 1 to 6 carbon atoms such as a methylthio group, an ethylthio group, a normal propylthio group, an isopropylthio group, a normal butylthio group, a secondary butylthio group, a tertiary butylthio group, a normal pentylthio group, an isopentylthio group, a tertiary pentylthio group, a neopentylthio group, a 2,3-dimethylpropylthio group, a 1-ethylpropylthio group, a 1-methylbutylthio group, a normal hexylthio group, an isohexylthio group, and a 1,1,2-trimethylpropylthio group, the term "$(C_1$-$C_6)$ alkylsulfinyl group" refers to linear or branched alkylsulfinyl groups having 1 to 6 carbon atoms such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, an isopentylsulfinyl group, a tertiary pentylsulfinyl group, a neopentylsulfinyl group, a 2,3-dimethylpropylsulfinyl group, a 1-ethylpropylsulfinyl group, a 1-methylbutylsulfinyl group, a normal hexylsulfinyl group, an isohexylsulfinyl group, and a 1,1,2-trimethylpropylsulfinyl group, and the term "$(C_1$-$C_6)$ alkylsulfonyl group" refers to linear or branched alkylsulfonyl groups having 1 to 6 carbon atoms such as a methylsulfonyl group, an ethylsulfonyl group, a normal propylsulfonyl group, an isopropylsulfonyl group, a normal butylsulfonyl group, a secondary butylsulfonyl group, a tertiary butylsulfonyl group, a normal pentylsulfonyl group, an isopentylsulfonyl group, a tertiary pentylsulfonyl group, a neopentylsulfonyl group, a 2,3-dimethylpropylsulfonyl group, a 1-ethylpropylsulfonyl group, a 1-methylbutylsulfonyl group, a normal hexylsulfonyl group, an isohexylsulfonyl group, and a 1,1,2-trimethylpropylsulfonyl group.

The above "$(C_1$-$C_6)$ alkyl group", "$(C_2$-$C_6)$ alkenyl group", "$(C_2$-$C_6)$ alkynyl group", "$(C_3$-$C_6)$ cycloalkyl group", "$(C_1$-$C_6)$ alkoxy group", "$(C_1$-$C_6)$ alkylthio group", "$(C_1$-$C_6)$ alkylsulfinyl group", or "$(C_1$-$C_6)$ alkylsulfonyl group" may be substituted with one or more halogen atoms at a substitutable position, and when the number of halogen atoms to be used for substitution is two or more, these halogen atoms may be the same or different. Each of the groups substituted with one or more halogens is termed as "halo $(C_1$-$C_6)$ alkyl group", "halo $(C_2$-$C_6)$ alkenyl group", "halo $(C_2$-$C_6)$ alkynyl group", "halo $(C_3$-$C_6)$ cycloalkyl group", "halo $(C_1$-$C_6)$ alkoxy group", "halo $(C_1$-$C_6)$ alkylthio group", "halo $(C_1$-$C_6)$ alkylsulfinyl group", or "halo $(C_1$-$C_6)$ alkylsulfonyl group".

The expressions "$(C_1$-$C_6)$", "$(C_2$-$C_6)$", "$(C_3$-$C_6)$", "$(C_1$-$C_{12})$" and the like refer to ranges of the number of carbon atoms of various substituents. The above definition is also applicable to a group to which the above substituent is linked and, for example, "a $(C_3$-$C_6)$ cycloalkyl $(C_1$-$C_6)$ alkyl group" refers to a linear or branched cycloalkyl group having 3 to 6 carbon atoms binding to a linear or branched alkyl group having 1 to 6 carbon atoms.

The term "aryl group" refers to aromatic hydrocarbon groups having 6 to 10 carbon atoms such as a phenyl group, a 1-naphthyl group, and a 2-naphthyl group.

The term "heteroaryl group" refers to 5- to 6-membered aromatic heterocyclic groups having 1 to 4 heteroatoms selected from nitrogen atom, oxygen atom, and sulfur atom (the sulfur atom may be oxidized) such as fryl, thienyl, pyridyl, pyrimidinyl, pyridazinyl, pyrazinyl, pyrrolyl, imidazolyl, pyrazolyl, triazolyl, isothiazolyl, oxazolyl, isoxazolyl, oxadiazolyl, thiadiazolyl, triazolyl, tetrazolyl, and triazinyl.

The term "5- to 8-membered aliphatic ring" refers to cycloalkenes having 5 to 8 carbon atoms such as cyclopentene, cyclohexene, cycloheptene, and cyclooctene.

The term "$(C_1-C_6)$ alkylcarbonyl group" refers to alkylcarbonyl groups constituted by a linear or branched alkyl group having 1 to 6 carbon atoms and a carbonyl group such as an acetyl group, a propionyl group, a butyryl group, an isobutyryl group, a normal butylcarbonyl group, an isobutylcarbonyl group, a secondary butylcarbonyl group, a tertiary butylcarbonyl group, a normal pentylcarbonyl group, an isopentylcarbonyl group, a tertiary pentylcarbonyl group, a neopentylcarbonyl group, a 2,3-dimethylpropylcarbonyl group, a 1-ethylpropylcarbonyl group, a 1-methylbutylcarbonyl group, a 2-methylbutylcarbonyl group, a normal hexylcarbonyl group, an isohexylcarbonyl group, a 2-hexylcarbonyl group, a 3-hexylcarbonyl group, a 2-methylpentylcarbonyl group, a 3-methylpentylcarbonyl group, a 1,1,2-trimethylpropylcarbonyl group, a 3,3-dimethylbutylcarbonyl group.

The term "$(C_1-C_6)$ alkoxycarbonyl group" refers to alkoxycarbonyl groups constituted by a linear or branched alkoxy group having 1 to 6 carbon atoms and a carbonyl group such as a methoxycarbonyl group, an ethoxycarbonyl group, a normal propoxycarbonyl group, an isopropoxycarbonyl group, a normal butoxycarbonyl group, a secondary butoxycarbonyl group, a tertiary butoxycarbonyl group, a normal pentyloxycarbonyl group, an isopentyloxycarbonyl group, a tertiary pentyloxycarbonyl group, a neopentyloxycarbonyl group, a 2,3-dimethylpropyloxycarbonyl group, a 1-ethylpropyloxycarbonyl group, a 1-methylbutyloxycarbonyl group, a normal hexyloxycarbonyl group, an isohexyloxycarbonyl group, and a 1,1,2-trimethylpropyloxycarbonyl group.

Examples of the salt of the benzimidazole compound represented by the general formula (1) of the present invention include inorganic acid salts such as hydrochlorides, sulfates, nitrates, and phosphates, organic acid salts such as acetates, fumarates, maleates, oxalates, methanesulfonates, benzenesulfonates, and p-toluenesulfonates, and salts with an inorganic or organic base such as a sodium ion, a potassium ion, a calcium ion, and a trimethylammonium.

In the benzimidazole compound represented by the general formula (1) and a salt thereof of the present invention, there are cases where one or more asymmetric centers are present in the structural formula thereof, and there are also cases where two or more optical isomers and diastereomers are present. The present invention encompasses various optical isomers and mixtures containing them in any ratio. In the benzimidazole compound represented by the general formula (1) and a salt thereof of the present invention, there are cases where two types of geometrical isomers derived from a carbon-carbon double bond are present in the structural formula thereof, but the present invention encompasses all various geometrical isomers and mixtures containing them in any ratio.

In the benzimidazole compound represented by the general formula (1) or a salt thereof of the present invention, R is preferably (a1) a $(C_1-C_6)$ alkyl group; or (a4) a halo $(C_1-C_6)$ alkyl group.

$Y^1$, $Y^2$, $Y^3$ and $Y^4$, the same or different, are preferably (b1) a hydrogen atom; (b2) a halogen atom; (b3) a $(C_1-C_6)$ alkyl group; or (b4) a halo $(C_1-C_6)$ alkyl group.

$X^1$ and $X^4$, the same or different, are preferably (c1) a hydrogen atom; or (c2) a $(C_1-C_6)$ alkyl group.

$X^2$ is preferably
(d1) a hydrogen atom;
(d2) a halogen atom;
(d3) a cyano group;
(d4) a $(C_1-C_{12})$ alkyl group;
(d5) a $(C_3-C_6)$ cycloalkyl group;
(d6) a $(C_2-C_{12})$ alkenyl group;
(d7) a $(C_2-C_{12})$ alkynyl group;
(d9) a halo $(C_1-C_6)$ alkyl group;
(d11) a $(C_1-C_6)$ alkylthio group;
(d12) a $(C_1-C_6)$ alkylsulfinyl group;
(d13) a $(C_1-C_6)$ alkylsulfonyl group;
(d14) a halo $(C_1-C_6)$ alkylthio group;
(d17) a halo $(C_1-C_6)$ alkoxy $(C_1-C_6)$ alkyl group;
(d18) a $(C_3-C_6)$ cycloalkyl $(C_2-C_6)$ alkynyl group;
(d19) a $(C_1-C_6)$ alkylcarbonyl group;
(d20) a $(C_1-C_6)$ alkoxycarbonyl group;
(d21) a $(C_2-C_6)$ alkynyloxycarbonyl group;
(d22) a $(C_1-C_6)$ alkylthiocarbonyl group;
(d23) a $(C_1-C_6)$ alkoxycarbonyl $(C_1-C_6)$ alkyl group;
(d24) a $(C_1-C_6)$ alkoxycarbonyl $(C_2-C_6)$ alkenyl group;
(d25) an aryloxy $(C_1-C_6)$ alkyl group;
(d26) an aryloxy $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d27) an aryloxycarbonyl group;
(d28) an aryloxycarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d29) an arylcarbonyl group;
(d30) an arylcarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d31) an aryl $(C_1-C_6)$ alkyl group;
(d32) an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d35) an aryl $(C_2-C_6)$ alkynyl group;
(d36) an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
(d38) a $R^1R^2N$ carbonyl group, wherein $R^1$ and $R^2$ have the same meaning as above;
(d39) a $R^1R^2N$ sulfonyl group, wherein $R^1$ and $R^2$ have the same meaning as above;

(d40) a halo $(C_1-C_6)$ alkoxycarbonyl group;

(d41) a halo $(C_1-C_6)$ alkoxycarbonyl $(C_2-C_6)$ alkenyl group;

(d42) an aryl $(C_1-C_6)$ alkoxycarbonyl $(C_2-C_6)$ alkenyl group;

(d43) an aryl $(C_1-C_6)$ alkoxycarbonyl $(C_2-C_6)$ alkenyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(d44) a $(C_3-C_{12})$ cycloalkyl $(C_1-C_6)$ alkoxycarbonyl $(C_2-C_6)$ alkenyl group;

(d45) a heteroaryl $(C_2-C_6)$ alkynyl group;

(d46) a heteroaryl $(C_2-C_6)$ alkynyl group having the same or different one to four substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(d47) a $(C_3-C_6)$ cycloalkyl $(C_1-C_6)$ alkyl group;

(d48) a $(C_1-C_6)$ alkoxy $(C_2-C_6)$ alkynyl group;

(d49) a $(C_1-C_6)$ alkoxy $(C_1-C_6)$ alkyl group;

(d50) a $(C_1-C_6)$ alkylcarbonyloxy $(C_2-C_6)$ alkynyl group;

(d51) a $(C_1-C_6)$ alkylcarbonyloxy $(C_1-C_6)$ alkyl group;

(d52) a halo $(C_1-C_6)$ alkoxy $(C_2-C_6)$ alkynyl group;

(d53) an aryloxy $(C_2-C_6)$ alkynyl group;

(d54) an aryloxy $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(d56) a $(C_1-C_6)$ alkylaminocarbonyl $(C_2-C_6)$ alkenyl group;

(d57) a halo $(C_1-C_6)$ alkylaminocarbonyl $(C_2-C_6)$ alkenyl group;

(d58) an aryl $(C_1-C_6)$ alkylthio group; or (d59) an aryl $(C_1-C_6)$ alkylthio group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group.

$X^3$ is preferably (e1) a hydrogen atom;

(e2) a halogen atom;

(e3) a $(C_1-C_6)$ alkyl group;

(e4) a halo $(C_1-C_6)$ alkyl group;

(e5) a $(C_1-C_6)$ alkoxy group;

(e6) a halo $(C_1-C_6)$ alkoxy group;

(e7) a $(C_1-C_6)$ alkoxycarbonyl $(C_2-C_6)$ alkenyl group;

(e8) a $(C_1-C_6)$ alkylthio group;

(e9) a $(C_1-C_6)$ alkoxycarbonyl $(C_1-C_6)$ alkoxy group;

(e10) a $(C_1-C_6)$ alkoxycarbonyl group;

(e12) an aryl $(C_1-C_6)$ alkyl group;

(e13) an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(e14) an arylsulfonyl group;

(e15) an arylsulfonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(e20) an aryl $(C_1-C_6)$ alkoxy group;

(e21) an aryl $(C_1-C_6)$ alkoxy group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(e22) a $(C_3-C_6)$ cycloalkyl group;

(e23) a $(C_3-C_6)$ cycloalkyl $(C_2-C_6)$ alkenyl group;

(e24) a $(C_3-C_6)$ cycloalkyl $(C_1-C_6)$ alkyl group;

(e25) a $(C_2-C_6)$ alkenyl group;

(e26) an aryl $(C_2-C_6)$ alkynyl group;

(e27) an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(e28) a $(C_1-C_6)$ alkoxy $(C_1-C_6)$ alkyl group;

(e29) a $(C_2-C_6)$ alkynyloxy group;

(e30) a cyano group;

(e31) a $(C_2-C_6)$ alkynyl group;

(e32) a $(C_1-C_6)$ alkoxycarbonyl $(C_1-C_6)$ alkyl group;

(e33) a $(C_1-C_6)$ alkoxy $(C_2-C_6)$ alkynyl group;

(e34) a halo $(C_1-C_6)$ alkoxy $(C_2-C_6)$ alkynyl group;

(e35) a $R^1R^2N$ carbonyl group, wherein $R^1$ and $R^2$ have the same meaning as above;

(e36) a $R^1R^2N$ carbonyl $(C_1-C_6)$ alkoxy group, wherein $R^1$ and $R^2$ have the same meaning as above;

(e37) a $R^1R^2N$ carbonyl halo $(C_1-C_6)$ alkoxy group, wherein $R^1$ and $R^2$ have the same meaning as above; or $X^2$ and $X^3$ may be combined to form a 5- to 8-membered aliphatic ring together with the carbon atoms to which they are bound, and the aliphatic ring may have one to five substituents selected from a $(C_1-C_6)$ alkyl group and an oxo group.

Q is further preferably Q-2, Q-3, or Q-4.

R is further preferably (a1) a $(C_1-C_6)$ alkyl group.

$Y^1$, $Y^2$, $Y^3$ and $Y^4$, the same or different, are further preferably (b1) a hydrogen atom; or (b2) a halogen atom.

$X^1$ and $X^4$ are further preferably (c1) a hydrogen atom.

$X^2$ is further preferably (d7) a $(C_2-C_{12})$ alkynyl group;

(d9) a halo $(C_1-C_6)$ alkyl group;

(d18) a $(C_3-C_6)$ cycloalkyl $(C_2-C_6)$ alkynyl group;

(d20) a $(C_1-C_6)$ alkoxycarbonyl group;

(d24) a $(C_1-C_6)$ alkoxycarbonyl $(C_2-C_6)$ alkenyl group;

(d35) an aryl $(C_2-C_6)$ alkynyl group;

(d36) an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(d40) a halo $(C_1-C_6)$ alkoxycarbonyl group;

(d41) a halo $(C_1-C_6)$ alkoxycarbonyl $(C_2-C_6)$ alkenyl group;

(d42) an aryl $(C_1-C_6)$ alkoxycarbonyl $(C_2-C_6)$ alkenyl group;

(d43) an aryl $(C_1-C_6)$ alkoxycarbonyl $(C_2-C_6)$ alkenyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(d45) a heteroaryl $(C_2-C_6)$ alkynyl group;

(d46) a heteroaryl $(C_2-C_6)$ alkynyl group having the same or different one to four substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(d48) a $(C_1-C_6)$ alkoxy $(C_2-C_6)$ alkynyl group;

(d49) a $(C_1-C_6)$ alkoxy $(C_1-C_6)$ alkyl group;

(d50) a $(C_1-C_6)$ alkylcarbonyloxy $(C_2-C_6)$ alkynyl group;

(d52) a halo $(C_1-C_6)$ alkoxy $(C_2-C_6)$ alkynyl group;

(d53) an aryloxy $(C_2-C_6)$ alkynyl group; or (d54) an aryloxy $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group.

$X^3$ is further preferably (e2) a halogen atom;

(e4) a halo $(C_1-C_6)$ alkyl group;

(e6) a halo $(C_1-C_6)$ alkoxy group;

(e7) a $(C_1-C_6)$ alkoxycarbonyl $(C_2-C_6)$ alkenyl group;

(e9) a $(C_1-C_6)$ alkoxycarbonyl $(C_1-C_6)$ alkoxy group;

(e12) an aryl $(C_1-C_6)$ alkyl group;

(e13) an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(e22) a $(C_3-C_6)$ cycloalkyl group;

(e23) a $(C_3-C_6)$ cycloalkyl $(C_2-C_6)$ alkenyl group;

(e24) a $(C_3-C_6)$ cycloalkyl $(C_1-C_6)$ alkyl group;

(e25) a $(C_2-C_6)$ alkenyl group;

(e26) an aryl $(C_2-C_6)$ alkynyl group;

(e27) an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;

(e29) a $(C_2-C_6)$ alkynyloxy group;

(e31) a $(C_2-C_6)$ alkynyl group;

(e33) a $(C_1-C_6)$ alkoxy $(C_2-C_6)$ alkynyl group; or (e34) a halo $(C_1-C_6)$ alkoxy $(C_2-C_6)$ alkynyl group.

The benzimidazole compound represented by the general formula (1) or a salt thereof of the present invention can be produced by, for example, the following production method, but the present invention is not limited only thereto.

Production Method 1

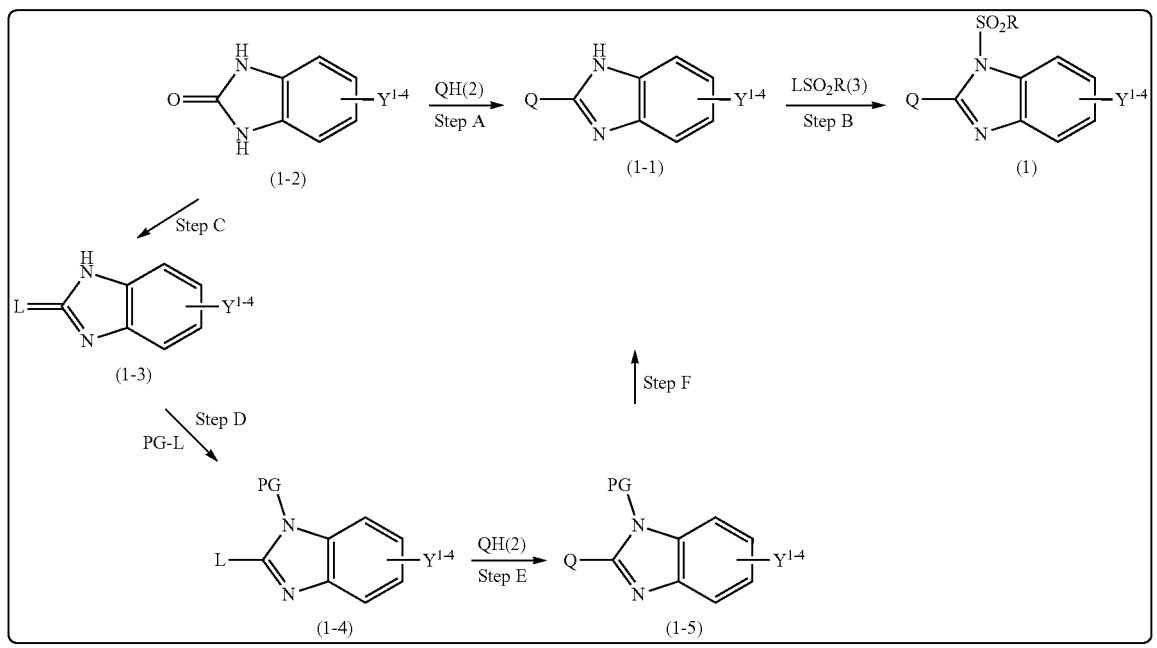

Q and R are the same as above, L is a halogen atom, PG is a protective group such as SEM, $Y^{1-4}$ is $Y^1$, $Y^2$, $Y^3$, and $Y^4$.

Production Method of Step [A]

The benzimidazole compound represented by the general formula (1-1) can be produced using the compound represented by the general formula (1-2) and the nitrogen-containing heterocyclic compound represented by the general formula (2) according to the method described in J.O.C., 2011, 76, 8262-8269.

After the completion of the reaction, the intended substance is isolated by a usual method from the reaction system containing the intended substance, and optionally purified by recrystallization, column chromatography or the like thereby to produce the intended substance. Alternatively, the subsequent step may be performed without isolating the benzimidazole compound represented by the general formula (1-1) from the reaction system.

Production Method of Step [B]

The benzimidazole compound represented by the general formula (1) can be produced by reacting the benzimidazole compound represented by the general formula (1-1) and the compound represented by the general formula (3) in the presence of a base and an inactive solvent.

Examples of the base used in the present reaction include inorganic bases such as sodium hydroxide, potassium hydroxide, sodium carbonate, potassium carbonate, sodium hydrogen carbonate, potassium hydrogen carbonate, sodium hydride, and potassium hydride, acetates such as sodium acetate and potassium acetate, alkali metal alkoxides such as potassium t-butoxide, sodium methoxide, and sodium ethoxide; tertiary amines such as triethylamine, diisopropylethylamine, and 1,8-diazabicyclo[5.4.0]undec-7-ene (DBU), and nitrogen-containing aromatic compounds such as pyridine, and dimethylaminopyridine (DMAP), and the amount thereof used is typically in the range of 1 time the mole to 10 times the mole to the compound represented by the general formula (1-1).

The inactive solvent used in the present reaction may be a solvent that does not notably inhibit the progress of the present reaction, and examples include inactive solvents such as aromatic hydrocarbons such as benzene, toluene, and xylene, halogenated aromatic hydrocarbons such as chlorobenzene, and dichlorobenzene, linear or cyclic ethers such as diethyl ether, methyl tertiary butyl ether, dioxane, and tetrahydrofuran (THF), amides such as dimethylformamide (DMF), dimethylacetamide (DMA), and N-methylpyrrolidone (NMP), ketones such as acetone, and methyl ethyl ketone, polar solvents such as dimethyl sulfoxide (DMSO), and 1,3-dimethyl-2-imidazolidinone (DMI), and alcohols such as methanol, ethanol, propanol, and isopropyl alcohol, and these inactive solvents can be used singly, or two or more can be used in mixture.

The present reaction is an equimolar reaction wherein each of the reactants is used in an equimolar amount, but whichever the reactant can be used in an excess amount. The reaction can be performed at the reaction temperature of room temperature to the boiling point of an inactive solvent used for the reaction time, which is variable depending on the reaction scale and reaction temperature, in the range of several minutes to 48 hours.

After the completion of the reaction, the intended substance is isolated by a usual method from the reaction system containing the intended substance, and optionally purified by recrystallization, column chromatography or the like thereby to produce the compound of the invention of the present application.

Production Method of Step [C]

The benzimidazole compound, even when cannot be produced by the production method of Step [A], can be produced by the route via the benzimidazole compound represented by the general formula (1-3). The benzimidazole compound represented by the general formula (1-3) can be produced by reacting the benzimidazole compound represented by the general formula (1-2) and a halogenating agent such as phosphorus oxychloride, phosphorus oxybromide, or thionyl chloride in the presence or absence of an inactive solvent.

The inactive solvent usable in the present reaction may be a solvent that does not notably inhibit the progress of the present reaction, and examples include inactive solvents such as aromatic hydrocarbons such as benzene, toluene, and xylene, halogenated hydrocarbons such as methylene chloride, chloroform, and carbon tetrachloride; halogenated aromatic hydrocarbons such as chlorobenzene, and dichlorobenzene, and these inactive solvents can be used singly, or two or more can be used in mixture.

The present reaction is an equimolar reaction wherein each of the reactants is used in an equimolar amount, but as described earlier, a halogenating agent can be used in an excess amount when a solvent is not used. The reaction can be performed at the reaction temperature of room temperature to the boiling point of an inactive solvent used for the reaction time, which is variable depending on the reaction scale and reaction temperature, in the range of several minutes to 48 hours.

After the completion of the reaction, the intended substance is isolated by a usual method from the reaction system containing the intended substance, and optionally purified by recrystallization, column chromatography or the like thereby to produce the intended substance.

Production Method of Step [D]

The benzimidazole compound represented by the general formula (1-4) can be produced by reacting the benzimidazole compound represented by the general formula (1-3) and a protective agent such as methoxymethyl chloride (MOMCl), methoxyethoxymethyl chloride (MEMCl), or 2-(trimethylsilyl)ethoxymethyl chloride (SEMCl) in the presence of a base and an inactive solvent.

Examples of the base used in the present reaction include inorganic bases such as sodium hydroxide, potassium hydroxide, sodium carbonate, potassium carbonate, sodium hydrogen carbonate, potassium hydrogen carbonate, sodium hydride, and potassium hydride, acetates such as sodium acetate and potassium acetate, alkali metal alkoxides such as potassium t-butoxide, sodium methoxide, and sodium ethoxide; tertiary amines such as triethylamine, diisopropylethylamine, and 1,8-diazabicyclo[5.4.0]undec-7-ene (DBU), and nitrogen-containing aromatic compounds such as pyridine, and dimethylaminopyridine (DMAP), and the amount thereof used is typically in the range of 1 time the mole to 10 times the mole to the compound represented by the general formula (1-3).

The inactive solvent usable in the present reaction may be a solvent that does not notably inhibit the progress of the present reaction, and examples include inactive solvents such as aromatic hydrocarbons such as benzene, toluene, and xylene, halogenated hydrocarbons such as methylene chloride, chloroform, and carbon tetrachloride; halogenated aromatic hydrocarbons such as chlorobenzene, and dichlorobenzene, linear or cyclic ethers such as diethyl ether, methyl tertiary butyl ether, dioxane, and tetrahydrofuran (THF), esters such as ethyl acetate, amides such as dimethylformamide (DMF), dimethylacetamide (DMA), and N-methylpyrrolidone (NMP), ketones such as acetone, and methyl ethyl ketone, polar solvents such as dimethyl sulfoxide (DMSO), and 1,3-dimethyl-2-imidazolidinone (DMI), and nitrogen-containing aromatic compounds such as pyridine, and these inactive solvents can be used singly, or two or more can be used in mixture.

The present reaction is an equimolar reaction wherein each of the reactants is used in an equimolar amount, but whichever the reactant can be used in an excess amount. The reaction can be performed at the reaction temperature of room temperature to the boiling point of an inactive solvent used for the reaction time, which is variable depending on the reaction scale and reaction temperature, in the range of several minutes to 48 hours.

After the completion of the reaction, the intended substance is isolated by a usual method from the reaction system containing the intended substance, and optionally purified by recrystallization, column chromatography or the like thereby to produce the intended substance. Alternatively, the subsequent step may be performed without isolating the intermediate from the reaction system.

Production Method of Step [E]

The benzimidazole compound represented by the general formula (1-5) can be produced by reacting the benzimidazole compound represented by the general formula (1-4) and the nitrogen-containing heterocyclic compound represented by the general formula (2) in the presence of an inactive solvent and a base.

Examples of the base used in the present reaction include inorganic bases such as sodium hydroxide, potassium hydroxide, sodium carbonate, potassium carbonate, sodium hydrogen carbonate, potassium hydrogen carbonate, and sodium hydride, acetates such as sodium acetate and potassium acetate, alkali metal alkoxides such as potassium t-butoxide, sodium methoxide, and sodium ethoxide; tertiary amines such as triethylamine, diisopropylethylamine, and 1,8-diazabicyclo[5.4.0]undec-7-ene (DBU), and nitrogen-containing aromatic compounds such as pyridine, and dimethylaminopyridine (DMAP), and the amount thereof used is typically in the range of 1 time the mole to 10 times the mole to the compound represented by the general formula (1-4).

The inactive solvent usable in the present reaction may be a solvent that does not notably inhibit the progress of the present reaction, and examples include aromatic hydrocarbons such as benzene, toluene, and xylene, halogenated hydrocarbons such as methylene chloride, chloroform, and carbon tetrachloride, halogenated aromatic hydrocarbons such as chlorobenzene, and dichlorobenzene, linear or cyclic ethers such as diethyl ether, tetrahydrofuran (THF), and dioxane, and amides such as dimethylformamide (DMF), dimethylacetamide (DMA), and N-methylpyrrolidone (NMP), and these inactive solvents can be used singly, or two or more can be used in mixture.

The present reaction is an equimolar reaction wherein each of the reactants is used in an equimolar amount, but whichever the reactant can be used in an excess amount. The reaction can be performed at the reaction temperature of room temperature to the boiling point of an inactive solvent used for the reaction time, which is variable depending on the reaction scale and reaction temperature, in the range of several minutes to 48 hours.

After the completion of the reaction, the intended substance is isolated by a usual method from the reaction system containing the intended substance, and optionally purified by recrystallization, column chromatography or the like thereby to produce the intended substance. Alternatively, the subsequent step may be performed without isolating the intermediate from the reaction system.

Production Method of Step [F]

The benzimidazole compound represented by the general formula (1-1) can be produced by deprotecting the protective group from the benzimidazole compound represented by the general formula (1-5) according to the method described in Greene's PROTECTIVE GROUPS in ORGANIC SYNTHESIS (4th Edition) 561-565 and the like.

After the completion of the reaction, the intended substance is isolated by a usual method from the reaction system containing the intended substance, and optionally purified by recrystallization, column chromatography or the like thereby to produce the intended substance. Alternatively, Step [B] may be performed without isolating the intermediate from the reaction system.

Production Method 2

[Formula 4]

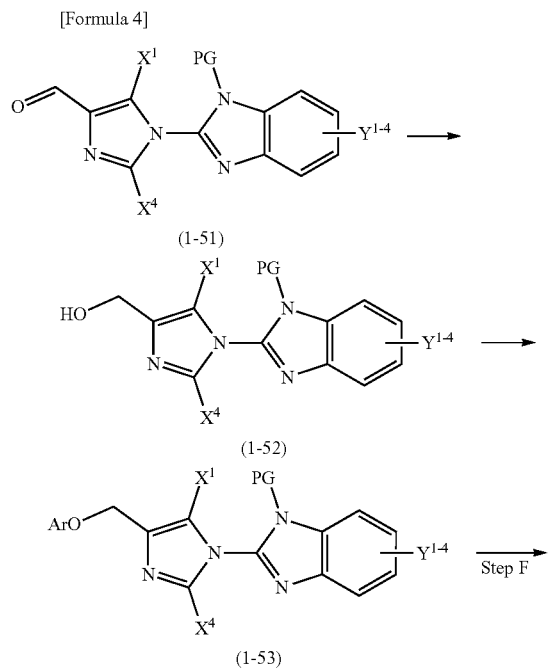

(1-51)

(1-52)

(1-53)

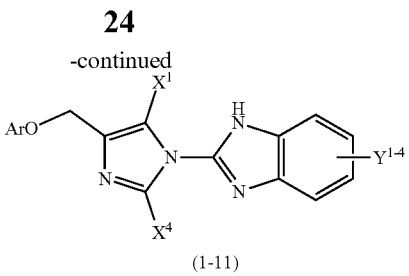

(1-11)

$X^1$ and $X^4$ are the same as above, PG is a protective group such as SEM, $Y^{1-4}$ is $Y^1$, $Y^2$, $Y^3$, and $Y^4$, and Ar is a unsubstituted or substituted aryl group.

The benzimidazole compound represented by the general formula (1) or a salt thereof can also be produced by the above method other than the production method disclosed in Production Method 1. The benzimidazole compound represented by the general formula (1-52) can be produced by reacting the compound represented by the general formula (1-51) produced according to the method disclosed in Production Method 1 and a reducing agent such as sodium borohydride, and potassium borohydride in a solvent such as methanol, ethanol, propanol, isopropyl alcohol, or tetrahydrofuran.

The compound represented by the general formula (1-53) can be produced by using the compound represented by the general formula (1-52) and phenols according to the method described in a literature (Bull. Chem. Soc. Jpn. 1967, 40, 935), so-called the Mitsunobu reaction.

The compound represented by the general formula (1-11) can be produced according to Step F described in Production Method 1 and can be induced to the compound of the invention of the present application further according to Step B.

The nitrogen-containing heterocyclic compound used in the above production method can be a commercial compound used as it is but can also be produced by the following method and used.

Production Method 1 of a Nitrogen-Containing Heterocyclic Compound

[Formula 5]

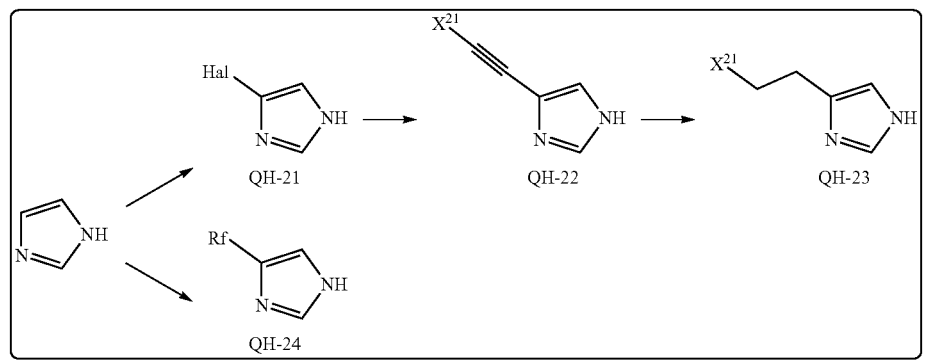

Hal is a halogen atom, $X^{21}$ is an alkyl group, an aryl group, or a substituted aryl group.

The compound represented by the general formula (QH-21) can be produced by reacting a commercial imidazole and a halogenating agent such as NCS (N-chlorosuccinimide), NBS (N-bromosuccinimide), DBH (1,3-dibromo-5,5-dimethylhydantoin), or DIH (1,3-diiodo-5,5-dimethylhydantoin) in the presence of a solvent such as acetonitrile, or propionitrile.

The compound represented by the general formula (QH-22) can be produced by using the compound represented by the general formula (QH-21) and an acetylene compound according to the method described in a literature (Tetrahedron Lett. 1975, 50, 4467, Synthesis, 364-365 (1981), Organic Letters, 11(1), 221-224, 2009), so-called the Sonogashira reaction.

The compound represented by the general formula (QH-23) can be produced by the catalytic hydrogenation reaction of the acetylene compound represented by the general formula (QH-22). The catalytic hydrogenation reaction can be performed in the presence of a catalyst, under normal pressure or applied pressure, in the presence or absence of an inactive solvent in a hydrogen atmosphere.

The compound represented by the general formula (QH-24) can be produced according to the method disclosed in Japanese Patent Laid-Open No. 2001-122836.

Production Method 2 of a Nitrogen-Containing Heterocyclic Compound

[Formula 6]

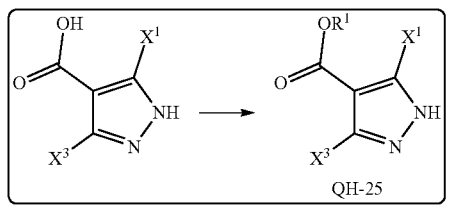

$X^1$ and $X^3$ are the same as above, $R^1$ is a $C_1$-$C_6$ alkyl group.

The compound represented by the general formula (QH-25) can be induced to an ester compound from the 1H-pyrazole-4-carboxylic acid produced according to the method described in a literature (WO2013/063221) by the method described in Greene's PROTECTIVE GROUPS in ORGANIC SYNTHESIS (4th Edition) 582-588.

Production Method 3 of a Nitrogen-Containing Heterocyclic Compound

[Formula 7]

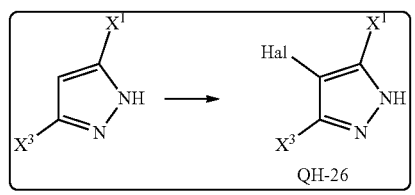

$X^1$ and $X^3$ are the same as above, and Hal is a halogen atom.

The compound represented by the general formula (QH-26) can be produced by the same production method as QH-21 of Production method 1 of a nitrogen-containing heterocyclic compound.

Production Method 4 of a Nitrogen-Containing Heterocyclic Compound

[Formula 8]

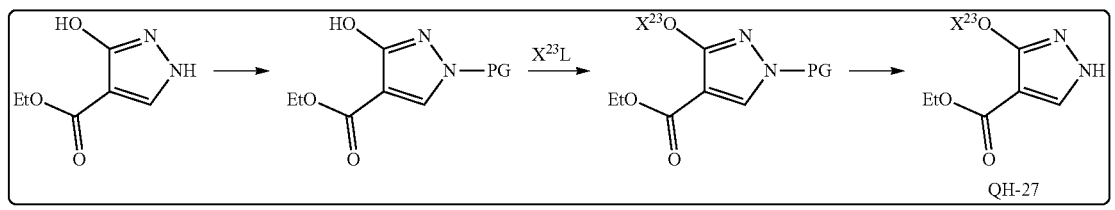

PG is a protective group, $X^{23}$ is a $C_1$-$C_6$ haloalkyl group, L is a halogen atom or a leaving group such as triflate.

The compound represented by the general formula (QH-27) can be produced by protecting the pyrazole ring at position 1 in 3-hydroxy-1H-pyrazole-4-carboxylic acid ethyl ester produced using a commercial diethyl ethoxymethylidenemalonate and hydrazine hydrate by the method described in Greene's PROTECTIVE GROUPS in ORGANIC SYNTHESIS (4th Edition) 582-588, reacting the compound in which the pyrazole ring at position 1 is thus protected and $X^{23}$ L using sodium carbonate or potassium carbonate in a solvent such as dimethylformamide (DMF), dimethylacetamide (DMA) or the like, and then deprotecting the protective group of the pyrazole ring by the method described in Greene's PROTECTIVE GROUPS in ORGANIC SYNTHESIS (4th Edition) 582-588.

Next, specific examples of the compounds of the present invention and their production intermediates are shown below. In the following tables, Me is a methyl group, Et is an ethyl group, a n-Pr is a normal propyl group, i-Pr is an isopropyl group, n-Bu is a normal butyl group, i-Bu is an isobutyl group, t-Bu is a tertiary butyl group, n-Pen is a normal pentyl group, t-Amyl is a tertiary amyl group, Ph is a phenyl group, and c-Pr is a cyclopropyl group. E and Z are geometrical isomers. Physical property is a melting point (° C.), a refractive index nD (measurement temperature; ° C.), or $H^1$-NMR, and $H^1$-NMR data are shown in Table 16 to Table 24, and Table 39 to Table 44.

[Formula 9]

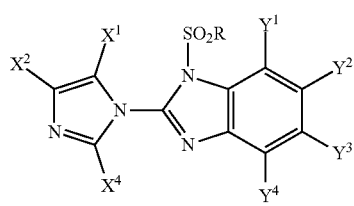

(1 - A)

TABLE 1

| Compound No. | $X^2$ | $Y^1$ | $Y^2$ | $Y^3$ | $Y^4$ | R | Physical property |
|---|---|---|---|---|---|---|---|
| 1-1 | H | H | H | H | H | Et | NMR |
| 1-2 | n-$C_5H_{11}$ | H | H | H | H | Et | NMR |
| 1-3 | n-$C_8H_{17}$ | H | H | H | H | Me | 72-73 |
| 1-4 | n-$C_8H_{17}$ | H | H | H | H | Et | NMR |
| 1-5 | t-Bu | H | H | H | H | Et | 1.558(26.7) |
| 1-6 | n-$C_6H_{13}$CH=CH (Z) | H | H | H | H | Et | 1.521(26.3) |
| 1-7 | c-PrC≡C | H | H | H | H | Et | NMR |
| 1-8 | $PhCH_2$ | H | H | H | H | Et | 128-129 |
| 1-9 | $PhCH_2CH_2$ | H | H | H | H | Et | 107 |
| 1-10 | 4-(t-Bu)$PhCH_2CH_2$ | H | H | H | H | Et | NMR |
| 1-11 | 4-$CF_3PhCH_2CH_2$ | H | H | H | H | Et | 48-51 |
| 1-12 | 4-$ClPhCH_2CH_2$ | H | H | H | H | Et | NMR |
| 1-13 | 2,4-$Cl_2PhCH_2CH_2$ | H | H | H | H | Et | 86-88 |
| 1-14 | 4-$BrPhCH_2CH_2$ | H | H | H | H | Et | NMR |
| 1-15 | $PhOCH_2$ | H | H | H | H | Et | NMR |
| 1-16 | 4-$CF_3PhOCH_2$ | H | H | H | H | Et | 148-150 |
| 1-17 | 4-$CF_3OPhOCH_2$ | H | H | H | H | Et | 129-131 |
| 1-18 | PhC≡C | H | H | H | H | Et | NMR |
| 1-19 | Br | H | H | H | H | Et | 178-179 |
| 1-20 | I | H | H | H | H | Et | 154-155 |
| 1-21 | $CF_3$ | H | H | H | H | Et | 83-84 |
| 1-22 | $(CF_3)_2CF$ | H | H | H | H | Et | 129 |

TABLE 1-continued

| Compound No. | $X^2$ | $Y^1$ | $Y^2$ | $Y^3$ | $Y^4$ | R | Physical property |
|---|---|---|---|---|---|---|---|
| 1-23 | $(CF_3)_2CF$ | H | H | H | H | Me | 119-120 |
| 1-24 | $(CF_3)_2CF$ | H | H | H | H | $CF_3$ | 112-113 |
| 1-25 | $(CF_3)_2CF$ | H | H | H | H | n-Pr | NMR |
| 1-26 | $(CF_3)_2CF$ | H | Br | Br | H | Et | 148-149 |
| 1-27 | n-$C_4F_9$ | H | H | H | H | Et | 1.588(25.5) |
| 1-28 | n-$C_6F_{13}$ | H | H | H | H | Et | 46-47 |
| 1-29 | $CO_2Et$ | H | H | H | H | Et | 110-111 |
| 1-30 | CONHPh | H | H | H | H | Et | 42-43 |

In the formulas, $X^1$ and $X^4$ are a hydrogen atom.

TABLE 2

| Compound No. | $X^2$ | $Y^1$ | $Y^2$ | $Y^3$ | $Y^4$ | R | Physical property |
|---|---|---|---|---|---|---|---|
| 1-31 | CN | H | H | H | H | Et | NMR |
| 1-32 | n-$C_3F_7CH_2OCH_2$ | H | H | H | H | Et | NMR |
| 1-33 | $CO_2$(t-Bu) | H | H | H | H | Et | NMR |
| 1-34 | $CO_2$(t-Amyl) | H | H | H | H | Et | |
| 1-35 | $CO_2(CMe_2C≡CH)$ | H | H | H | H | Et | |
| 1-36 | $CO_2(CMe_2Ph)$ | H | H | H | H | Et | NMR |
| 1-37 | $CO_2$(2,6-$Me_2Ph$) | H | H | H | H | Et | 147-148 |

In the formulas, $X^1$ and $X^4$ are a hydrogen atom.

TABLE 3

| Compound No. | $X^2$ | $Y^1$ | $Y^2$ | $Y^3$ | $Y^4$ | R | Physical property |
|---|---|---|---|---|---|---|---|
| 1-38 | $(CF_3)_2CF$ | H | Me | Me | H | Et | 182-184 |
| 1-39 | $CO_2CH(CF_3)_2$ | H | H | H | H | Et | NMR |
| 1-40 | $CO_2(CMe_2CH_2Ph)$ | H | H | H | H | Et | NMR |
| 1-41 | $CO_2(CMe_2CH_2CH_2Ph)$ | H | H | H | H | Et | NMR |
| 1-42 | $CO_2$(2-MePh) | H | H | H | H | Et | NMR |
| 1-43 | CH=$CHCO_2CH_2$(t-Bu) (E) | H | H | H | H | Et | 86-90 |
| 1-44 | CH=$CHCO_2CH(CF_3)_2$ (E) | H | H | H | H | Et | 159-161 |
| 1-45 | CONHt-Bu | H | H | H | H | Et | NMR |
| 1-46 | $CONHC(Me)_2Ph$ | H | H | H | H | Et | NMR |

In the formulas, $X^1$ and $X^4$ are a hydrogen atom.

[Formula 10]

(1 - B)

TABLE 4

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-1 | H | H | H | H | H | H | H | Et | 130-131 |
| 2-2 | H | n-$C_8H_{17}$ | H | H | H | H | H | Et | 1.597(25.6) |
| 2-3 | H | $PhCH_2CH_2$ | H | H | H | H | H | Et | NMR |
| 2-4 | H | 4-$CF_3PhCH_2CH_2$ | H | H | H | H | H | Et | 75-76 |
| 2-5 | H | 4-$FPhCH_2CH_2$ | $CF_3$ | H | H | H | H | Et | NMR |
| 2-6 | H | 4-$MeOPhCH_2CH_2$ | $CF_3$ | H | H | H | H | Et | NMR |
| 2-7 | H | n-$C_6H_{13}$C≡C | H | H | H | H | H | Et | 1.523(25.0) |
| 2-8 | H | 4-$CF_3$PhC≡C | H | H | H | H | H | Et | 95-96 |
| 2-9 | H | 4-FPhC≡C | $CF_3$ | H | H | H | H | Et | 137-138 |
| 2-10 | H | $(CF_3)_2CF$ | H | H | H | H | H | Et | NMR |
| 2-11 | H | $CO_2$(t-Bu) | H | H | H | H | H | Et | NMR |
| 2-12 | H | H | $CF_3$ | H | H | H | H | Et | 142-143 |
| 2-13 | H | Cl | $CF_3$ | H | H | H | H | Et | 144-145 |
| 2-14 | H | Br | $CF_3$ | H | H | H | H | Et | 140-141 |
| 2-15 | H | I | $CF_3$ | H | H | H | H | Me | 86-87 |
| 2-16 | H | I | $CF_3$ | H | H | H | H | Et | 165-166 |
| 2-17 | Me | H | $CF_3$ | H | H | H | H | Et | NMR |
| 2-18 | Me | Br | $CF_3$ | H | H | H | H | Et | 108-109 |
| 2-19 | H | Et | $CF_3$ | H | H | H | H | Et | NMR |
| 2-20 | H | c-Pr | $CF_3$ | H | H | H | H | Et | NMR |
| 2-21 | H | CH=$CH_2$ | $CF_3$ | H | H | H | H | Et | 110-111 |
| 2-22 | H | $PhCH_2$ | $CF_3$ | H | H | H | H | Et | NMR |
| 2-23 | H | $PhCH_2CH_2$ | $CF_3$ | H | H | H | H | Et | 91-92 |
| 2-24 | H | CH=CHCO$_2$(t-Bu) (E) | $CF_3$ | H | H | H | H | Et | NMR |
| 2-25 | H | $COCH_3$ | $CF_3$ | H | H | H | H | Et | NMR |
| 2-26 | H | $CO_2Et$ | $CF_3$ | H | H | H | H | Et | 95-96 |
| 2-27 | H | $CO_2$(t-Bu) | $CF_3$ | H | H | H | H | Et | NMR |
| 2-28 | H | $CO_2CH_2$(t-Bu) | $CF_3$ | H | H | H | H | Et | 1.495(25.9) |
| 2-29 | H | $CO_2$(2,6-$Me_2$Ph) | $CF_3$ | H | H | H | H | Et | 1.502(25.9) |
| 2-30 | H | CONMe(OMe) | $CF_3$ | H | H | H | H | Et | NMR |

TABLE 5

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-31 | H | COS(t-Bu) | $CF_3$ | H | H | H | H | Et | NMR |
| 2-32 | H | i-PrS | $CF_3$ | H | H | H | H | Et | NMR |
| 2-33 | H | $CO_2Et$ | $CHF_2$ | H | H | H | H | Et | 127-128 |
| 2-34 | H | Br | Br | H | H | H | H | Et | NMR |
| 2-35 | H | I | Br | H | H | H | H | Et | 146-147 |
| 2-36 | H | H | CH=CHCO$_2$Et (E) | H | H | H | H | Et | NMR |
| 2-37 | H | Br | n-BuO | H | H | H | H | Et | 112-114 |
| 2-38 | H | H | $CF_3CF_2CH_2O$ | H | H | H | H | Et | 129-130 |
| 2-39 | H | Cl | $CF_3CF_2CH_2O$ | H | H | H | H | Et | 100-101 |
| 2-40 | H | Br | $CF_3CF_2CH_2O$ | H | H | H | H | Et | 119-120 |
| 2-41 | H | $CO_2Et$ | $CF_3CF_2CH_2O$ | H | H | H | H | Et | 36-37 |
| 2-42 | H | Br | $CHF_2O$ | H | H | H | H | Et | 127-128 |
| 2-43 | H | H | $CO_2$(t-Bu) | H | H | H | H | Et | 136-137 |
| 2-44 | H | Cl | $CO_2$(t-Bu) | H | H | H | H | Et | NMR |
| 2-45 | H | Br | $CO_2$(t-Bu) | H | H | H | H | Et | 139-140 |
| 2-46 | H | H | 4-$ClPhSO_2$ | H | H | H | H | Et | NMR |
| 2-47 | H | $CO_2$(t-Bu) | Cl | H | H | H | H | Et | 114-115 |
| 2-48 | H | $CO_2$(t-Bu) | Br | H | H | H | H | Et | 106-107 |
| 2-49 | H | $CO_2$(t-Bu) | Et | H | H | H | H | Et | 117-118 |
| 2-50 | H | $CO_2$(t-Bu) | c-Pr | H | H | H | H | Et | 115-116 |
| 2-51 | H | $CO_2$(t-Bu) | $CHF_2$ | H | H | H | H | Et | NMR |
| 2-52 | H | $CO_2$(t-Bu) | $CF_3CF_2CH_2O$ | H | H | H | H | Et | NMR |
| 2-53 | H | $CO_2$(i-Pr) | $CF_3$ | H | H | H | H | Et | NMR |
| 2-54 | H | $CO_2$(t-Amyl) | $CF_3$ | H | H | H | H | Et | NMR |
| 2-55 | H | i-PrSO | $CF_3$ | H | H | H | H | Et | NMR |
| 2-56 | H | i-PrSO$_2$ | $CF_3$ | H | H | H | H | Et | NMR |
| 2-57 | H | $CO_2$(t-Bu) | i-Pr | H | H | H | H | Et | 140-142 |
| 2-58 | H | $CO_2$(t-Bu) | t-Bu | H | H | H | H | Et | 149-150 |
| 2-59 | H | COPh | $CF_3$ | H | H | H | H | Et | NMR |
| 2-60 | H | $PhCH_2CH_2$ | $CHF_3$ | H | H | H | H | Et | |

TABLE 6

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-61 | H | $CH_2CH_2CO_2$(t-Bu) | $CF_3$ | H | H | H | H | Et | 89-90 |
| 2-62 | H | $CO_2$(t-Bu) | $CO_2$(t-Bu) | H | H | H | H | Et | 130-133 |
| 2-63 | H | H | $OCH_2CO_2$(t-Bu) | H | H | H | H | Et | |
| 2-64 | H | H | $OCH_2CH_2CO_2$(t-Bu) | H | H | H | H | Et | |
| 2-65 | H | H | $CF_3$ | H | Me | Me | H | Et | |
| 2-66 | H | H | $CF_3$ | H | Cl | H | $CF_3$ | Et | |
| 2-67 | H | H | $CF_3$ | H | $CF_3$ | H | Cl | Et | |
| 2-68 | H | $CO_2$(t-Bu) | H | H | Me | Me | H | Et | |
| 2-69 | H | $CO_2$(t-Bu) | H | H | Cl | H | $CF_3$ | Et | |
| 2-70 | H | $CO_2$(t-Bu) | H | H | $CF_3$ | H | Cl | Et | |
| 2-71 | H | $CO_2$(t-Bu) | Me | H | H | H | H | Et | |
| 2-72 | H | $CO_2$(t-Bu) | n-Pr | H | H | H | H | Et | 86-87 |
| 2-73 | H | $CO_2$(t-Bu) | EtO | H | H | H | H | Et | 72-73 |
| 2-74 | H | $CO_2$(t-Bu) | n-PrO | H | H | H | H | Et | NMR |
| 2-75 | H | $CO_2$(t-Bu) | n-BuO | H | H | H | H | Et | |
| 2-76 | H | $CO_2$(t-Bu) | $CF_3CH_2O$ | H | H | H | H | Et | 60-62 |
| 2-77 | H | $CO_2$(t-Bu) | $CHF_2CH_2O$ | H | H | H | H | Et | NMR |
| 2-78 | H | $CO_2$(t-Bu) | $CHF_2CF_2CH_2O$ | H | H | H | H | Et | 125-127 |

TABLE 7

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-79 | H | $CO_2Me$ | t-Bu | H | H | H | H | Et | 164-166 |
| 2-80 | H | $CO_2Et$ | CH=CHc-Pr (E) | H | H | H | H | Et | 142-144 |
| 2-81 | H | $CO_2Et$ | I | H | H | H | H | Et | NMR |
| 2-82 | H | $CO_2$(t-Bu) | I | H | H | H | H | Et | NMR |
| 2-83 | H | $CO_2$(t-Bu) | CH=CHc-Pr (E) | H | H | H | H | Et | NMR |
| 2-84 | H | $CO_2$(t-Bu) | $CH_2CH_2$c-Pr | H | H | H | H | Et | NMR |
| 2-85 | H | $CO_2$(t-Bu) | n-$C_5H_{11}$ | H | H | H | H | Et | NMR |
| 2-86 | H | $CO_2$(t-Bu) | CH=$CMe_2$ | H | H | H | H | Et | NMR |
| 2-87 | H | $CO_2$(t-Bu) | i-Bu | H | H | H | H | Et | NMR |
| 2-88 | H | $CO_2$(t-Bu) | PhC≡C | H | H | H | H | Et | 151-154 |
| 2-89 | H | $CO_2$(t-Bu) | $PhCH_2CH_2$ | H | H | H | H | Et | NMR |
| 2-90 | H | $CO_2$(t-Bu) | $C_2F_5$ | H | H | H | H | Et | NMR |
| 2-91 | Me | $CO_2$(t-Bu) | t-$BuOCH_2$ | H | H | H | H | Et | NMR |
| 2-92 | H | $CO_2$(t-Bu) | HC≡$CCH_2O$ | H | H | H | H | Et | NMR |
| 2-93 | H | $CO_2CH(CF_3)_2$ | H | H | H | H | H | Et | 150-151 |
| 2-94 | H | $CONHCH_2CF_3$ | t-Bu | H | H | H | H | Et | NMR |
| 2-95 | H | $CONHCH_2CF_3$ | $CONHCH_2CF_3$ | H | H | H | H | Et | NMR |
| 2-96 | H | CONH(c-Pr) | t-Bu | H | H | H | H | Et | 137-139 |
| 2-97 | H | CONH(t-Bu) | t-Bu | H | H | H | H | Et | NMR |
| 2-98 | H | CONMe(t-Bu) | CONMe(t-Bu) | H | H | H | H | Et | NMR |
| 2-99 | H | CN | t-Bu | H | H | H | H | Et | NMR |
| 2-100 | H | PhC≡C | $CF_3CH_2O$ | H | H | H | H | Et | 151-153 |
| 2-101 | H | $PhCH_2CH_2$ | $CF_3CH_2O$ | H | H | H | H | Et | 125-126 |
| 2-102 | H | $CH_2CH_2CO_2$(t-Bu) | $CF_3CH_2O$ | H | H | H | H | Et | NMR |
| 2-103 | H | H | $OCH_2CH_2CH_2CO_2$(t-Bu) | H | H | H | H | Et | NMR |

TABLE 8

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-104 | H | I | $CO_2$(t-Bu) | H | H | H | H | Et | 82-83 |
| 2-105 | H | c-Pr | $CO_2$(t-Bu) | H | H | H | H | Et | 142-143 |
| 2-106 | H | PhC≡C | $CO_2$(t-Bu) | H | H | H | H | Et | 181-183 |
| 2-107 | H | $PhCH_2CH_2$ | $CO_2$(t-Bu) | H | H | H | H | Et | NMR |
| 2-108 | H | CN | $CO_2$(t-Bu) | H | H | H | H | Et | 160-162 |
| 2-109 | H | $PhCH_2CH_2$ | CN | H | H | H | H | Et | NMR |
| 2-110 | H | HC≡C | $CF_3$ | H | H | H | H | Et | 140-142 |
| 2-111 | H | CN | $C_2F_5$ | H | H | H | H | Et | NMR |
| 2-112 | H | CH=$CHCO_2CH(CF_3)_2$ (E) | $CF_3$ | H | H | H | H | Et | 105-106 |
| 2-113 | H | CH=$CHCO_2CH_2$(t-Bu) (E) | $CF_3$ | H | H | H | H | Et | NMR |
| 2-114 | H | CH=$CHCO_2CH_2$(4-t-Bu)Ph (E) | $CF_3$ | H | H | H | H | Et | 120-123 |
| 2-115 | H | CH=$CHCO_2CH_2$(4-$CF_3$)Ph (E) | $CF_3$ | H | H | H | H | Et | NMR |
| 2-116 | H | CH=$CHCO_2CH_2$(1-Ad) (E) | $CF_3$ | H | H | H | H | Et | NMR |

TABLE 8-continued

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-117 | H | CH=CHCONHCH$_2$CF$_3$ (E) | CF$_3$ | H | H | H | H | Et | 78-80 |
| 2-118 | H | (2-Py)C≡C | CF$_3$ | H | H | H | H | Et | NMR |
| 2-119 | H | Ac | Me | H | H | H | H | Et | NMR |
| 2-120 | H | SO$_2$NMe$_2$ | CF$_3$ | H | H | H | H | Et | 149-152 |
| 2-121 | H | 4-t-BuBnS | CF$_3$ | H | H | H | H | Et | NMR |
| 2-122 | H | n-PrC≡C | CF$_3$ | H | H | H | H | Et | 82-84 |
| 2-123 | H | c-PrC≡C | CF$_3$ | H | H | H | H | Et | 120-123 |
| 2-124 | H | t-BuC≡C | CF$_3$ | H | H | H | H | Et | 110-112 |
| 2-125 | H | n-Pen | CF$_3$ | H | H | H | H | Et | 70-72 |
| 2-126 | H | c-PrCH$_2$CH$_2$ | CF$_3$ | H | H | H | H | Et | 49-51 |
| 2-127 | H | t-BuCH$_2$CH$_2$ | CF$_3$ | H | H | H | H | Et | 105-108 |
| 2-128 | H | MeOCH$_2$C≡C | CF$_3$ | H | H | H | H | Et | 70-72 |

TABLE 9

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-129 | H | MeOC(Me)$_2$C≡C | CF$_3$ | H | H | H | H | Et | 70-72 |
| 2-130 | H | CH=CHCO$_2$(t-Bu) (E) | CO$_2$(t-Bu) | H | H | H | H | Et | 145-147 |
| 2-131 | H | COCH$_2$(t-Bu) | CH$_2$(t-Bu) | H | H | H | H | Et | NMR |
| 2-132 | H | t-BuCO$_2$CH$_2$C≡C | CF$_3$ | H | H | H | H | Et | NMR |
| 2-133 | H | t-BuC≡C | CO$_2$(t-Bu) | H | H | H | H | Et | 156-158 |
| 2-134 | H | t-BuCO$_2$CH$_2$CH$_2$CH$_2$ | CF$_3$ | H | H | H | H | Et | 108-111 |
| 2-135 | H | CH$_2$CH$_2$CO$_2$(t-Bu) | CO$_2$(t-Bu) | H | H | H | H | Et | NMR |
| 2-136 | H | Br | OCF$_2$CONMe$_2$ | H | H | H | H | Et | NMR |
| 2-137 | H | t-BuCH$_2$CH$_2$ | CO$_2$(t-Bu) | H | H | H | H | Et | 154-162 |
| 2-138 | H | CF$_3$CH$_2$OCH$_2$C≡C | CF$_3$ | H | H | H | H | Et | 86-88 |
| 2-139 | H | CO$_2$(t-Bu) | OCHF$_2$ | H | H | H | H | Et | NMR |
| 2-140 | H | —COC(Me)$_2$CH$_2$CH$_2$— | | H | H | H | H | Et | NMR |
| 2-141 | H | SCH$_2$CF$_2$CF$_3$ | H | H | H | H | H | Et | NMR |
| 2-142 | H | COi-Bu | i-Bu | H | H | H | H | Et | NMR |
| 2-143 | H | CO$_2$Et | CH=CHCO$_2$Et (E) | H | H | H | H | Et | NMR |
| 2-144 | H | CO$_2$(t-Bu) | CH=CHCO$_2$(t-Bu) (E) | H | H | H | H | Et | NMR |
| 2-145 | H | CO$_2$(t-Bu) | t-BuC≡C | H | H | H | H | Et | NMR |
| 2-146 | H | I | Me | H | H | H | H | Et | NMR |
| 2-147 | H | t-BuC≡C | Me | H | H | H | H | Et | 146-156 |
| 2-148 | H | CO$_2$Et | CH$_2$CH$_2$CO$_2$Et | H | H | H | H | Et | NMR |
| 2-149 | H | COEt | Et | H | H | H | H | Et | NMR |
| 2-150 | H | SCF$_3$ | H | H | H | H | H | Et | NMR |
| 2-151 | H | t-BuCH$_2$OCH$_2$C≡C | CF$_3$ | H | H | H | H | Et | |
| 2-152 | H | t-BuCH$_2$CH$_2$OCH$_2$C≡C | CF$_3$ | H | H | H | H | Et | |
| 2-153 | H | t-BuC≡C | CF$_3$CF$_2$CH$_2$O | H | H | H | H | Et | 61-62 |

TABLE 10

| Compound No. | $X^1$ | $X^2$ | $X^3$ | $Y^1$ | $Y^2$ | $Y^3$ | $Y^4$ | R | Physical property |
|---|---|---|---|---|---|---|---|---|---|
| 2-154 | H | MeOC(Me)$_2$C≡C | CF$_3$CF$_2$CH$_2$O | H | H | H | H | Et | 71-72 |
| 2-155 | H | CH=CHCO$_2$(t-Bu) (E) | OCHF$_2$ | H | H | H | H | Et | NMR |
| 2-156 | H | CH$_2$CH$_2$CO$_2$(t-Bu) | OCHF$_2$ | H | H | H | H | Et | NMR |
| 2-157 | H | t-BuC≡C | OCHF$_2$ | H | H | H | H | Et | NMR |
| 2-158 | H | t-BuCH$_2$CH$_2$ | OCHF$_2$ | H | H | H | H | Et | NMR |
| 2-159 | H | MeOC(Me)$_2$C≡C | CO$_2$(t-Bu) | H | H | H | H | Et | |
| 2-160 | H | MeOC(Me)$_2$CH$_2$CH$_2$ | CO$_2$(t-Bu) | H | H | H | H | Et | NMR |
| 2-161 | H | —COC(Et)$_2$CH$_2$CH$_2$— | | H | H | H | H | Et | NMR |
| 2-162 | H | t-BuCH$_2$CH$_2$ | Me | H | H | H | H | Et | NMR |
| 2-163 | H | PhOCH$_2$C≡C | Me | H | H | H | H | Et | NMR |
| 2-164 | H | PhOCH$_2$CH$_2$CH$_2$ | Me | H | H | H | H | Et | |
| 2-165 | H | MeOC(Me)$_2$C≡C | Me | H | H | H | H | Et | |
| 2-166 | H | MeOC(Me)$_2$CH$_2$CH$_2$ | Me | H | H | H | H | Et | NMR |
| 2-167 | H | CO$_2$(t-Bu) | CH$_2$CH$_2$CO$_2$(t-Bu) | H | H | H | H | Et | NMR |
| 2-168 | H | CO$_2$(t-Bu) | MeOCH$_2$C≡C | H | H | H | H | Et | NMR |
| 2-169 | H | CO$_2$(t-Bu) | MeOC(Me)$_2$C≡C | H | H | H | H | Et | NMR |
| 2-170 | H | CO$_2$(t-Bu) | CF$_3$CH$_2$OCH$_2$C≡C | H | H | H | H | Et | |

TABLE 10-continued

| Compound No. | X¹ | X² | X³ | Y¹ | Y² | Y³ | Y⁴ | R | Physical property |
|---|---|---|---|---|---|---|---|---|---|
| 2-171 | H | $CO_2$(t-Bu) | $CF_3CH_2OC(Me)_2C\equiv C$ | H | H | H | H | Et | |
| 2-172 | H | C(=NOMe)i-Bu | i-Bu | H | H | H | H | Et | |

[Formula 11]

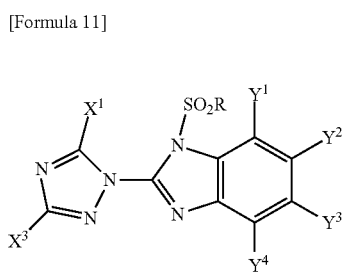

(1-C)

[Formula 12]

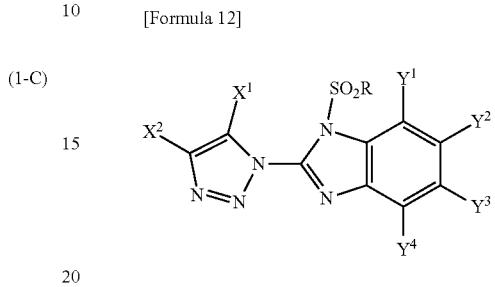

(1-D)

TABLE 11

| Compound No. | X¹ | X³ | Y¹ | Y² | Y³ | Y⁴ | R | Physical property |
|---|---|---|---|---|---|---|---|---|
| 3-1 | H | $CF_3$ | H | H | H | H | Et | NMR |
| 3-2 | H | $C_2F_5$ | H | H | H | H | Et | NMR |
| 3-3 | H | $PhCH_2CH_2$ | H | H | H | H | Et | NMR |
| 3-4 | H | SMe | H | H | H | H | Et | 101-102 |
| 3-5 | H | $CO_2$(t-Bu) | H | H | H | H | Et | |
| 3-6 | H | $CO_2$(t-Amyl) | H | H | H | H | Et | |
| 3-7 | H | $CO_2(CMe_2C\equiv CH)$ | H | H | H | H | Et | |
| 3-8 | H | $CO_2(CMe_2Ph)$ | H | H | H | H | Et | |
| 3-9 | H | $CO_2(2,6-Me_2Ph)$ | H | H | H | H | Et | |

TABLE 12

| Compound No. | X¹ | X² | Y¹ | Y² | Y³ | Y⁴ | R | Physical property |
|---|---|---|---|---|---|---|---|---|
| 4-1 | H | $CO_2$(t-Bu) | H | H | H | H | Et | |
| 4-2 | H | $CO_2$(t-Amyl) | H | H | H | H | Et | |
| 4-3 | H | $CO_2(CMe_2C\equiv CH)$ | H | H | H | H | Et | |
| 4-4 | H | $CO_2(CMe_2Ph)$ | H | H | H | H | Et | |
| 4-5 | H | $CO_2(2,6-Me_2Ph)$ | H | H | H | H | Et | |

[Formula 13]

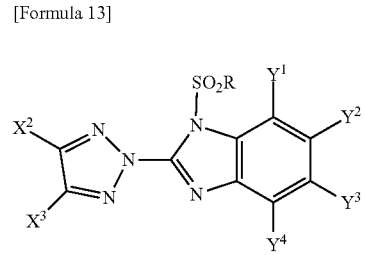

(1-E)

TABLE 13

| Compound No. | X² | X³ | Y¹ | Y² | Y³ | Y⁴ | R | Physical property |
|---|---|---|---|---|---|---|---|---|
| 5-1 | H | $CO_2$(t-Bu) | H | H | H | H | Et | |
| 5-2 | Me | $CO_2$(t-Bu) | H | H | H | H | Et | |
| 5-3 | Me | $CO_2$(t-Amyl) | H | H | H | H | Et | |
| 5-4 | Me | $CO_2(CMe_2C\equiv CH)$ | H | H | H | H | Et | |
| 5-5 | Me | $CO_2(CMe_2Ph)$ | H | H | H | H | Et | |
| 5-6 | Me | $CO_2(2,6-Me_2Ph)$ | H | H | H | H | Et | |
| 5-7 | $CO_2$(t-Bu) | $CO_2$(t-Bu) | H | H | H | H | Et | |

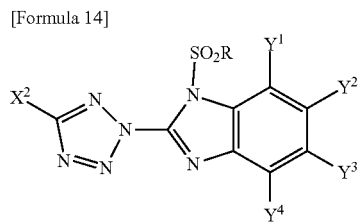

(1-F)

TABLE 14

| Compound No. | $X^2$ | $Y^1$ | $Y^2$ | $Y^3$ | $Y^4$ | R | Physical property |
|---|---|---|---|---|---|---|---|
| 6-1 | $CO_2(t\text{-}Bu)$ | H | H | H | H | Et | |
| 6-2 | $CO_2(t\text{-}Amyl)$ | H | H | H | H | Et | |
| 6-3 | $CO_2(CMe_2C\equiv CH)$ | H | H | H | H | Et | |
| 6-4 | $CO_2(CMe_2Ph)$ | H | H | H | H | Et | |
| 6-5 | $CO_2(2,6\text{-}Me_2Ph)$ | H | H | H | H | Et | |

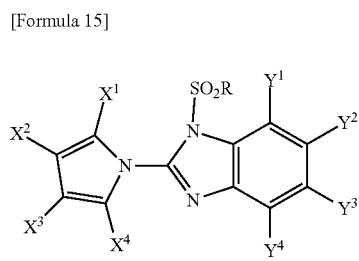

(1-G)

TABLE 15

| Compound No. | $X^1$ | $X^2$ | $X^3$ | $X^4$ | $Y^1$ | $Y^2$ | $Y^3$ | $Y^4$ | R | Physical property |
|---|---|---|---|---|---|---|---|---|---|---|
| 7-1 | H | $CO_2(t\text{-}Bu)$ | H | H | H | H | H | H | Et | NMR |
| 7-2 | H | $CO_2(t\text{-}Amyl)$ | H | H | H | H | H | H | Et | |
| 7-3 | H | $CO_2(CMe_2C\equiv CH)$ | H | H | H | H | H | H | Et | |
| 7-4 | H | $CO_2(CMe_2Ph)$ | H | H | H | H | H | H | Et | |
| 7-5 | H | $CO_2(2,6\text{-}Me_2Ph)$ | H | H | H | H | H | H | Et | |
| 7-6 | H | $CO_2Me$ | $CO_2Me$ | H | H | H | H | H | Et | NMR |
| 7-7 | H | $CO_2Et$ | $CO_2Et$ | H | H | H | H | H | Et | |

TABLE 16

| Compound No. | $^1$H-NMR data ($CDCl_3$) |
|---|---|
| 1-1 | 8.41(s, 1H), 7.81(s, 1H), 7.35-7.28(m, 4H), 3.81(q, 2H), 1.51(t, 3H) |
| 1-2 | 8.03-7.95(m, 2H), 7.82-7.75(m, 1H), 7.51-7.45(m, 2H), 7.20(s, 1H), 3.25-3.15(m, 2H), 2.68-2.57(m, 2H), 1.76-1.58(m, 6H), 1.55(t, 3H), 0.95(t, 3H) |
| 1-4 | 8.04-7.95(m, 2H), 7.82-7.75(m, 1H), 7.51-7.43(m, 2H), 7.20(s, 1H), 3.22(q, 2H), 2.65(t, 2H), 1.71(q, 2H), 1.43-1.20(m, 13H), 1.15(t, 3H), 0.88(t, 3H) |
| 1-7 | 7.98-7.95(m, 1H), 7.94(s, 1H), 7.81-7.78(m, 1H), 7.53(s, 1H), 7.51-7.48(m, 1H), 4.15-4.10(m, 1H), 3.22(q, 2H), 1.26(t, 3H), 1.16-1.13(m, 2H), 0.90-0.82(m, 2H) |
| 1-10 | 7.99(s, 1H), 7.78-7.77(m, 1H), 7.52-7.46(m, 3H), 7.36-7.30(m, 2H), 7.20-7.17(m, 3H), 3.16(q, 2H), 1.54(s, 9H), 1.11(t, 3H) |
| 1-12 | 8.02-7.94(m, 2H), 7.81-7.74(m, 1H), 7.51-7.45(m, 2H), 7.36(s, 1H), 7.29-7.20(m, 1H), 7.14-7.12(m, 3H), 3.21-3.10(m, 4H), 2.95(t, 2H), 1.11(t, 3H) |

TABLE 16-continued

| Compound No. | $^1$H-NMR data ($CDCl_3$) |
|---|---|
| 1-14 | 8.01-7.95(m, 2H), 7.80-7.74(m, 1H),, 7.51-7.44(m, 2H), 7.33-7.21(m, 3H), 7.21-7.15(m, 1H), 7.13(s, 1H), 3.17-2.94(m, 6H), 1.10(t, 3H) |
| 1-15 | 8.22(s, 1H), 7.61-7.43(m, 2H), 7.40-7.07(m, 9H), 4.06(s, 2H), 3.22(q, 2H), 1.43(t, 3H) |
| 1-18 | 8.03(d, 1H), 8.01-7.98(m, 1H), 7.85-7.80(m, 1H), 7.71(d, 1H), 7.58-7.55(m, 2H), 7.53-7.49(m, 2H), 7.36-7.34(m, 3H), 3.25(q, 2H), 1.17(t, 3H) |
| 1-25 | 8.11(s, 1H), 8.00-7.95(m, 1H), 7.86-7.79(m, 2H), 7.58-7.50(m, 2H), 3.17(dt, 2H), 1.60(sextet, 2H), 0.93(t, 3H) |
| 1-31 | 8.27(s, 1H), 8.00(s, 1H), 7.99-7.97(m, 1H), 7.85-7.80(m, 1H), 7.60-7.54(m, 2H), 3.29(q, 2H), 1.27(t, 3H) |
| 1-32 | 8.03(s, 1H), 8.01-7.97(m, 1H), 7.82-7.80(m, 1H), 7.52-7.49(m, 3H), 4.73(s, 2H), 4.08(t, 2H), 3.21(q, 2H), 1.16(t, 3H) |

TABLE 17

| Compound No. | $^1$H-NMR data ($CDCl_3$) |
|---|---|
| 1-33 | 8.04(d, 1H), 8.02(d, 1H), 8.01-7.95(m, 1H), 7.85-7.78(m, 1H), 7.56-7.50(m, 2H), 7.50-7.45(m, 2H), 7.38-7.31(m, 2H), 7.28-7.23(m, 1H), 3.25(q, 2H), 1.94(s, 6H), 1.17(t, 3H) |
| 1-36 | 8.05(d, 1H), 8.04(d, 1H), 8.01-7.96(m, 1H), 7.85-7.79(m, 1H), 7.55-7.50(m, 2H), 7.50-7.45(m, 2H), 7.38-7.31(m, 2H), 7.28-7.23(m, 1H), 3.25(q, 2H), 1.94(s, 6H), 1.17(t, 3H) |
| 1-39 | 8.30(d, 1H), 8.14(d, 1H), 8.01-7.97(m, 1H), 7.86-7.82(m, 1H), 7.59-7.51(m, 2H), 6.09-6.01(m, 1H), 3.32(q, 2H), 1.17(t, 3H) |

TABLE 17-continued

| Compound No. | $^1$H-NMR data ($CDCl_3$) |
|---|---|
| 1-40 | 8.02(d, 1H), 8.01-7.97(m, 1H), 7.85-7.79(m, 1H), 7.56-7.48(m, 2H), 7.32-7.18(m, 5H), 3.29-3.20(m, 4H), 1.17(t, 3H) |
| 1-41 | 8.03(d, 1H), 8.01-7.96(m, 2H), 7.85-7.80(m, 1H), 7.56-7.48(m, 2H), 7.34-7.12(m, 5H), 3.25(q, 2H), 2.78-2.66(m, 2H), 2.29-2.21(m, 2H), 1.17(t, 3H) |
| 1-42 | 8.30(d, 1H), 8.13(d, 1H), 8.02-7.97(m, 1H), 7.87-7.82(m, 1H), 7.58-7.50(m, 2H), 7.38-7.14(m, 4H), 3.42(q, 2H), 2.09(s, 3H), 1.17(t, 3H) |
| 1-45 | 7.99-7.95(m, 2H), 7.91(d, 1H), 7.85-7.80(m, 1H), 7.53-7.49(m, 2H), 3.26(q, 2H), 1.50(s, 9H), 1.19(t, 3H) |
| 1-46 | 8.02(d, 1H), 7.98-7.93(m, 2H), 7.83-7.79(m, 1H), 7.53-7.49(m, 2H), 7.24-7.15(m, 5H), 3.21(q, 2H), 1.84(s, 6H), 1.15(t, 3H) |

TABLE 18

| Compound No. | $^1$H-NMR data (CDCl$_3$) |
| --- | --- |
| 2-3 | 7.94(dd, 1H), 7.91(d, 1H), 7.73(dd, 1H), 7.70(d, 1H), 7.40(dd, 2H), 7.33-7.11(m, 5H), 4.30-4.25(m, 2H), 3.62-3.56(m, 2H), 3.44(q, 2H), 1.19(t, 3H) |
| 2-5 | 7.95-7.93(m, 1H), 7.85(s, 1H), 7.77-7.74(m, 1H), 7.46-7.44(m, 2H), 7.14-7.12(m, 2H), 7.01-6.97(m, 2H), 4.12(q, 2H), 2.93(s, 4H), 1.58(t, 3H) |
| 2-6 | 7.95-7.93(m, 1H), 7.86(s, 1H), 7.76-7.74(m, 1H), 7.45-7.43(m, 2H), 7.11(d, 2H), 6.85(d, 2H), 4.14(q, 2H), 3.79(s, 3H), 2.91(s, 4H), 1.58(t, 3H) |
| 2-10 | 8.22(dd, 1H), 7.99-7.92(m, 1H), 7.82-7.76(m, 1H), 7.46(ddd, 2H), 6.82(d, 1H), 4.05(q, 2H), 1.57(t, 3H) |
| 2-11 | 8.51(s, 1H), 8.12(s, 1H), 7.98-7.92(m, 1H), 7.80-7.74(m, 1H), 7.48-7.41(m, 2H), 4.12(q, 2H), 1.58(s, 9H), 1.57(t, 3H) |
| 2-17 | 7.99-7.94(m, 1H), 7.86-7.80(m, 1H), 7.53-7.43(m, 2H), 6.52(s, 1H), 3.94(q, 2H), 2.47(s, 3H), 1.51(t, 3H) |
| 2-19 | 8.00(s, 1H), 7.97-7.92(m, 1H), 7.80-7.74(m, 1H), 7.45-7.43(m, 2H), 4.14(q, 2H), 2.68(q, 2H), 1.59(t, 3H), 1.31(t, 3H) |
| 2-20 | 7.95-7.92(m, 1H), 7.80(s, 1H), 7.80-7.73(m, 1H), 7.45-7.42(m, 2H), 4.13(q, 2H), 1.89-1.82(m, 1H), 1.59(t, 3H), 1.02-0.97(m, 2H), 0.69-0.65(m, 2H) |
| 2-22 | 8.18(d, 1H), 7.98-7.89(m, 1H), 7.76-7.69(m, 2H), 7.49-7.40(m, 3H), 7.37-7.30(m, 3H), 6.80(d, 1H), 3.99(s, 2H), 3.14(q, 2H), 1.43(t, 3H) |
| 2-24 | 8.39(s, 1H), 7.98-7.93(m, 1H), 7.81-7.76(m, 1H), 7.51-7.44(m, 3H), 6.34(d,1H), 4.11(q, 2H), 1.58(t,3H), 1.54(s, 9H) |
| 2-25 | 8.65(s, 1H), 7.97-7.95(m, 1H), 7.81-7.79(m, 1H), 7.51-7.48(m, 3H), 4.11(q, 2H), 2.58(s, 3H), 1.59(t, 3H) |
| 2-27 | 8.62(d, 1H), 7.95(dd, 1H), 7.80(dd, 1H), 7.53-7.42(m, 2H), 4.10(q, 2H), 1.61-1.55(12H) |
| 2-30 | 7.73-7.68(m, 1H), 7.58(m, 1H), 7.49(s, 1H), 7.36-7.32(m, 2H), 4.32(q, 2H), 3.70(s, 3H), 3.38(s, 3H), 1.27(t, 3H) |
| 2-31 | 8.88(s, 1H), 7.97-7.92(m, 1H), 7.60-7.54(m, 1H), 7.39-7.32(m, 2H), 4.31(q, 2H), 1.59(s, 9H), 1.43(t, 3H) |

TABLE 19

| Compound No. | $^1$H-NMR data (CDCl$_3$) |
| --- | --- |
| 2-32 | 8.17(s, 1H), 7.96-7.93(m, 1H), 7.80-7.77(m, 1H), 7.50-7.45(m, 2H), 4.07(q, 2H), 3.25-3.18(m, 1H), 1.57(t, 3H), 1.32(s, 3H), 1.29(s, 3H) |
| 2-34 | 8.09(s, 1H), 7.96-7.90(m, 1H), 7.78-7.73(m, 1H), 7.48-7.41(m, 2H), 4.07(q, 2H), 1.57(t, 3H) |
| 2-36 | 8.13(dd, 1H), 7.97-7.94(m, 1H), 7.78-7.74(m, 1H), 7.68(d, 1H), 7.45-7.42(m, 2H), 6.75(dd, 2H), 6.51(d, 1H), 4.28(q, 2H), 4.16(q, 2H), 1.59(t, 3H), 1.36(t, 3H) |
| 2-44 | 8.18(s, 1H), 7.96-7.91(m, 1H), 7.78-7.73(m, 1H), 7.48-7.41(m, 2H), 4.27(q, 2H), 1.60(t, 3H) |
| 2-46 | 8.17(d, 1H), 7.97-7.93(m, 3H), 7.78-7.75(m, 1H), 7.55-7.52(m, 1H), 7.48-7.44(m, 2H), 6.99(d, 1H), 3.94(q, 2H), 1.52(t, 3H) |
| 2-51 | 8.54(s, 1H), 7.97-7.93(m, 1H), 7.78-7.74(m, 1H), 7.38-7.33(m, 2H), 7.13(s, 1H), 4.17(q, 2H), 1.59(t, 3H), 1.56(s, 9H) |
| 2-52 | 8.39(s, 1H), 7.95-7.91(m, 1H), 7.79-7.74(m, 1H), 7.47-7.43(m, 2H), 4.74(t, 2H), 3.95(q, 2H), 1.57-1.54(m, 12H) |
| 2-53 | 8.68(d, 1H), 7.96(dd, 1H), 7.80(dd, 1H), 7.48(ddd, 2H), 5.25(sep, 1H), 4.10(q, 2H), 1.59(t, 3H), 1.36(d, 6H) |
| 2-54 | 8.61(d, 1H), 7.96(dd, 1H), 7.79(dd, 1H), 7.48(ddd, 2H), 4.10(q, 2H), 2.45-2.35(m, 6H), 1.61-1.18(m, 8H) |
| 2-55 | 8.51(s, 1H), 7.95-7.93(m, 1H), 7.83-7.81(m, 1H), 7.51-7.48(m, 2H), 3.99(q, 2H), 3.07-3.00(m, 1H), 1.55(t, 3H), 1.41-1.38(m, 2H), 1.27-1.24(m, 3H) |
| 2-56 | 8.61(s, 1H), 7.96-7.94(m, 1H), 7.84-7.82(m, 1H), 7.53-7.51(m, 2H), 3.97(q, 2H), 3.43-3.36(m, 1H), 1.58(t, 3H), 1.42(s, 3H), 1.40(s, 3H) |

TABLE 20

| Compound No. | $^1$H-NMR data (CDCl$_3$) |
| --- | --- |
| 2-59 | 8.45(s,1 H), 7.96-7.93(m, 2H), 7.80-7.79(m, 1H), 7.67-7.65(m, 1H), 7.63-7.45(m, 5H), 3.15(q, 2H), 1.43(t, 3H) |
| 2-74 | 8.38(s, 1H), 7.93-7.91(m, 1H), 7.73-7.71(m, 1H), 7.43-7.41(m, 2H), 4.23(t, 3H), 4.13(q, 2H), 1.90(sextet, 2H), 1.58(t, 3H), 1.48(s, 9H), 1.43(t, 3H) |
| 2-77 | 7.80(d, 1H), 7.52(d, 1H), 7.33-7.27(m, 2H), 7.24-7.17(m, 1H), 6.39-6.11(dt, 1H), 4.84-4.78(dt, 2H), 3.54-3.48(q, 2H), 1.39-1.36(t, 3H) |
| 2-81 | 8.48(s, 1H), 7.96-7.93(m, 1H), 7.79-7.77(m, 1H), 7.48-7.45(m, 2H), 4.15-4.07(m, 4H), 1.60-1.48(m, 3H), 1.40-1.37(t, 3H) |
| 2-82 | 8.42(s, 1H), 8.98-8.91(m, 1H), 7.78-7.73(m, 1H), 7.49-7.40(m, 2H), 4.12(q, 2H), 1.58(s, 9H), 1.42(t, 3H) |
| 2-83 | 8.02(s, 1H), 7.99-7.97(dd, 1H), 7.85-7.83(dd, 1H), 7.50-7.46(m, 2H), 6.78-6.73(d, 1H), 5.88-5.82(dd, 1H), 3.88-3.82(q, 2H), 1.59(s, 9H), 1.44(t, 3H), 1.30-1.24(m, 1H), 0.77-0.75(ddd, 2H), 0.35-0.34(ddd, 2H) |
| 2-84 | 8.03(s, 1H), 7.99-7.96(dd, 1H), 7.84-7.82(d, 1H), 7.49-7.46(m, 2H), 3.99-3.96(q, 2H), 3.52-3.50(dd, 1H), 3.21-3.17(dt, 1H), 3.12-2.85(m, 2H), 1.59(s, 9H), 1.47(t, 3H) |
| 2-85 | 8.47(s, 1H), 7.96-7.91(m, 1H), 7.79-7.70(m, 1H), 7.48-7.39(m, 2H), 4.19(q, 2H), 2.96(dt, 2H), 1.78-1.69(m, 2H), 1.56(s, 9H), 1.42-1.33(m, 4H), 1.30-122(t, 3H), 0.92-0.88(dd, 3H) |
| 2-86 | 8.51(s, 1H), 7.95-7.92(dd, 1H), 7.76-7.75(dd, 1H), 7.33-7.25(m, 2H), 6.7(s, 1H), 4.15(q, 2H), 2.14-2.04(d, 3H), 2.04-1.99(d, 3H), 1.58(s, 9H), 1.57(t, 3H) |
| 2-87 | 8.48(s, 1H), 7.98-7.91(m, 1H), 7.78-7.71(m, 1H), 7.46-7.40(m, 2H), 4.19(q, 2H), 2.88-2.79(m, 2H), 2.20-2.02(m, 1H), 1.57(br, 3H), 1.00(s, 9H), 0.95-0.80(br, 6H) |
| 2-89 | 8.48(s, 1H), 7.94-7.92(dd, 1H), 7.76-7.75(dd, 1H), 7.44-7.42(m, 2H), 7.31-7.27(m, 3H), 7.26-7.19(m, 2H), 4.01(q, 2H), 3.03-3.29(t, 2H), 3.09-3.05(m, 2H), 1.56(s, 9H), 1.49(t, 3H) |
| 2-90 | 8.62(s, 1H), 7.96-7.94(m, 1H), 7.77-7.74(m, 1H), 7.50-7.47(m, 2H), 4.02(q, 2H), 1.58(s, 9H), 1.55(t, 3H) |

TABLE 21

| Compound No. | $^1$H-NMR data (CDCl$_3$) |
| --- | --- |
| 2-91 | 7.95-7.93(m, 1H), 7.80-7.78(m, 1H), 7.45-7.42(m, 2H), 4.19(q, 2H), 2.66(s, 3H), 1.60(s, 9H), 1.53(t, 3H), 1.28(s, 9H) |
| 2-92 | 8.40(s, 1H), 7.97-7.91(m, 1H), 7.76-7.71(m, 1H), 7.46-7.40(m, 2H), 4.94(d, 2H), 4.18(q, 2H), 2.51(t, 1H), 1.59(t, 3H) |
| 2-94 | 8.28(s, 1H), 7.95-7.93(d, 1H), 7.79-7.77(d, 1H), 7.47-7.44(m, 2H), 6.13(br, 1H), 4.59-4.55(q, 2H), 3.59-3.53(q, 2H), 1.59(s, 9H), 1.50-1.45(t, 3H) |
| 2-95 | 8.94(s, 1H), 7.57-7.53(m, 2H), 7.40-7.38(m, 2H), 7.15-7.12(m, 2H), 4.77-4.74(d, 2H) ,3.30-3.10(br, 2H), 2.8(q, 2H), 1.38-1.33(t, 3H) |
| 2-97 | 8.47(s, 1H), 7.69-7.67(dd, 1H), 7.42-7.40(dd, 1H), 7.33-7.31(m, 2H), 5.74(br, 1H), 4.33-4.29(q, 2H), 1.59-1.57(t, 3H), 1.48(s, 9H), 1.46(s, 9H) |
| 2-98 | 7.98-7.90(dd, 1H), 7.73-7.65(dd, 1H), 7.42-7.35(m, 2H), 7.20-7.11(m, 1H), 4.32-4.22(q, 2H), 1.44-1.32(m, 27H) |
| 2-99 | 8.47(s, 1H), 7.95-7.93(dd, 1H), 7.78-7.76(dd, 1H), 7.47-7.44(m, 2H), 4.15-4.12(q, 2H), 1.51(s, 9H), 1.42-1.40(t, 3H) |
| 2-102 | 7.92-7.90(m, 1H), 7.83(s, 1H), 7.71-7.69(m, 1H), 7.41-7.38(m, 2H), 4.60(q, 2H), 4.00(q, 2H), 2.75-2.73(m, 2H), 2.56-2.54(m, 2H), 1.56(t, 3H), 1.46(s, 9H) |
| 2-103 | 7.97(d, 1H), 7.94-7.89(m, 1H), 7.72-7.67(m, 1H), 7.41-7.35(m, 2H), 5.99(d, 1H), 4.23(t, 2H), 4.17(q, 2H), 2.43(t, 2H), 2.13-2.05(m, 2H), 1.57(t, 3H), 1.45(s, 9H) |
| 2-107 | 7.94-7.92(m, 2H), 7.75-7.72(m, 1H), 7.43-7.40(m, 2H), 7.32-7.28(m, 2H), 7.23-7.20(m, 3H), 4.36(q, 2H), 3.14-3.10(m, 2H), 3.00-2.95(m, 2H), 1.61(m, 9H), 1.59(t, 3H) |
| 2-109 | 7.93(s, 1H), 7.78-7.75(m, 1H), 7.48-7.42(m, 3H), 7.34-7.30(m, 2H), 7.28-7.18(m, 3H), 4.07(t, 3H), 3.00(s, 4H), 1.58(t, 3H) |

TABLE 21-continued

| Compound No. | ¹H-NMR data (CDCl₃) |
|---|---|
| 2-111 | 8.61(s, 1H), 7.96-7.94(m, 1H), 7.84-7.82(m, 1H), 7.56-7.48(m, 2H), 3.94(q, 2H), 1.58(t, 3H) |

TABLE 22

| Compound No. | ¹H-NMR data (CDCl₃) |
|---|---|
| 2-113 | 8.44(s, 1H), 7.75-7.73(m, 1H), 7.63(d, 1H), 7.49-7.46(m, 1H), 7.36(m, 2H), 6.41(d, 1H), 4.11(q, 2H), 3.92(s, 2H), 1.58(t, 3H), 0.99(s, 9H) |
| 2-115 | 8.42(s, 1H), 7.96-7.94(m, 1H), 7.80-7.77(m, 1H), 7.65(d, 1H), 7.54-7.33(m, 6H), 6.44(d, 1H), 5.31(s, 2H), 4.12(q, 2H), 1.56(t, 3H) |
| 2-116 | 8.44(s, 1H), 7.96-7.94(m, 1H), 7.79-7.77(m, 1H), 7.63(d, 1H), 7.50-7.44(m, 2H), 6.41(d, 1H), 4.09(q, 2H), 3.82(s, 2H), 2.01(bs, 3H), 1.76-1.57(m, 15H) |
| 2-118 | 8.34(d, 1H), 7.96-7.94(m, 1H), 7.81-7.79(m, 1H), 7.71(t, 1H), 7.57-7.45(m,, 4H), 7.29(t, 1H), 4.07(q, 2H), 1.58(t, 3H) |
| 2-119 | 8.72(s, 1H), 7.72-7.66(m, 1H), 7.43-7.37(m, 1H), 7.33-7.29(m, 2H), 4.08-3.98(q, 2H), 3.35(s, 3H), 2.57(s, 3H), 1.43-1.34(t, 3H) |
| 2-121 | 7.94-7.92(m, 1H), 7.74-7.72(m, 2H), 7.46-7.42(m, 2H), 7.31(d, 1H), 7.13(d, 1H), 4.11(m, 2H), 3.94(q, 2H), 1.56(t, 3H), 1.27(s, 9H) |
| 2-131 | 8.54(s, 1H), 7.96-7.94(dd, 1H), 7.77-7.74(dd, 1H), 7.45-7.43(m, 2H), 4.19-4.13(q, 2H), 3.03(s, 2H), 2.68(s, 2H), 1.59-1.32(t, 3H), 1.08(s, 9H), 1.00(s, 9H) |
| 2-132 | 8.27(s, 1H), 7.95-7.92(m, 1H), 7.80-7.76(m, 1H), 7.51-7.42(m, 2H), 4.89(s, 2H), 4.06(q, 2H), 1.56(t, 3H), 1.25(s, 9H) |
| 2-135 | 8.02(s, 1H), 7.95-7.93(m, 1H), 7.75-7.73(m, 1H), 7.43-7.41(m, 2H), 4.34(q, 2H), 3.09-3.05(m, 2H), 2.61-2.58(m, 2H), 1.62(s, 9H), 1.59(t, 3H), 1.45(s, 9H) |
| 2-136 | 8.39(s, 1H), 7.93-7.90(m, 1H), 7.74-7.72(m, 1H), 7.44-7.41(m, 2H), 4.13(q, 2H), 2.89(s, 6H), 1.38(t, 3H) |
| 2-139 | 8.19(s, 1H), 7.94-7.92(m, 1H), 7.78-7.76(m, 1H), 7.47-7.45(m, 2H), 7.06(t, 1H), 4.04(q, 2H), 1.70(s, 9H), 1.55(t, 3H) |
| 2-140 | 8.50(s, 1H), 7.96-7.94(m, 1H), 7.78-7.76(m, 1H), 7.48-7.44(m, 2H), 4.10(q, 2H), 2.97(t, 2H), 2.06(t, 2H), 1.58(s, 6H), 1.55(t, 3H) |

TABLE 23

| Compound No. | ¹H-NMR data (CDCl₃) |
|---|---|
| 2-141 | 8.25(s, 1H), 7.98-7.91(m, 1H), 7.84(s, 1H), 7.79-7.74(m, 1H), 7.48-7.41(m, 2H), 3.41-3.21(m, 4H), 1.55(t, 3H) |
| 2-142 | 8.73(s, 1H), 7.74-7.72(d, 1H), 7.57-7.54(d, 1H), 7.33-7.30(m, 2H), 4.15-4.11(q, 2H), 2.92-2.88(d, 2H), 2.69-2.68(d, 2H), 2.66-2.55(m, 1H), 2.43-2.32(m, 1H), 1.41-1.39( t, 3H), 1.37-1.30(m, 12H), 0.90(s, 9H) |
| 2-143 | 8.61(s, 1H), 8.18-8.14(d, 1H), 7.99-7.91(d, 1H), 7.77-7.69(m, 1H), 7.47-7.41(m, 2H), 6.82-6.78(d, 1H), 4.39-4.30(q, 2H), 4.30-4.28(q, 2H), 1.60-1.58(t, 3H), 1.41-1.38(t, 3H), 1.37-1.34(t, 3H) |
| 2-144 | 8.54(s, 1H), 8.42-8.02(d, 1H), 7.99-7.91(m, 1H), 7.78-7.70(m, 1H), 7.48-7.44(m, 2H), 6.68-6.64(d, 1H), 4.15-4.11(q, 2H), 1.60(s, 9H), 1.55(s, 9H), 1.44-1.38(t, 3H) |
| 2-145 | 8.47(s, 1H), 7.96-7.90(d, 1H), 7.78-7.72(d, 1H), 7.45-7.43(m, 2H), 4.16-4.11(q, 2H), 1.59(s, 9H), 1.55(s, 9H), 1.41-1.34(t, 3H) |
| 2-146 | 8.10(s, 1H), 7.94-7.91(m, 1H), 7.73-7.71(m, 1H), 7.42-7.39(m, 2H), 4.13(m, 2H), 2.35(s, 3H), 1.55(t, 3H) |
| 2-148 | 8.55(s, 1H), 7.95-7.93(m, 1H), 7.75-7.72(m, 1H), 7.44-7.42(m, 2H), 4.36-4.31(m, 2H), 4.17-4.12(m, 2H), 3.54-3.50(q, 2H), 3.32-3.29(s, 2H), 2.80-2.76(t, 2H), 1.48-1.21(m, 9H) |

TABLE 23-continued

| Compound No. | ¹H-NMR data (CDCl₃) |
|---|---|
| 2-149 | 7.70-7.62(m, 1H), 7.42-7.32(m, 1H), 7.32-7.30(m, 2H), 5.55(s, 1H), 4.13-4.11(q, 2H), 3.55-3.52(q, 2H), 3.13-3.02(m, 1H), 2.86-2.84(m, 1H), 1.42-1.24(m, 9H) |
| 2-150 | 8.37(d, 1H), 7.99-7.93(m, 1H), 7.92(s, 1H), 7.81-7.75(m, 1H), 7.49-7.42(m, 2H), 4.08(q, 2H), 1.55(t, 3H) |
| 2-155 | 8.16(s, 1H), 7.91-7.89(m, 1H), 7.72-7.70(m, 1H), 7.43-7.41(m, 2H), 7.11(d, 1H), 6.91(t, 1H), 6.40(d, 1H), 4.02(q, 2H), 1.59(s, 9H), 1.53(t, 3H) |
| 2-156 | 7.93-7.91(m, 1H), 7.88(s, 1H), 7.70-7.68(m, 1H), 7.42-7.40(m, 2H), 6.84(t, 1H), 4.13(q, 2H), 2.77(t, 2H), 2.55(t, 2H), 1.57(t, 3H), 1.45(s, 9H) |
| 2-157 | 8.04(s, 1H), 7.90-7.88(m, 1H), 7.72-7.70(m, 1H), 7.43-7.41(m, 2H), 6.86(t, 1H), 4.03(q, 2H), 1.55(t, 3H), 1.33(s, 9H) |
| 2-158 | 7.91-7.89(m, 1H), 7.85(s, 1H), 7.72-7.70(m, 1H), 7.41-7.39(m, 2H), 4.09(q, 2H), 2.45-2.41(m, 2H), 1.58-1.52(m, 5H), 0.96(s, 9H) |

TABLE 24

| Compound No. | ¹H-NMR data (CDCl₃) |
|---|---|
| 2-160 | 8.00(s, 1H), 7.95-7.93(m, 1H), 7.74-7.72(m, 1H), 7.43-7.40(m, 2H), 4.37(q, 2H), 3.22(s, 3H), 2.85-2.81(m, 2H), 1.86-1.82(m, 2H), 1.60(s, 9H), 1.12(s, 6H) |
| 2-161 | 8.50(s, 1H), 7.98-7.96(m, 1H), 7.81-7.79(m, 1H), 7.50-7.48(m, 2H), 4.14(q, 2H), 2.94(t, 2H), 2.09(t, 2H), 1.76-1.71(m, 2H), 1.66-1.61(m, 2H), 1.55(t, 3H), 0.88(t, 6H) |
| 2-162 | 7.93-7.90(m, 1H), 7.85(s, 1H), 7.70-7.68(m, 1H), 7.38-7.35(m, 2H), 4.23(q, 2H), 2.42-2.38(m, 2H), 2.28(s, 3H), 1.57-1.48(m, 5H), 0.96(s, 9H) |
| 2-163 | 8.13(s, 1H), 7.96-7.93(m, 1H), 7.81-7.78(m, 1H), 7.47-6.97(m, 7H), 4.94(s, 2H), 4.11(q, 2H), 2.34(s, 3H), 1.54(t, 3H) |
| 2-166 | 7.93-7.90(m, 1H), 7.86(s, 1H), 7.70-7.68(m, 1H), 7.38-7.36(m, 2H), 4.23(q, 2H), 3.22(s, 3H), 2.50-2.45(m, 2H), 2.29(s, 3H), 1.82-1.77(m, 2H), 1.56(t, 3H), 1.22(s, 6H) |
| 2-167 | 8.44(s, 1H), 7.98-7.91(m, 1H), 7.74-7.71(m, 1H), 7.43-7.68(m, 2H), 4.29-4.22(q, 2H), 3.28-3.23(t, 2H), 7.68-7.63(t, 2H), 1.73-1.68(t, 3H), 1.58(s, 9H), 1.42(s, 9H) |
| 2-168 | 8.49(s, 1H), 7.95-7.93(dd, 1H), 7.78-7.76(dd, 1H), 7.47-7.45(m, 2H), 4.16-4.10(q, 2H), 3.49(s, 3H), 1.61-1.59(t, 3H), 1.57(s, 9H), 1.55(s, 6H) |
| 2-169 | 8.49(s, 1H), 7.95-7.93(dd, 1H), 7.78-7.76(dd, 1H), 7.47-7.45(m, 2H), 4.16-4.10(q, 2H), 3.49(s, 3H), 1.61-1.59(t, 3H), 1.57(s, 9H), 1.55(s, 6H) |
| 3-1 | 8.79(s, 1H), 8.00-7.94(m, 1H), 7.87-7.80(m, 1H), 7.57-7.47(m, 2H), 3.97(q, 2H), 1.55(t, 3H) |
| 3-2 | 8.82(s, 1H), 8.00-7.94(m, 1H), 7.87-7.81(m, 1H), 7.57-7.47(m, 2H), 3.95(q, 2H), 1.56(t, 3H) |
| 3-3 | 8.63(s, 1H), 7.98-7.92(m, 1H), 7.82-7.76(m, 1H), 7.50-7.42(m, 2H), 7.33-7.15(m, 5H), 3.85(q, 2H), 3.22-3.14(m, 4H), 1.45(t, 3H) |
| 7-1 | 8.01-7.98(m, 1H), 7.78-7.76(m, 1H), 7.49-7.45(m, 2H), 7.19-7.18(m, 1H), 6.74-6.73(m, 1H), 3.18(q, 2H), 1.14(t, 3H) |
| 7-6 | 7.88-7.86(m, 1H), 7.51-7.48(m, 1H), 7.76(s, 2H), 7.34-7.32(m, 2H), 4.31-4.27(q, 2H), 3.82(s, 6H), 1.21-1.19(t, 3H) |

[Formula 16]

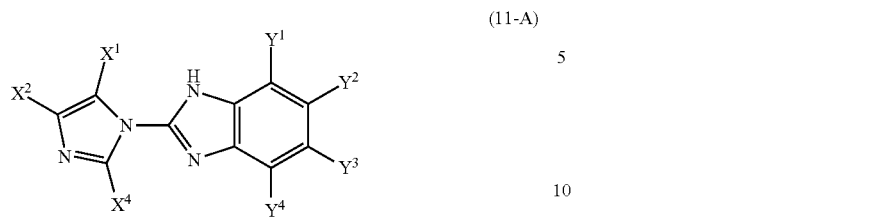

(11-A)

TABLE 25

| Intermediate No. | $X^1$ | $X^2$ | $X^4$ | $Y^1$ | $Y^2$ | $Y^3$ | $Y^4$ | Physical property |
|---|---|---|---|---|---|---|---|---|
| 11-1 | H | H | H | H | H | H | H | 192-194 |
| 11-2 | H | n-$C_5H_{11}$ | H | H | H | H | H | NMR |
| 11-3 | H | n-$C_8H_{17}$ | H | H | H | H | H | 1.602(25.8) |
| 11-4 | H | t-Bu | H | H | H | H | H | NMR |
| 11-5 | H | n-$C_6H_{13}$CH=CH (Z) | H | H | H | H | H | 1.533(24.8) |
| 11-6 | H | c-PrC≡C | H | H | H | H | H |  |
| 11-7 | H | $PhCH_2$ | H | H | H | H | H | NMR |
| 11-8 | H | $PhCH_2CH_2$ | H | H | H | H | H | NMR |
| 11-9 | H | 4-(t-Bu)$PhCH_2CH_2$ | H | H | H | H | H |  |
| 11-10 | H | 4-$CF_3PhCH_2CH_2$ | H | H | H | H | H |  |
| 11-11 | H | 4-$ClPhCH_2CH_2$ | H | H | H | H | H | NMR |
| 11-12 | H | 2,4-$Cl_2PhCH_2CH_2$ | H | H | H | H | H | NMR |
| 11-13 | H | 4-$BrPhCH_2CH_2$ | H | H | H | H | H | NMR |
| 11-14 | H | $PhOCH_2$ | H | H | H | H | H | NMR |
| 11-15 | H | 4-$CF_3PhOCH_2$ | H | H | H | H | H | NMR |
| 11-16 | H | 4-$CF_3OPhOCH_2$ | H | H | H | H | H | NMR |
| 11-17 | H | PhC≡C | H | H | H | H | H | 147-148 |
| 11-18 | H | Br | H | H | H | H | H | 152-153 |
| 11-19 | H | I | H | H | H | H | H | NMR |
| 11-20 | H | $CF_3$ | H | H | H | H | H | 1.588(26.0) |
| 11-21 | H | $(CF_3)_2CF$ | H | H | H | H | H | 207-208 |
| 11-22 | H | $(CF_3)_2CF$ | H | H | Br | Br | H | NMR |
| 11-23 | H | n-$C_4F_9$ | H | H | H | H | H | NMR |
| 11-24 | H | n-$C_6F_{13}$ | H | H | H | H | H | NMR |
| 11-25 | H | $CO_2Et$ | H | H | H | H | H | 158-159 |
| 11-26 | H | CONHPh | H | H | H | H | H | 248-249 |

TABLE 26

| Intermediate No. | $X^1$ | $X^2$ | $X^4$ | $Y^1$ | $Y^2$ | $Y^3$ | $Y^4$ | Physical property |
|---|---|---|---|---|---|---|---|---|
| 11-27 | H | CN | H | H | H | H | H |  |
| 11-28 | H | n-$C_3F_7CH_2OCH_2$ | H | H | H | H | H |  |
| 11-29 | H | $CO_2$(t-Bu) | H | H | H | H | H |  |
| 11-30 | H | $CO_2$(t-Amyl) | H | H | H | H | H |  |
| 11-31 | H | $CO_2(CMe_2C≡CH)$ | H | H | H | H | H |  |
| 11-32 | H | $CO_2(CMe_2Ph)$ | H | H | H | H | H | NMR |
| 11-33 | H | $CO_2(2,6-Me_2Ph)$ | H | H | H | H | H | 249-250 |
| 11-34 | H | $(CF_3)_2CF$ | H | H | Me | Me | H | 131-133 |
| 11-35 | H | $CO_2CH(CF_3)_2$ | H | H | H | H | H | NMR |
| 11-36 | H | $CO_2(CMe_2CH_2Ph)$ | H | H | H | H | H | 290-291 |
| 11-37 | H | $CO_2(CMe_2CH_2CH_2Ph)$ | H | H | H | H | H |  |
| 11-38 | H | $CO_2$(2-MePh) | H | H | H | H | H | 278-281 |
| 11-39 | H | CH=$CHCO_2CH$(t-Bu) (E) | H | H | H | H | H | 239-240 |
| 11-40 | H | CH=$CHCO_2CH(CF_3)_2$ (E) | H | H | H | H | H | 228-230 |
| 11-41 | H | CONHt-Bu | H | H | H | H | H | 286-288 |
| 11-42 | H | $CONHC(Me)_2Ph$ | H | H | H | H | H | 239-240 |

[Formula 17]

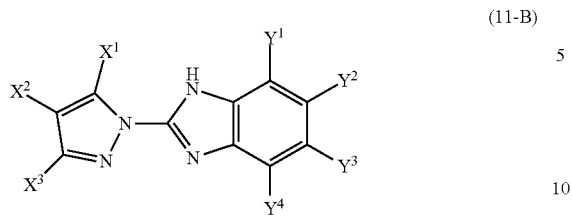

(11-B)

TABLE 27

| Intermediate No. | X$^1$ | X$^2$ | X$^3$ | Y$^1$ | Y$^2$ | Y$^3$ | Y$^4$ | Physical property |
|---|---|---|---|---|---|---|---|---|
| 12-1 | H | H | H | H | H | H | H | 233-234 |
| 12-2 | H | n-C$_8$H$_{17}$ | H | H | H | H | H | 185-186 |
| 12-3 | H | PhCH$_2$CH$_2$ | H | H | H | H | H | 113-114 |
| 12-4 | H | 4-CF$_3$PhCH$_2$CH$_2$ | H | H | H | H | H | 138-139 |
| 12-5 | H | 4-FPhCH$_2$CH$_2$ | CF$_3$ | H | H | H | H | NMR |
| 12-6 | H | 4-MeOPhCH$_2$CH$_2$ | CF$_3$ | H | H | H | H | NMR |
| 12-7 | H | n-C$_6$H$_{13}$C≡C | H | H | H | H | H | 156-157 |
| 12-8 | H | 4-CF$_3$PhC≡C | H | H | H | H | H | 156-157 |
| 12-9 | H | 4-FPhC≡C | CF$_3$ | H | H | H | H | NMR |
| 12-10 | H | (CF$_3$)$_2$CF | H | H | H | H | H | 132-133 |
| 12-11 | H | CO$_2$(t-Bu) | H | H | H | H | H |  |
| 12-12 | H | H | CF$_3$ | H | H | H | H | 188-189 |
| 12-13 | H | Cl | CF$_3$ | H | H | H | H | 228-231 |
| 12-14 | H | Br | CF$_3$ | H | H | H | H | 198-199 |
| 12-15 | H | I | CF$_3$ | H | H | H | H | 211-212 |
| 12-16 | Me | H | CF$_3$ | H | H | H | H | 171-172 |
| 12-17 | Me | Br | CF$_3$ | H | H | H | H | 161-163 |
| 12-18 | H | Et | CF$_3$ | H | H | H | H | NMR |
| 12-19 | H | c-Pr | CF$_3$ | H | H | H | H | 171-172 |
| 12-20 | H | CH=CH$_2$ | CF$_3$ | H | H | H | H | NMR |
| 12-21 | H | PhCH$_2$ | CF$_3$ | H | H | H | H | 110-111 |
| 12-22 | H | PhCH$_2$CH$_2$ | CF$_3$ | H | H | H | H | 207-208 |
| 12-23 | H | CH=CHCO$_2$(t-Bu) (E) | CF$_3$ | H | H | H | H |  |
| 12-24 | H | COCH$_3$ | CF$_3$ | H | H | H | H | 217-221 |
| 12-25 | H | CO$_2$Et | CF$_3$ | H | H | H | H | 188-189 |
| 12-26 | H | CO$_2$(t-Bu) | CF$_3$ | H | H | H | H | 1.601(25.0) |
| 12-27 | H | CO$_2$CH$_2$(t-Bu) | CF$_3$ | H | H | H | H | 115-116 |
| 12-28 | H | CO$_2$(2,6-Me$_2$Ph) | CF$_3$ | H | H | H | H | 140-141 |
| 12-29 | H | CONMe(OMe) | CF$_3$ | H | H | H | H | NMR |
| 12-30 | H | COS(t-Bu) | CF$_3$ | H | H | H | H | NMR |

TABLE 28

| Intermediate No. | X$^1$ | X$^2$ | X$^3$ | Y$^1$ | Y$^2$ | Y$^3$ | Y$^4$ | Physical property |
|---|---|---|---|---|---|---|---|---|
| 12-31 | H | i-PrS | CF$_3$ | H | H | H | H | 162-163 |
| 12-32 | H | CO$_2$Et | CHF$_2$ | H | H | H | H | 157-158 |
| 12-33 | H | Br | Br | H | H | H | H | 201-204 |
| 12-34 | H | I | Br | H | H | H | H | 216-217 |
| 12-35 | H | H | CH=CHCO$_2$Et (E) | H | H | H | H |  |
| 12-36 | H | Br | n-BuO | H | H | H | H | 195-195 |
| 12-37 | H | H | CF$_3$CF$_2$CH$_2$O | H | H | H | H | 208-209 |
| 12-38 | H | Cl | CF$_3$CF$_2$CH$_2$O | H | H | H | H | 162-163 |
| 12-39 | H | Br | CF$_3$CF$_2$CH$_2$O | H | H | H | H | 176-177 |
| 12-40 | H | CO$_2$Et | CF$_3$CF$_2$CH$_2$O | H | H | H | H | NMR |
| 12-41 | H | Br | CHF$_2$O | H | H | H | H | 197-198 |
| 12-42 | H | H | CO$_2$(t-Bu) | H | H | H | H | NMR |
| 12-43 | H | Cl | CO$_2$(t-Bu) | H | H | H | H | NMR |
| 12-44 | H | Br | CO$_2$(t-Bu) | H | H | H | H |  |
| 12-45 | H | H | 4-ClPhSO$_2$ | H | H | H | H | 201-203 |
| 12-46 | H | CO$_2$(t-Bu) | Cl | H | H | H | H | NMR |
| 12-47 | H | CO$_2$(t-Bu) | Br | H | H | H | H | NMR |
| 12-48 | H | CO$_2$(t-Bu) | Et | H | H | H | H | NMR |
| 12-49 | H | CO$_2$(t-Bu) | c-Pr | H | H | H | H | NMR |
| 12-50 | H | CO$_2$(t-Bu) | CHF$_2$ | H | H | H | H | 182-183 |

TABLE 28-continued

| Intermediate No. | X¹ | X² | X³ | Y¹ | Y² | Y³ | Y⁴ | Physical property |
|---|---|---|---|---|---|---|---|---|
| 12-51 | H | CO₂(t-Bu) | CF₃CF₂CH₂O | H | H | H | H | NMR |
| 12-52 | H | CO₂(i-Pr) | CF₃ | H | H | H | H | NMR |
| 12-53 | H | CO₂(t-Amyl) | CF₃ | H | H | H | H | 65-66 |
| 12-54 | H | i-PrSO | CF₃ | H | H | H | H | NMR |
| 12-55 | H | i-PrSO₂ | CF₃ | H | H | H | H | NMR |

TABLE 29

| Intermediate No. | X¹ | X² | X³ | Y¹ | Y² | Y³ | Y⁴ | Physical property |
|---|---|---|---|---|---|---|---|---|
| 12-56 | H | CO₂(t-Bu) | i-Pr | H | H | H | H | |
| 12-57 | H | CO₂(t-Bu) | t-Bu | H | H | H | H | |
| 12-58 | H | COPh | CF₃ | H | H | H | H | |
| 12-59 | H | PhCH₂CH₂ | CHF₂ | H | H | H | H | |
| 12-60 | H | CH₂CH₂CO₂(t-Bu) | CF₃ | H | H | H | H | 122-125 |
| 12-61 | H | CO₂(t-Bu) | CO₂(t-Bu) | H | H | H | H | |
| 12-62 | H | H | OCH₂CO₂(t-Bu) | H | H | H | H | |
| 12-63 | H | H | OCH₂CH₂CO₂(t-Bu) | H | H | H | H | |
| 12-64 | H | H | CF₃ | H | Me | Me | H | |
| 12-65 | H | H | CF₃ | H | Cl | H | CF₃ | |
| 12-66 | H | H | CF₃ | H | CF₃ | H | Cl | |
| 12-67 | H | CO₂(t-Bu) | H | H | Me | Me | H | |
| 12-68 | H | CO₂(t-Bu) | H | H | Cl | H | CF₃ | |
| 12-69 | H | CO₂(t-Bu) | H | H | CF₃ | H | Cl | |
| 12-70 | H | CO₂(t-Bu) | Me | H | H | H | H | |
| 12-71 | H | CO₂(t-Bu) | n-Pr | H | H | H | H | 186-188 |
| 12-72 | H | CO₂(t-Bu) | EtO | H | H | H | H | 163-164 |
| 12-73 | H | CO₂(t-Bu) | n-PrO | H | H | H | H | 159-160 |
| 12-74 | H | CO₂(t-Bu) | n-BuO | H | H | H | H | |
| 12-75 | H | CO₂(t-Bu) | CF₃CH₂O | H | H | H | H | NMR |
| 12-76 | H | CO₂(t-Bu) | CHF₂CH₂O | H | H | H | H | NMR |
| 12-77 | H | CO₂(t-Bu) | CHF₂CF₂CH₂O | H | H | H | H | NMR |

TABLE 30

| Intermediate No. | X¹ | X² | X³ | Y¹ | Y² | Y³ | Y⁴ | Physical property |
|---|---|---|---|---|---|---|---|---|
| 12-78 | H | CO₂Me | t-Bu | H | H | H | H | NMR |
| 12-79 | H | CO₂Et | CH=CHc-Pr (E) | H | H | H | H | 213-214 |
| 12-80 | H | CO₂Et | I | H | H | H | H | NMR |
| 12-81 | H | CO₂(t-Bu) | I | H | H | H | H | NMR |
| 12-82 | H | CO₂(t-Bu) | CH=CHc-Pr (E) | H | H | H | H | NMR |
| 12-83 | H | CO₂(t-Bu) | CH₂CH₂c-Pr | H | H | H | H | NMR |
| 12-84 | H | CO₂(t-Bu) | n-C₅H₁₁ | H | H | H | H | 180-182 |
| 12-85 | H | CO₂(t-Bu) | CH=CMe₂ | H | H | H | H | NMR |
| 12-86 | H | CO₂(t-Bu) | i-Bu | H | H | H | H | NMR |
| 12-87 | H | CO₂(t-Bu) | PhC≡C | H | H | H | H | 91-93 |
| 12-88 | H | CO₂(t-Bu) | PhCH₂CH₂ | H | H | H | H | NMR |
| 12-89 | H | CO₂(t-Bu) | C₂F₅ | H | H | H | H | 171-174 |
| 12-90 | Me | CO₂(t-Bu) | t-BuOCH₂ | H | H | H | H | 151-152 |
| 12-91 | H | CO₂(t-Bu) | HC≡CCH₂O | H | H | H | H | NMR |
| 12-92 | H | CO₂CH(CF₃)₂ | H | H | H | H | H | 222-223 |
| 12-93 | H | CONHCH₂CF₃ | t-Bu | H | H | H | H | NMR |
| 12-94 | H | CONHCH₂CF₃ | CONHCH₂CF₃ | H | H | H | H | NMR |
| 12-95 | H | CONH(c-Pr) | t-Bu | H | H | H | H | NMR |
| 12-96 | H | CONH(t-Bu) | t-Bu | H | H | H | H | NMR |
| 12-97 | H | CONMe(t-Bu) | CONMe(t-Bu) | H | H | H | H | NMR |
| 12-98 | H | CN | t-Bu | H | H | H | H | NMR |
| 12-99 | H | PhC≡C | CF₃CH₂O | H | H | H | H | 161-164 |
| 12-100 | H | PhCH₂CH₂ | CF₃CH₂O | H | H | H | H | 166-168 |
| 12-101 | H | CH₂CH₂CO₂(t-Bu) | CF₃CH₂O | H | H | H | H | 94-96 |
| 12-102 | H | H | OCH₂CH₂CH₂CO₂(t-Bu) | H | H | H | H | NMR |

TABLE 31

| Intermediate No. | $X^1$ | $X^2$ | $X^3$ | $Y^1$ | $Y^2$ | $Y^3$ | $Y^4$ | Physical property |
|---|---|---|---|---|---|---|---|---|
| 12-103 | H | I | $CO_2$(t-Bu) | H | H | H | H | 195-197 |
| 12-104 | H | c-Pr | $CO_2$(t-Bu) | H | H | H | H | 210-212 |
| 12-105 | H | PhC≡C | $CO_2$(t-Bu) | H | H | H | H | 219-220 |
| 12-106 | H | $PhCH_2CH_2$ | $CO_2$(t-Bu) | H | H | H | H | 169-171 |
| 12-107 | H | CN | $CO_2$(t-Bu) | H | H | H | H | 214-216 |
| 12-108 | H | $PhCH_2CH_2$ | CN | H | H | H | H | 184-186 |
| 12-109 | H | HC≡C | $CF_3$ | H | H | H | H | 187-190 |
| 12-110 | H | CN | $C_2F_5$ | H | H | H | H | 157-160 |
| 12-111 | H | CH=CHCO$_2$CH(CF$_3$)$_2$ (E) | $CF_3$ | H | H | H | H | 164-165 |
| 12-112 | H | CH=CHCO$_2$CH$_2$(t-Bu) (E) | $CF_3$ | H | H | H | H | NMR |
| 12-113 | H | CH=CHCO$_2$CH$_2$(4-t-Bu)Ph (E) | $CF_3$ | H | H | H | H | NMR |
| 12-114 | H | CH=CHCO$_2$CH$_2$(4-CF$_3$)Ph (E) | $CF_3$ | H | H | H | H | 206-208 |
| 12-115 | H | CH=CHCO$_2$CH$_2$(1-Ad) (E) | $CF_3$ | H | H | H | H | 229-230 |
| 12-116 | H | CH=CHCONHCH$_2$CF$_3$ (E) | $CF_3$ | H | H | H | H | 183-186 |
| 12-117 | H | (2-Py)C≡C | $CF_3$ | H | H | H | H | 237-240 |
| 12-118 | H | Ac | Me | H | H | H | H | NMR |
| 12-119 | H | $SO_2NMe_2$ | $CF_3$ | H | H | H | H | 183-185 |
| 12-120 | H | 4-t-BuBnS | $CF_3$ | H | H | H | H | 132-138 |
| 12-121 | H | n-PrC≡C | $CF_3$ | H | H | H | H | 181-184 |
| 12-122 | H | c-PrC≡C | $CF_3$ | H | H | H | H | 209-211 |
| 12-123 | H | t-BuC≡C | $CF_3$ | H | H | H | H | 224-226 |
| 12-124 | H | n-Pen | $CF_3$ | H | H | H | H | 144-147 |
| 12-125 | H | c-PrCH$_2$CH$_2$ | $CF_3$ | H | H | H | H | 223-226 |
| 12-126 | H | t-BuCH$_2$CH$_2$ | $CF_3$ | H | H | H | H | 150-151 |
| 12-127 | H | MeOCH$_2$C≡C | $CF_3$ | H | H | H | H | 150-153 |

TABLE 32

| Intermediate No. | $X^1$ | $X^2$ | $X^3$ | $Y^1$ | $Y^2$ | $Y^3$ | $Y^4$ | Physical property |
|---|---|---|---|---|---|---|---|---|
| 12-128 | H | MeOC(Me)$_2$C≡C | $CF_3$ | H | H | H | H | 210-212 |
| 12-129 | H | CH=CHCO$_2$(t-Bu) (E) | $CO_2$(t-Bu) | H | H | H | H | 141-142 |
| 12-130 | H | COCH$_2$(t-Bu) | CH$_2$(t-Bu) | H | H | H | H | NMR |
| 12-131 | H | t-BuCO$_2$CH$_2$C≡C | $CF_3$ | H | H | H | H | 172-175 |
| 12-132 | H | t-BuC≡C | $CO_2$(t-Bu) | H | H | H | H | 204-208 |
| 12-133 | H | t-BuCO$_2$CH$_2$CH$_2$CH$_2$ | $CF_3$ | H | H | H | H | 108-111 |
| 12-134 | H | CH$_2$CH$_2$CO$_2$(t-Bu) | $CO_2$(t-Bu) | H | H | H | H | |
| 12-135 | H | Br | OCF$_2$CONMe$_2$ | H | H | H | H | 140-142 |
| 12-136 | H | t-BuCH$_2$CH$_2$ | $CO_2$(t-Bu) | H | H | H | H | 98-100 |
| 12-137 | H | CF$_3$CH$_2$OCH$_2$C≡C | $CF_3$ | H | H | H | H | |
| 12-138 | H | $CO_2$(t-Bu) | $OCHF_2$ | H | H | H | H | 169-171 |
| 12-139 | H | —COC(Me)$_2$CH$_2$CH$_2$— | | H | H | H | H | 228-230 |
| 12-140 | H | SCH$_2$CF$_2$CF$_3$ | H | H | H | H | H | 201-203 |
| 12-141 | H | COi-Bu | i-Bu | H | H | H | H | NMR |
| 12-142 | H | $CO_2Et$ | CH=CHCO$_2$Et (E) | H | H | H | H | NMR |
| 12-143 | H | $CO_2$(t-Bu) | CH=CHCO$_2$(t-Bu) (E) | H | H | H | H | NMR |
| 12-144 | H | $CO_2$(t-Bu) | t-BuC≡C | H | H | H | H | NMR |
| 12-145 | H | I | Me | H | H | H | H | |
| 12-146 | H | t-BuC≡C | Me | H | H | H | H | |
| 12-147 | H | $CO_2Et$ | CH$_2$CH$_2$CO$_2$Et | H | H | H | H | NMR |
| 12-148 | H | COEt | Et | H | H | H | H | NMR |
| 12-149 | H | $SCF_3$ | H | H | H | H | H | |
| 12-150 | H | t-BuCH$_2$OCH$_2$C≡C | $CF_3$ | H | H | H | H | |
| 12-151 | H | t-BuCH$_2$CH$_2$OCH$_2$C≡C | $CF_3$ | H | H | H | H | |
| 12-152 | H | t-BuC≡C | CF$_3$CF$_2$CH$_2$O | H | H | H | H | |

TABLE 33

| Intermediate No. | $X^1$ | $X^2$ | $X^3$ | $Y^1$ | $Y^2$ | $Y^3$ | $Y^4$ | Physical property |
|---|---|---|---|---|---|---|---|---|
| 12-153 | H | MeOC(Me)$_2$C≡C | CF$_3$CF$_2$CH$_2$O | H | H | H | H | |
| 12-154 | H | CH=CHCO$_2$(t-Bu) (E) | $OCHF_2$ | H | H | H | H | |
| 12-155 | H | CH$_2$CH$_2$CO$_2$(t-Bu) | $OCHF_2$ | H | H | H | H | |
| 12-156 | H | t-BuC≡C | $OCHF_2$ | H | H | H | H | |
| 12-157 | H | t-BuCH$_2$CH$_2$ | $OCHF_2$ | H | H | H | H | |
| 12-158 | H | MeOC(Me)$_2$C≡C | $CO_2$(t-Bu) | H | H | H | H | |

TABLE 33-continued

| Intermediate No. | $X^1$ | $X^2$ | $X^3$ | $Y^1$ | $Y^2$ | $Y^3$ | $Y^4$ | Physical property |
|---|---|---|---|---|---|---|---|---|
| 12-159 | H | MeOC(Me)$_2$CH$_2$CH$_2$ | CO$_2$(t-Bu) | H | H | H | H | |
| 12-160 | H | —COC(Et)$_2$CH$_2$CH$_2$— | | H | H | H | H | |
| 12-161 | H | t-BuCH$_2$CH$_2$ | Me | H | H | H | H | |
| 12-162 | H | PhOCH$_2$C≡C | Me | H | H | H | H | NMR |
| 12-163 | H | PhOCH$_2$CH$_2$CH$_2$ | Me | H | H | H | H | |
| 12-164 | H | MeOC(Me)$_2$C≡C | Me | H | H | H | H | |
| 12-165 | H | MeOC(Me)$_2$CH$_2$CH$_2$ | Me | H | H | H | H | |
| 12-166 | H | CO$_2$(t-Bu) | CH$_2$CH$_2$CO$_2$(t-Bu) | H | H | H | H | NMR |
| 12-167 | H | CO$_2$(t-Bu) | MeOCH$_2$C≡C | H | H | H | H | NMR |
| 12-168 | H | CO$_2$(t-Bu) | MeOC(Me)$_2$C≡C | H | H | H | H | |
| 12-169 | H | CO$_2$(t-Bu) | CF$_3$CH$_2$OCH$_2$C≡C | H | H | H | H | |
| 12-170 | H | CO$_2$(t-Bu) | CF$_3$CH$_2$OC(Me)$_2$C≡C | H | H | H | H | |
| 12-171 | H | C(=NOMe)i-Bu | i-Bu | H | H | H | H | |

[Formula 18]

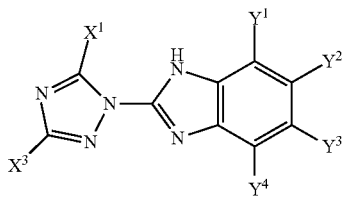

(11-C)

TABLE 34

| Intermediate No. | $X^1$ | $X^3$ | $Y^1$ | $Y^2$ | $Y^3$ | $Y^4$ | Physical property |
|---|---|---|---|---|---|---|---|
| 13-1 | H | CF$_3$ | H | H | H | H | 195-197 |
| 13-2 | H | C$_2$F$_5$ | H | H | H | H | 166-168 |
| 13-3 | H | PhCH$_2$CH$_2$ | H | H | H | H | NMR |
| 13-4 | H | SMe | H | H | H | H | 44-45 |
| 13-5 | H | CO$_2$(t-Bu) | H | H | H | H | |
| 13-6 | H | CO$_2$(t-Amyl) | H | H | H | H | |
| 13-7 | H | CO$_2$(CMe$_2$C≡CH) | H | H | H | H | |
| 13-8 | H | CO$_2$(CMe$_2$Ph) | H | H | H | H | |
| 13-9 | H | CO$_2$(2,6-Me$_2$Ph) | H | H | H | H | |

[Formula 19]

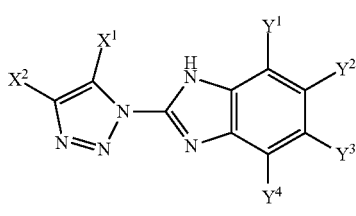

(11-D)

TABLE 35

| Intermediate No. | $X^1$ | $X^2$ | $Y^1$ | $Y^2$ | $Y^3$ | $Y^4$ | Physical property |
|---|---|---|---|---|---|---|---|
| 14-1 | H | CO$_2$(t-Bu) | H | H | H | H | |
| 14-2 | H | CO$_2$(t-Amyl) | H | H | H | H | |
| 14-3 | H | CO$_2$(CMe$_2$C≡CH) | H | H | H | H | |
| 14-4 | H | CO$_2$(CMe$_2$Ph) | H | H | H | H | |
| 14-5 | H | CO$_2$(2,6-Me$_2$Ph) | H | H | H | H | |

[Formula 20]

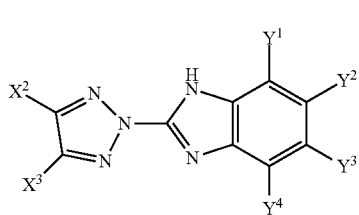

(11-E)

TABLE 36

| Intermediate No. | $X^2$ | $X^3$ | $Y^1$ | $Y^2$ | $Y^3$ | $Y^4$ | Physical property |
|---|---|---|---|---|---|---|---|
| 15-1 | H | CO$_2$(t-Bu) | H | H | H | H | |
| 15-2 | Me | CO$_2$(t-Bu) | H | H | H | H | |
| 15-3 | Me | CO$_2$(t-Amyl) | H | H | H | H | |
| 15-4 | Me | CO$_2$(CMe$_2$C≡CH) | H | H | H | H | |
| 15-5 | Me | CO$_2$(CMe$_2$Ph) | H | H | H | H | |
| 15-6 | Me | CO$_2$(2,6-Me$_2$Ph) | H | H | H | H | |
| 15-7 | CO$_2$(t-Bu) | CO$_2$(t-Bu) | H | H | H | H | |

[Formula 21]

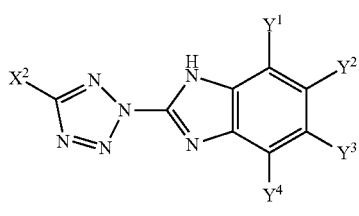

(11-F)

TABLE 37

| Intermediate No. | $X^2$ | $Y^1$ | $Y^2$ | $Y^3$ | $Y^4$ | Physical property |
|---|---|---|---|---|---|---|
| 16-1 | CO$_2$(t-Bu) | H | H | H | H | |
| 16-2 | CO$_2$(t-Amyl) | H | H | H | H | |
| 16-3 | CO$_2$(CMe$_2$C≡CH) | H | H | H | H | |
| 16-4 | CO$_2$(CMe$_2$Ph) | H | H | H | H | |
| 16-5 | CO$_2$(2,6-Me$_2$Ph) | H | H | H | H | |

[Formula 22]

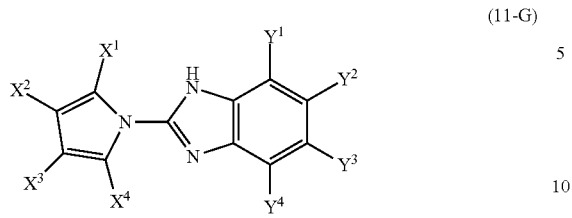

(11-G)

TABLE 38

| Intermediate No. | X¹ | X² | X³ | X⁴ | Y¹ | Y² | Y³ | Y⁴ | Physical property |
|---|---|---|---|---|---|---|---|---|---|
| 17-1 | H | $CO_2$(t-Bu) | H | H | H | H | H | H | 101-102 |
| 17-2 | H | $CO_2$(t-Amyl) | H | H | H | H | H | H | |
| 17-3 | H | $CO_2$($CMe_2$C≡CH) | H | H | H | H | H | H | |
| 17-4 | H | $CO_2$($CMe_2$Ph) | H | H | H | H | H | H | |
| 17-5 | H | $CO_2$(2,6-$Me_2$Ph) | H | H | H | H | H | H | |
| 17-6 | H | $CO_2$Me | $CO_2$Me | H | H | H | H | H | NMR |
| 17-7 | H | $CO_2$Et | $CO_2$Et | H | H | H | H | H | NMR |

TABLE 39

| Intermediate No. | ¹H-NMR data ($CDCl_3$) |
|---|---|
| 11-2 | 8.45(s, 1H), 8.00-7.85(m, 2H), 7.36-7.32(m, 2H), 7.20(s, 1H), 2.70-2.48(m, 8H), 1.40(t, 3H) |
| 11-4 | 8.39(s, 1H), 8.20(s, 1H), 7.80-7.74(m, 1H), 7.53-7.47(m, 1H), 7.40-7.34(m, 1H), 7.18-7.13(m, 1H), 1.36(t, 9H) |
| 11-7 | 8.00(s, 1H), 7.97(dd, 1H), 7.79-7.73(m, 1H), 7.50-7.44(m, 2H), 7.35-7.30(m, 5H), 7.10(s. 1H), 4.03 (s, 2H) |
| 11-8 | 8.00-7.96(m, 2H), 7.80-7.74(m, 1H), 7.50-7.44(m, 2H), 7.31-7.15(m, 5H), 7.13(s, 1H), 3.09-2.94(m, 4H) |
| 11-11 | 11.32(bs, 1H), 8.23(bs, 1H), 7.68(bs, 1H), 7.41(br, 1H), 7.36(d, 1H), 7.32-7.24(m, 2H), 7.24-7.08(m, 3H), 7.02(d, 1H), 2.98-2.88(m, 4H) |
| 11-12 | 11.60(bs, 1H), 7.78-7.34(m, 3H), 7.34-7.24(m, 3H), 7.14-6.97(m, 3H), 3.11-2.99(m, 2H), 2.97-2.86(m, 2H) |
| 11-13 | 10.18(bs, 1H), 7.78(bs, 1H), 7.73-7.66(m, 2H), 7.38-7.32(m, 2H), 7.32-7.18(m, 3H), 7.12-7.02(m, 2H), 1.94-1.84(m, 2H), 1.78-1.68(m, 2H) |
| 11-14 | 8.25(s, 1H), 7.67-7.56(m, 2H), 7.49-7.13(m, 9H), 4.51(s, 2H) |
| 11-15 | 11.56(bs, 1H), 8.34(bs, 1H), 7.82-7.60(m, 2H), 7.54-7.36(m, 3H), 7.34-7.25(m, 2H), 6.94(d, 2H), 5.09(s, 2H) |
| 11-16 | 11.70(bs, 1H), 8.35(bs, 1H), 7.90-7.34(m, 3H), 7.32-7.23(m, 2H), 7.07(d, 2H), 5.04(s, 2H) |
| 11-19 | 8.55(s, 1H), 7.73(s, 1H), 7.31-7.29(m, 4H) |
| 11-22 | 8.77(s, 1H), 8.52(s, 2H), 8.08(s, 1H) |

TABLE 40

| Intermediate No. | ¹H-NMR data ($CDCl_3$) |
|---|---|
| 11-23 | 8.41(s, 1H), 8.03(s, 1H), 8.01-7.97(m, 1H), 7.57-7.53(m, 1H), 7.42-7.38 (m, 2H) |
| 11-24 | 8.36(s, 1H), 8.05(s, 1H), 7.88-7.82(m, 1H), 7.58-7.50(m, 1H), 7.39-7.34 (m, 2H) |
| 11-32 | 14.59(bs, 1H), 9.04(d, 1H), 8.90(d, 1H), 7.76-7.70(m, 1H), 7.69-7.63(m, 1H), 7.47-7.41(m, 2H), 7.35-7.28(m, 5H), 1.90(s, 6H) |
| 11-35 | 8.59(d, 1H), 8.48(d, 1H), 7.66-7.60(m, 2H), 7.38-7.32(m, 2H), 6.02-5.96(m, 1H) |
| 12-5 | 9.83(bs, 1H), 8.27(s, 1H), 7.72-7.70(m, 1H), 7.47-7.44(m, 1H), 7.32-7.30(m, 2H), 7.15-7.13(m, 2H), 7.01-6.96(m, 2H), 2.93(s, 4H) |
| 12-6 | 9.43(bs, 1H), 8.27(s, 1H), 7.72-7.70(m, 1H), 7.46-7.44(m, 1H), 7.32-7.29(m, 2H), 7.12(d, 2H), 6.85(d, 2H), 3.79(s, 3H), 2.91(s, 4H) |
| 12-9 | 9.94(bs, 1H), 8.67(s, 1H), 7.75-7.73(m, 1H), 7.54-7.47(m, 3H), 7.35-7.32(m, 2H), 7.09-7.05(m, 2H) |
| 12-18 | 9.93(bs, 1H), 8.36(s, 1H), 7.76-7.68(m, 1H), 7.50-7.42(m, 1H), 7.35-7.29(m, 2H), 2.67(q, 2H), 1.30(t, 3H) |
| 12-20 | 9.90(bs, 1H), 8.66(s, 1H), 7.74-7.72(m, 1H), 7.48-7.46(m, 1H), 7.34-7.31(m, 2H), 6.68-6.61(m, 1H), 5.72(d, 1H), 5.40(d, 1H) |

TABLE 40-continued

| Intermediate No. | $^1$H-NMR data (CDCl$_3$) |
|---|---|
| 12-29 | 10.4(bs, 1H), 7.48-7.42(m, 2H), 7.35-7.30(m, 3H), 3.60(s, 3H), 2.79(s, 3H) |
| 12-30 | 10.04(bs, 1H), 9.04(s, 1H), 7.79-7.72(m, 1H), 7.55-7.47(m, 1H), 7.38-7.33 (m, 2H), 2.05(s, 9H) |
| 12-40 | 9.50(bs, 1H), 8.85(s, 1H), 7.73-7.68(m, 1H), 7.50-7.42(m, 1H), 7.34-7.28 (m, 2H), 4.85(t, 2H), 4.18-4.01(m, 2H), 1.35(t, 3H) |

TABLE 41

| Intermediate No. | $^1$H-NMR data (CDCl$_3$) |
|---|---|
| 12-42 | 10.62(bs, 1H), 8.52(d, 1H), 7.75-7.68(m, 1H), 7.43-7.36(m, 1H), 7.33-7.25(m, 2H), 6.95(d, 1H), 1.59(s, 9H) |
| 12-43 | 10.30(bs, 1H), 8.52(s, 1H), 7.75-7.69(m, 1H), 7.48-7.41(m, 1H), 7.35-7.28(m, 2H), 1.65(s, 9H) |
| 12-46 | 9.79(bs, 1H), 8.87(s, 1H), 7.75-7.69(m, 1H), 7.49-7.43(m, 1H), 7.36-7.28(m, 2H), 1.56(s, 9H) |
| 12-47 | 9.96(br, 1H), 8.85(s, 1H), 7.76-7.68(m, 1H), 7.50-7.44(m, 1H), 7.37-7.28(m, 2H), 1.60(s, 9H) |
| 12-48 | 10.00(bs, 1H), 8.82(s, 1H), 7.74-7.67(m, 1H), 7.48-7.41(m, 1H), 7.33-7.25(m, 2H), 2.98(q, 2H), 1.57(s, 9H), 1.33(t, 3H) |
| 12-49 | 9.62(bs, 1H), 8.77(s, 1H), 7.72-7.67(m, 1H), 7.47-7.41(m, 1H), 7.33-7.22(m, 2H), 2.70-2.62(m, 1H), 1.58(s, 9H), 1.08-1.03(m, 4H) |
| 12-51 | 8.88(s, 1H), 7.79-7.71(m, 1H), 7.62-7.40(m, 1H), 7.39-7.27(m, 2H), 4.82 (t, 2H) |
| 12-52 | 10.2(bs, 1H), 9.06(s, 1H), 7.79-7.23(m, 1H), 7.54-7.47(m, 1H), 7.39-7.32 (m, 2H), 5.25(sep, 1H), 1.37(d, 6H) |
| 12-54 | 9.85(bs, 1H), 8.95(s, 1H), 7.78-7.73(m, 1H), 7.53-7.47(m, 1H), 7.37-7.34(m, 2H), 3.09-3.00(m, 1H), 1.40(d, 3H),1.27(d, 3H) |
| 12-55 | 9.98(bs, 1H), 9.04(s, 1H), 7.78-7.75(m, 1H), 7.53-7.50(m, 1H), 7.39-7.36(m, 2H), 3.43-3.35(m, 1H), 1.42(d, 6H) |

TABLE 42

| Intermediate No. | $^1$H-NMR data (CDCl$_3$) |
|---|---|
| 12-75 | 8.75(s, 1H), 7.58-7.56(m, 2H), 7.30-7.27(m, 2H), 4.69-4.67(m, 2H), 2.44-2.40(m, 1H), 1.55(s, 9H) |
| 12-76 | 8.35(s, 1H), 7.92-7.88(m, 1H), 7.45-7.41(m, 1H), 7.23-7.12(m, 2H), 6.32-6.03(tt, 1H), 4.57-4.41(q, 2H), 1.58(s, 9H) |
| 12-77 | 9.53(bs, 1H), 8.75(s, 1H), 7.73-7.67(m, 1H), 7.49-7.44(m, 1H), 7.33-7.28(m, 2H), 6.32-6.00(m, 1H), 4.75(t, 2H) |
| 12-78 | 9.81(bs, 1H), 8.96(s, 1H), 7.71-7.68(dd, 1H), 7.49-7.46(dd, 1H), 7.32-7.28(m, 2H), 3.85(s, 3H), 1.50(s, 9H) |
| 12-80 | 9.79(bs, 1H), 8.87(s, 1H), 7.74-7.73(m, 1H), 7.52-7.51(m, 1H), 7.35-7.31(m, 2H), 4.39-4.35(q, 2H), 1.41-1.39(t, 3H) |
| 12-81 | 11.2(bs, 1H), 8.81(s, 1H), 7.71-7.64(m, 1H), 7.52-7.45(m, 1H), 7.35-7.29(m, 2H), 1.59(s, 9H) |
| 12-82 | 9.76(bs, 1H), 7.98(s, 1H), 7.80-7.71(m, 1H), 7.70-7.64(d, 1H), 7.48-7.39(m, 1H), 7.30-7.28(m, 2H), 7.85-7.68(dd, 1H), 1.80-1.72(m, 1H), 1.55(s, 9H), 0.99-0.89(m, 2H), 0.77-0.68(m, 2H) |
| 12-83 | 9.82(bs, 1H), 7.99(s, 1H), 7.75-7.72(dd, 1H), 7.45-7.43(dd, 1H), 7.30-7.27(m, 2H), 3.85-3.81(t, 2H), 1.69-1.68(dt, 2H), 1.64(s, 9H), 1.48-1.40(m, 1H), 0.41-0.39(m, 2H), 0.16-0.14(m, 2H) |
| 12-85 | 9.68(bs, 1H), 8.84(s, 1H), 7.72-7.68(m, 1H), 7.48-7.44(m, 1H), 7.32-7.26(m, 2H), 6.76(s, 1H), 2.19(s, 3H), 2.03(s, 3H), 1.57(s, 9H) |
| 12-86 | 9.88(bs, 1H), 8.83(s, 1H), 7.72-7.70(dd, 1H), 7.43-7.41(dd, 1H), 7.30-7.27(m, 2H), 2.84-2.82(d, 2H), 2.16-2.04(m, 1H), 1.56(s, 9H), 0.99-0.97(d, 6H) |
| 12-88 | 9.71(bs, 1H), 8.82(s, 1H), 7.71-7.68(m, 1H), 7.47-7.44(m, 1H), 7.30-7.26(m, 7H), 3.32-3.26(m, 1H), 3.15-3.11(m, 1H), 1.57(s, 9H) |
| 12-91 | 9.68(bs, 1H), 8.72(s, 1H), 7.72-7.67(m, 1H), 7.49-7.43(m, 1H), 7.33-7.28(m, 2H), 5.02(d, 2H), 2.54(t, 1H) |

TABLE 43

| Intermediate No. | ¹H-NMR data (CDCl₃) |
|---|---|
| 12-93 | 10.2(bs, 1H), 8.66(s, 1H), 7.70-7.69(m, 1H), 7.57-7.56(m, 1H), 7.36-7.35(m, 1H), 6.05(br s, 1H), 4.13-4.10(d, 2H), 1.49(s, 9H) |
| 12-94 | 10.6(bs, 1H), 8.82(s, 1H), 7.88(br s, 1H), 7.82-7.79(m, 1H), 7.55-7.51(m, 1H), 7.42-7.32(m, 2H), 7.34(m, 1H), 4.37-4.30(m, 2H), 2.42-2.38(m, 2H) |
| 12-95 | 9.69(bs, 1H), 8.53(s, 1H), 7.69-7.66(dd, 1H), 7.48-7.45(dd, 1H), 7.30-7.27(m, 1H), 5.93(br s, 1H), 2.83-2.80(m, 1H), 1.58(s, 9H), 0.88-0.86(m, 2H), 0.59-0.57(m, 2H) |
| 12-96 | 8.91(bs, 1H), 8.49(s, 1H), 7.57-7.52(m, 1H), 7.35-7.30(m, 1H), 7.35-7.32(m, 2H), 5.73(bs, 1H), 1.51(s, 9H), 1.45(s, 9H) |
| 12-97 | 10.5(bs, 1H), 8.69(s, 1H), 7.99-7.92(d, 1H), 7.83-7.77(d, 1H), 7.51-7.42(m, 2H), 3.1-2.98(m, 6H), 2.23-2.18(br, 18H) |
| 12-98 | 9.85(bs, 1H), 8.81(s, 1H), 7.75-7.69(m, 1H), 7.52-7.46(m, 1H), 7.33-7.26(m, 2H), 1.50(s, 9H) |
| 12-102 | 9.77(bs, 1H), 8.25(d, 1H), 7.68-7.63(m, 1H), 7.44-7.38(m, 1H), 7.29-7.19(m, 2H), 5.97(d, 1H), 4.30(t, 2H), 2.44(t, 2H), 2.16-2.07(m, 2H), 1.47(s, 9H) |
| 12-112 | 10.26(bs, 1H), 8.83(s, 1H), 7.74-7.72(m, 1H), 7.63(d, 1H), 7.49-7.47(m, 1H), 7.35-7.31(m, 1H), 6.41(d, 1H), 3.92(s, 2H), 0.99(s, 9H) |
| 12-113 | 9.95(bs, 1H), 8.78(s, 1H), 7.74-7.72(m, 1H), 7.66(d, 1H), 7.49-7.47(m, 1H), 7.43-7.30(m, 6H), 6.42(d, 1H), 5.24(s, 2H), 1.33(s, 9H) |
| 12-118 | 10.31(bs, 1H), 8.85(s, 1H), 7.57-7.55(m, 1H), 7.43-7.41(m, 1H), 7.33-7.29(m, 2H), 5.50(s, 3H), 2.59(s, 3H) |
| 12-130 | 9.82(bs, 1H), 8.87(s, 1H), 7.72-7.68(dd, 1H), 7.50-7.45(dd, 1H), 7.32-7.28(m, 2H), 3.03(s, 2H), 2.68(s, 2H), 1.07(s, 9H), 1.00(s, 9H) |
| 12-141 | 9.83(bs, 1H), 8.89(s, 1H), 7.73-7.71(dd, 1H), 7.48-7.46(dd, 1H), 7.34-7.28(m, 2H), 2.88-2.87(d, 2H), 2.68-2.66(d, 2H), 2.30-2.24(m, 1H), 2.14-2.07(m, 1H), 0.10-0.97(d, 12H) |
| 12-142 | 10.5(bs, 1H), 8.99(s, 1H), 8.14-8.10(d, 1H), 7.72-7.68(m, 1H), 7.49-7.44(m, 1H), 7.33-7.29(m, 2H), 6.96-6.92(d, 1H), 4.38-4.36(q, 2H), 4.30-4.27(q, 2H), 1.41-1.35(t, 6H) |
| 12-143 | 10.49(bs, 1H), 8.90(s, 1H), 8.04-8.00(d, 1H), 7.73-7.72(m, 1H), 7.49-7.48(m, 1H), 7.32-7.27(m, 2H), 6.82-6.78(d, 1H), 1.59(s, 9H), 1.53(s, 9H) |

TABLE 44

| Intermediate No. | ¹H-NMR data(CDCl₃) |
|---|---|
| 12-144 | 10.38(bs, 1H), 8.87(s, 1H), 7.72-7.69(m, 1H), 7.44-7.41(m, 1H), 7.31-7.27(m, 2H), 2.05(s, 9H), 1.59(s, 9H) |
| 12-147 | 9.99(bs, 1H), 8.90(s, 1H), 7.72-7.70(m, 1H), 7.44-7.42(m, 1H), 7.32-7.23(m, 2H), 4.37-4.30(q, 2H), 4.20-4.13(q, 2H), 3.34-3.29(t, 2H), 2.89-2.84(t, 2H), 1.38-1.32(t, 3H), 1.26-1.22(t, 3H) |
| 12-148 | 10.12(bs, 1H), 8.90(s, 1H), 7.72-7.70(m, 1H), 7.46-7.44(m, 1H), 7.33-7.22(m, 2H), 3.04-2.98(q, 2H), 2.88-2.81(q, 2H), 1.44-1.35(t, 3H), 1.29-1.21(t, 3H) |
| 12-162 | 9.64(bs, 1H), 8.45(s, 1H), 7.93-7.90(m, 1H), 7.43-7.01(m, 7H), 4.93(s, 2H), 2.34(s, 3H) |
| 12-166 | 9.81(bs, 1H), 8.81(s, 1H), 7.70-7.64(m, 1H), 7.43-7.37(m, 1H), 7.32-7.27(m, 2H), 3.28-3.22(t, 2H), 2.78-2.72(t, 2H), 1.55(s, 9H), 1.42(s, 9H) |
| 12-167 | 10.21(bs, 1H), 8.88(s, 1H), 7.73-7.71(m, 1H), 7.46-7.45(m, 1H), 7.32-7.30(m, 2H), 4.38(s, 2H), 3.49(s, 3H), 1.58(s, 9H) |
| 13-3 | 9.05(s, 1H), 8.00(s, 1H), 7.75-7.45(m, 2H), 7.34-7.14(m, 2H), 7.09-7.02(m, 1H), 3.18-3.06(m, 4H) |
| 17-6 | 11.33(br s, 1H), 8.10(s, 2H), 7.72(s, 1H), 7.41(s, 1H), 7.29-7.20(s, 2H), 3.42(s, 6H) |
| 17-7 | 11.41(br s, 1H), 8.11(s, 2H), 7.71(m, 1H), 7.48(s, 1H), 7.35-7.29(m, 2H), 4.25-4.21(m, 4H), 1.31-1.25(s, 6H) |

The agricultural and horticultural insecticidal and acaricidal agent comprising the benzimidazole compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, other pests such as nematodes, or mites, etc.

Examples of the above pests or nematodes include the following.

Examples of the species of the order Lepidoptera include *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina sp., Carposina niponensis, Conogethes punctiferalis, Synanthedon sp., Lyonetia clerkella, Papilio helenus, Colias erate poliographus, Phalera flavescens,* the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis.*

Examples of the species of the order Hemiptera include *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus spp., Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorios, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigones, Clovia punctata, Empoasca sp., Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa aceta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni,*

*Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii.*

Examples of the species of the order Coleoptera include *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis.*

Examples of the species of the order Diptera include *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella.*

Examples of the species of the order Hymenoptera include *Pristomyrmex pungens,* the species of the family Bethylidae, *Monomorium pharaonis, Pheidole noda, Athalia rosae, Dryocosmus kuriphilus, Formica fusca japonica,* the species of the subfamily Vespinae, *Athalia infumata infumata, Arge pagana, Athalia japonica, Acromyrmex* spp., *Solenopsis* spp., *Arge mali* and *Ochetellus glaber.*

Examples of the species of the order Orthoptera include *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma.*

Examples of the species of the order Thysanoptera include *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei.*

Examples of the species of the order Acari include *Leptotrombidium akamushi, Tetranychus ludeni, Dermacentor variabilis, Tetranychus truncatus, Ornithonyssus bacoti, Demodex canis, Tetranychus viennensis, Tetranychus kanzawai,* the species of the family Ixodidae such as *Rhipicephalus sanguineus, Cheyletus malaccensis, Tyrophagus putrescentiae, Dermatophagoides farinae, Latrodectus hasseltii, Dermacentor taiwanensis, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.

Examples of the species of the order Isoptera include *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus.*

Examples of the species of the order Blattodea include *Periplaneta fuliginosa, Blattella germanica, Blatta orientalis, Periplaneta brunnea, Blattella lituricollis, Periplaneta japonica* and *Periplaneta americana.*

Examples of the species of the order Siphonaptera include *Pulex irritans, Ctenocephalides felis* and *Ceratophyllus gallinae.*

Examples of the species of the phylum Nematoda include *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans.*

Examples of the species of the phylum Mollusca include such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanensis; Dermanyssus gallinae;* the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, Plasmodium, intestinal Sarcocystis, Toxoplasma and Cryptosporidium.

More detailed examples of endoparasites include: the species of the order Enoplida such as *Trichuris* subgenus (whipworms) (*Trichuris* spp.), *Capillaria* subgenus (thread worms) (*Capillaria* spp.), *Torikomosoidesu* subgenus (*Trichomosoides* spp.), and *Trichinella* subgenus (*Trichinella* genus) (*Trichinella* spp.); the species of the order Rhabditia such as *Micronema* subgenus (*Micronema* spp.) and *Strongyloides* subgenus (*Strongyloides* spp.); the species of the order Strongylida, for example, *Stronylus* subgenus (strongyles) (*Stronylus* spp.), *Triodontophorus* subgenus (*Triodontophorus* spp.), *Oesophagodontus* subgenus (*Oesophagodontus* spp.), *Trichonema* subgenus (*Trichonema* spp.), *Gyalocephalus* subgenus (*Gyalocephalus* spp.) *Cylindropharynx* subgenus (*Cylindropharynx* spp.) *Poteriostomum* subgenus (*Poteriostomum* spp.), *Cyclococercus* subgenus (*Cyclococercus* spp.), *Cylicostephanus* subgenus (*Cylicostephanus* spp.), *Oesophagostomum* subgenus (*Oesophagostomum* genus) (*Oesophagostomum* spp.), *Chabertia* subgenus (*Chabertia* spp.), *Stephanurus* subgenus (*Stephanurus* dentatus) (*Stephanurus* spp.), *Ancylostoma* subgenus (old world hookworms) (*Ancylostoma* spp.) *Uncinaria* subgenus (*Uncinaria* spp.), and *Bunostomum* subgenus (*Bunostomum* spp.); *Globocephalus* subgenus (*Globocephalus* spp.), *Syngamus* subgenus (syngamus worms) (*Syngamus* spp.), *Cyathostoma* subgenus (*Cyathostoma* spp.), *Metastrongylus* subgenus (lungworms) (*Metastrongylus* spp.), *Dictyocaulus* subgenus (*Dictyocaulus* spp.), *Muellerius* subgenus (*Muellerius* spp.), *Protostrongylus* subgenus (*Protostrongylus* spp.) *Neostrongylus* subgenus (*Neostrongylus* spp.), *Cystocaulus* subgenus (*Cystocaulus* spp.), *Pneumostrongylus* subgenus (*Pneumostrongylus* spp.), *Spicocaulus* subgenus (*Spicocaulus* spp.), *Elaphostrongylus* subgenus (*Elaphostrongylus* spp.), *Parelaphostrongylus* subgenus (*Parelaphostrongylus* spp.) *Crenosoma* subgenus (*Crenosoma* spp.), *Paracrenosoma* subgenus (*Parelaphostrongylus* spp.), *Angiostrongylus* subgenus (*angiostrongylus* worms) (*Angiostrongylus* spp.), *Aelurosutrongylus* subgenus (*Aelurosutrongylus* spp.), *Filaroides* subgenus (*Filaroides* spp.), *Parafilaroides* subgenus (*Parafilaroides* spp.), *Trichostrongylus* subgenus (hairworms) (*Trichostrongylus* spp.), *Haemonchus* subgenus (haemonchus worm) (*Haemonchus* spp.), *Ostertagia* subgenus (*Ostertagia* spp.), *Marshallagia* subgenus (*Marshallagia* spp.), *Cooperia* subgenus (*Cooperia* spp.), *Nematodirus* subgenus (nematode) (*Nematodirus* spp.), *Hyostrongylus* subgenus (*Hyostrongylus* spp.), *Obeliscoides* subgenus (*Obeliscoides* spp.), *Amidostomum* subgenus (*Amidostomum* spp.), and *Ollulanus* subgenus (*Ollulanus* spp.); the species of the order Oxyurida such as *Oxyuris* subgenus (horse pinworms) (*Oxyuris* spp.), *Enterobius* subgenus (pinworms) (*Enterobius* spp.), *Passalurus* subgenus (*Passalurus* spp.), *Syphacia* subgenus (*Syphacia* spp.), *Aspiculuris* subgenus (*Aspiculuris* spp.), and *Heterakis* subgenus (*Heterakis* spp.); the species of the order Ascaridia such as *Ascaris* subgenus (roundworms) (*Ascaris* spp.), *Toxascaris* subgenus (*Toxascaris* spp.), *Toxocara* subgenus (dog ascariasis) (*Toxocara* spp.), *Parascaris* subgenus (parascaris equorum) (*Parascaris* spp.), *Anisakis* subgenus (*Anisakis* spp.), and *Ascaridia* subgenus (roundworms) (*Ascaridia* spp.); the species of the order Spirurida (spiruroids) such as *Gnathostoma* subgenus (gnathostoma spinigerm) (*Gnathostoma* spp.), *Physaloptera* subgenus (*Physaloptera* spp.), *Thelazia* subgenus (*Thelazia* spp.), *Gongylonema* subgenus (*Gongylonema* spp.), *Habronema* subgenus (*Habronema* spp.), *Parabronema* subgenus (*Parabronema* spp.), *Draschia* subgenus (*Draschia* spp.), and *Dracunculus* subgenus (Guinea worms) (*Dracunculus* spp.); the species of the order Filariida such as *Stephanofilaria* subgenus (*Stephanofilaria* spp.), *Parafilaria* subgenus (*Parafilaria* spp.), *Setaria* Subgenus (*Setaria* spp.), *Loa* subgenus (*Loa* spp.), *Dirofilaria* subgenus (dog heartworms) (*Dirofilaria* spp.), *Litomosoides* subgenus (*Litomosoides* spp.), *Brugia* subgenus (*Brugia* spp.), *Wuchereria* subgenus (heartworms) (*Wuchereria* spp.), and *Onchocerca* subgenus (*Onchocerca* spp.); and the species of the order Gigentorhynchida such as *Filicollis* subgenus (*Filicollis* spp.), *Moniliforumis* subgenus (*Moniliforumis* spp.), *Macracanthorhynchus* subgenus (*Macracanthorhynchus* spp.), and *Prosthenorchis* subgenus (*Prosthenorchis* spp.).

The endoparasite control agent comprising the benzimidazole compound represented by the general formula (1) of the present invention or a salt thereof as an active ingredient is effective for not only parasites that live in the body of an intermediate or final host, but also parasites that, live in the body of a reservoir host. The benzimidazole compound represented by the general formula (1) of the present invention or a salt thereof is effective for parasites at their every developmental stage. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound, is effective against their eggs, larvae and adults. The compound of the present invention is capable of not only combating parasites in the living body, but also even preventing parasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection, from saltwater fish, freshwater fish, crustaceans, shellfish, raw meat of domestic animals, etc.; infection from mosquitoes, gadflies, flies, cockroaches, mites and ticks, fleas, lice, assassin bugs, trombiculid mites, etc.; and the like can be prevented from occurring.

When the compounds of the present invention are used to control endoparasites in pet mammals and birds, the compounds of the present invention may be administered in an effective amount together with pharmaceutically acceptable additives orally, parenterally by injection (intramuscular, subcutaneously, intravenously or intraperitoneally); percutaneously by dipping, spraying, bathing, washing, pouring-on and spotting-on and dusting, or intranasally. The compounds of the present invention may be administered through molded articles such as chips, plates, bands, collars, ear marks, limb bands and ID tags. The compounds of the present invention are administered in an arbitrary dosage form suitable for the administration route.

The dosage form may be a solid preparation such as a dust, a granule, a wettable powder, a pellet, a tablet, a ball, a capsule and an molded article containing an active ingredient, a liquid preparation such as an injection fluid, an oral liquid, a liquid preparation applied to the skin or coelom, a pour-on preparation, a spot-on preparation, a flowable, an emulsion, and a semisolid preparation such as an ointment and a gel.

A solid preparation may generally be used by oral administration or by percutaneous or by environmental application after dilution with water or the like. A solid preparation can be prepared by mixing an active ingredient with an appropriate vehicle, and with an adjuvant if necessary, and formulating the mixture into a desired dosage form. Examples of the vehicle include an inorganic vehicle such as a carbonate, a hydrogen carbonate, a phosphate, aluminum oxide, silica or clay or an organic vehicle such as a saccharide, cellulose, cereal flour or starch.

An injection fluid may be administered intravenously, intramuscularly or subcutaneously. An injection fluid can be prepared by dissolving an active ingredient in an appropriate solvent and, if necessary, adding additives such as a solubilizer, an acid, a base, a buffering salt, an antioxidant and a protectant. Examples of appropriate solvents include water, ethanol, butanol, benzyl alcohol, glycerin, propylene glycol, polyethylene glycol, N-methylpyrrolidone and mixtures thereof, physiologically acceptable vegetable oils and synthetic oils suitable for injection. Examples of solubilizers include polyvinylpyrrolidone, polyoxyethylated castor oil, polyoxyethylated sorbitan ester and the like. Examples of protectants include benzyl alcohol, trichlorobutanol, p-hydroxybenzoic acid esters, n-butanol and the like.

An oral liquid may be administered directly or after dilution and can be prepared in the same manner as an injection fluid.

A flowable, an emulsion or the like may be administered directly or after dilution percutaneously or by environmental application.

A liquid preparation applied to the skin is administered by dripping, spreading, rubbing, spraying, sprinkling or dipping (soaking, bathing or washing) and can be prepared in the same manner as an injection fluid.

A pour-on preparation and a spot-on preparation are dripped or sprayed to a limited area of the skin so that they permeate through the skin and act systemically. A pour-on preparation and a spot-on preparation can be prepared by dissolving, suspending or emulsifying an active ingredient in an appropriate skin-friendly solvent or solvent mixture. If necessary, additives such as a surfactant, a colorant, an absorbefacient, an antioxidant, a light stabilizer and an adhesive may be added. Examples of appropriate solvents include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone or 2,2-dimethyl-4-oxymethylene-1,3-dioxolane. Examples of absorbefacients include DMSO, isopropyl myristate, pelargonic acid dipropylene glycol, silicone oil, fatty acid esters, triglycerides and aliphatic alcohols. Examples of antioxidants include sulfites, metabisulfites, ascorbic acid, butylhydroxytoluene, butylhydroxyanisole and tocopherol.

An emulsion may be administered orally, percutaneously or by injection. An emulsion can be prepared by dissolving an active ingredient in a hydrophobic phase or a hydrophilic phase and homogenizing the resulting solution with another liquid phase together with an appropriate emulsifier, and further if necessary with additives such as a colorant, an absorbefacient, a protectant, an antioxidant, a light screen and a thickner.

Examples of hydrophobic phases (oils) include paraffin oil, silicone oil, sesame oil, almond oil, castor oil, synthetic triglycerides, ethyl stearate, di-n-butyryl adipate, hexyl laurate, pelargonic acid dipropylene glycol, esters of branched short-chain fatty acids with $C_{16}$-$C_{18}$ saturated fatty acids, isopropyl myristate, isopropyl palmitate, esters of $C_{12}$-$C_{18}$ saturated alcohols with caprylic/capric acid, isopropyl stearate, oleyl oleate, decyl oleate, ethyl oleate, ethyl lactate, fatty acid ester waxes, dibutyl phthalate, diisopropyl adipate, isotridecyl alcohol, 2-octyldodecanol, cetylstearyl alcohol and oleyl alcohol.

Examples of hydrophilic phases include water, propylene glycol, glycerin and sorbitol.

Examples of emulsifiers, nonionic surfactants include polyoxyethylated castor oil, polyoxyethylated sorbitan monoolefinic acid, sorbitan monostearate, glycerin monostearate, polyoxyethyl stearate and alkyl phenol polyglycol ether; amphoteric surfactants such as disodium N-lauryl-β-iminodipropionate and lecithin; anionic surfactants such as sodium lauryl sulfate, aliphatic alcohol sulfate ether, mono/dialkylpolyglycol orthophosphate monoethanolamine salt; and cationic surfactants such as cetyltrimethylammonium chloride.

Examples of other additives include carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, waxes and colloidal silica.

A semisolid preparation is administered by applying or spreading onto the skin or introducing into the coelom. A gel can be prepared by adding a thickener to a solution prepared in the same manner as an injection fluid sufficiently to give a transparent viscous substance like an ointment.

In the case where the endoparasite control agent of the present invention is used as a pharmaceutical for animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight. Such a dose may be given as a single dose or divided into multiple doses.

The concentration of the active ingredient in the endoparasite control agent of the present invention is generally about 0.001 to 100% by mass, preferably about 0.001 to 99% by mass, and more preferably about 0.005 to 20% fey mass. The endoparasite control agent of the present invention may be a composition that can be directly administered, or a highly concentrated composition that needs to be diluted to a suitable concentration before use.

The endoparasite control agent of the present Invention can be used in combination with any existing endoparasite control agent for the purpose of reinforcing or complementing its effect. In such a combined use, two or more active ingredients may be mixed and formulated into a single preparation before administration, or two or more different preparations may be administered separately.

The agricultural and horticultural insecticidal and acaricidal agent comprising the benzimidazole compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticidal and acaricidal agent is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticidal and acaricidal agent utilizes so-called penetration and translocation. That is, nursery soil, soil in transplanting holes, plant foot, irrigation water, cultivation water in hydroponics, or the like is treated with the agricultural and horticultural insecticidal and acaricidal agent to allow crops, ornamental flowering plants, etc. to absorb the compound of the present invention through the roots via soil or otherwise.

Examples of useful plants to which the agricultural and horticultural insecticidal and acaricidal agent of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, *sorghum*, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticidal and acaricidal agent of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticidal and acaricidal agent of the present invention can be used in combination or used systematically.

In order to control target pests, the agricultural and horticultural insecticidal and acaricidal agent of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticidal and acaricidal agent of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticidal and acaricidal agent of the present invention is commonly used as a formulation convenient for application, which is prepared by the usual method for preparing agrochemical formulations.

That is, the benzimidazole compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticidal and acaricidal agent or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated aliphatic hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one. Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticidal and acaricidal agent of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticidal and acaricidal agent).

The application rate of the agricultural and horticultural insecticidal and acaricidal agent of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticidal and acaricidal agent of the present invention can be used after mixed with other agricultural and horticultural insecticidal and acaricidal agent, acaricides, nematicides, microbicides, biopesticides and/or the like. Further, the agricultural and horticultural insecticidal and acaricidal agent can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), fenobucarb (BPMC), Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, acynonapyr, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isocycloseram, isofenphos, isoprocarb (MIPC), epsilon-metofluthrin, epsilon-momfluorothrin, ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxazosulfyl, oxamyl, oxydemeton-methyl, oxydeprofos (ESP), oxibendazole, oxfendazole, potassium oleate, sodium oleate, cadusafos, kappa-tefluthrin, kappa-bifenthrin, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, chloroprallethrin, kelthane (dicofol), salithion, cyhalodiamide, cyanophos (CYAP), diafenthiuron, diamidafos, cyantraniliprole, theta-cypermethrin, dienochlor, cyenopyrafen, dioxabenzofos, diofenolan, sigma-cypermethrin, cyclaniliprole, dichlofenthion (ECP), cycloprothrin, dichlorvos (DDVP), dicloromezotiaz, disulfoton, dinotefuran, cyhalodiamide, cyhalothrin, cyphenothrin, cyfluthrin, diflubenzuron, cyflumetofen, diflovidazin, cyhexatin, cypermethrin, dimethylvinphos, dimethoate, dimpropyridaz, dimefluthrin, silafluofen, cyromazine, spinetoram, spinosad, spirodiclofen, spirotetramat, spiropidion, spiromesifen, sulfluramid, sulprofos, sulfoxaflor, zeta-cypermethrin, diazinon, tau-fluvalinate, dazomet, thiacloprid, tiaxazafen, thiamethoxam, tioxazafen, thiodicarb, thiocyclam, thiosultap, thiosultap-sodium, thionazin, thiometon, deet, dieldrin, tetrachlorantraniliprole, tyclopyrazoflor, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, doramectin, tralopyril, tralomethrin, transfluthrin, triazamate, triazuron, trichlamide, trichlorphon (DEP), triflumezopyrium, triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, pyflubumide, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pyriminostrobin, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazaindolizine, fluazinam, fluazuron, fluensulfone, fluxametamide, flucycloxuron, flucythrinate, fluvalinate, flupyradifurone, flufiprole, flupyrazofos, flupyrimin, flufenerim, flufenoxystrobin, flufenoxuron, flufenzine, flufenprox, fluproxyfen, flubrocythrinate, fluhexafon, flubendiamide, flumethrin, flurimfen, prothiofos, protrifenbute, flonicamid, propaphos, propargite (BPPS), profenofos, broflanilide, profluthrin, propoxur (PHC), flometoquin, alpha-bromadiolone, bromopropylate, beta-cyfluthrin, hexaflumuron, hexythiazox, heptafluthrin, heptenophos, permethrin, benclothiaz, bendiocarb, benzpyrimoxan, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, momfluorothrin, lambda-cyhalothrin, ryanodine, lufenuron, rescalure, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate, and salts thereof.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, aminopyrifen, ampropylfos, ametoctradin, allyl alcohol, aldimorph, amobam, isotianil, isovaledione, isopyrazam, isofetamid, isoflucypram, isoprothiolane, ipconazole, ipfentrifluconazole, ipflufenoquin, iprodione, iprovalicarb, iprobenfos, imazalil, iminoctadine, metam, iminoctadine-albesilate, iminoctadine-triacetate, imibenconazole, inpyrfluxam, uniconazole, uniconazole-P, echlomezole, edifenphos, etaconazole, ethaboxam, ethirimol, etem, ethoxyquin, etridiazole, enestroburin, enoxastrobin, epoxiconazole, oxadixyl, oxathiapiprolin, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinofumelin, chinomethionat, quinomethionate, captafol, captan, kiralaxyl, quinconazole, quintozene, guazatine, cufraneb, cuprobam, coumoxystrobin, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, salicylanilide, zarilamid, cyazofamid, diethyl pyrocarbonate, diethofencarb, cyclafuramid, diclocymet, dichlozoline, diclobutrazol, dichlofluanid, cycloheximide, dichlobentiazox, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipymetitrone, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, ziram, silthiofam, streptomycin, spiroxamine, sultropen, sedaxane, zoxamide, dazomet, thiadiazin, tiadinil, thiadifluor, thiabendazole, tioxymid, thioquinox, thiochlorfenphim, thiophanate, thiophanate-methyl, thifluzamide, thicyofen, thioquinox, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, triclopyricarb, tricyclazole, triticonazole, tridemorph, tributyltin oxide, triflumizole, trifloxystrobin, triforine, tolylfluanid, tolclofos-methyl, tolprocarb, natamycin, nabam, nitrostyrene, nitrothal-isopropyl, nuarimol, copper nonylphenol sulfonate, halacrinate, validamycin, valifenalate, harpin protein, picarbutrazox, bixafen, picoxystrobin, picobenzamide, pydiflumetofen, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyraziflumid, pyrazophos, pyrapropoyne, pyrametostrobin, pyriofenone, pyridinitril, pyrifenox, pyrisoxazole, pyridachlometyl, pyrifenox, pyribencarb, pyriminostrobin, pyrimethanil, pyroxychlor, pyroxyfur, pyroquilon, vinclozolin, ferbam, famoxadone, fenapanil, fenamidone, fenaminosulf, fenaminstrobin, fenarimol, fenitropan, fenoxanil, ferimzone, ferbam, fentin, fenpiclonil, fenpicoxamid, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluindapyr, fluoxastrobin, fluoxapiprolin, fluotrimazole, fluopicolide, fluopimomide, fluopyram, fluoroimide, furcarbanil, fluxapyroxad, fluquinconazole, furconazole, furconazole-cis, fludioxonil, flusilazole, flusulfamide, flutianil, flutolanil, flutriafol, flufenoxystrobin, furfural, furmecyclox, flumetover, flumorph, proquinazid, prochloraz, procymidone, prothiocarb, prothioconazole, pronitridine, propamocarb, propiconazole, propineb, furophanate, probenazole, bromuconazole, florylpicoxamid, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, benzovindiflupyr, bentaluron, benthiazole, benthiavalicarb, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, mandestrobin, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metyltetraprole, metconazole, metsulfovax, methfuroxam, metominostrobin, metrafenone, mepanipyrim, mefenoxam, mefentrifluconazole, meptyldinocap, mepronil, mebenil, iodomethane, rabenzazole, methyl bromide, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate, and salts thereof.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorphthalim, chlorflurazole, chlorflurenol, chlorprocarb, chlorpropham, chlormequat, chloreturon, chloroxynil, chloroxuron, chlorotoluron, chloropon, saflufenacil, cyanazine, cyanatryn, di-allate, diuron, diethamquat, dicamba, cycluron, cycloate, cycloxydim, diclosulam, cyclosulfamuron, cyclopyranil, cyclopyrimorate, dichlorprop, dichlorprop-P, dichlobenil, diclofop, diclofop-methyl, dichlormate, dichloralurea, diquat, cisanilide, disul, siduron, dithiopyr, dinitramine, cinidonethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, tiafenacil, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetflupyrolimet, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, trifludimoxazin, triflusulfuron, triflusulfuron-methyl, trifluralin, trifloxysulfuron, tripropindan, tribenuron, tribenuron-methyl, trifop, trifopsime, trimeturon, tolpyralate, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, haloxyfop, haloxyfop-P, haloxyfop-methyl, halosafen, halosulfuron, halosulfuron-methyl, bilanafos, bixlozone, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, butroxydim, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromomobonil, florasulam, florpyrauxifen, hexachloroacetone, hexazinone, pethoxamid, benazolin, penoxsulam, pebulate, beflubutamid, beflubutamid-M, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, lancotrione, linuron, rimsulfuron, lenacil, rhodethanil, calcium peroxide and methyl bromide, and salts thereof.

Examples of the biopesticide include *Agrobacterium radiobacter* (e.g., Galltrol-A (registered trademark) manufactured by AgBioChem, CA using strain K84 and Nogall (registered trademark) manufactured by Becker Underwood, US using strain K1026), *Agrobacterium radiobacter* (e.g., Bacterose (registered trademark) manufactured by NIHON NOHYAKU Co., Ltd. using strain 84), *Ampelomyces quisqualis* (e.g., AQ 10 (registered trademark) manufactured by IntrachemBio Italia & Co. KG using strain AQ10), *Aspergillus flavus* (e.g., Afla-Guard (registered trademark) manufactured by Syngenta and AF36 (registered trademark)

manufactured by Arizona Cotton Research and Protection Council, US using strain AF36 and Afla-Guard manufactured by Syngenta using strain NRRL 21882), *Aureobasidium pullulans* (e.g., Botector (registered trademark), a mixture of blastospores of strain DSM14940 and blastospores of strain DSM14941, manufactured by bio-ferm, GmbH), *Bacillus amyloliquefaciens* (e.g., Impression Clear (registered trademark) manufactured by Idemitsu Agri using strain AT-332, Avogreen (registered trademark) manufactured by University of Pretoria using strain B246, Bacstar (registered trademark) manufactured by Etec Crop Solutions, NZ using strain D747, Shelter (registered trademark) manufactured by Dagutat Bio lab, ZA using strain DB101, Artemis (registered trademark) manufactured by Dagutat Bio lab, ZA using strain DB102, RhizoVital (registered trademark) manufactured by ABiTEP, DE using strain FZB42, Kodiak (registered trademark) manufactured by Bayer Crop Science AG, DE using strain GB03, Subtilex (registered trademark) manufactured by Becker Underwood, US using strain MBI600 and Amplitude manufactured by Marrone Bio Innovations, Inc. using strain F727), *Bacillus cepacia* (e.g., Deny Stine (registered trademark) manufactured by Microbial Products), *Bacillus cereus* (e.g., Mepichlor (registered trademark) manufactured by Arysta, US using strain BP01), *Bacillus firmus* (e.g., BioNeem (registered trademark) manufactured by AgoGreen using strain 1-1582), *Bacillus lacticola* (e.g., a product manufactured by Micro Flo Company), *Bacillus lactimorbus* (e.g., a product manufactured by Micro Flo Company), *Bacillus lactis* (e.g., a product manufactured by Micro Flo Company), *Bacillus laterosporus* (e.g., Bio-Tode (registered trademark) manufactured by Agro-Organics, SA), *Bacillus licheniformis* (e.g., EcoGuard Biofungicide (registered trademark) manufactured by Novozymes using strain SB3086), *Bacillus maroccanus* (e.g., a product manufactured by Micro Flo Company), *Bacillus megaterium* (e.g., Bioarc (registered trademark) manufactured by Bio Arc using strain YFM3.25), *Bacillus metiens* (e.g., a product manufactured by Micro Flo Company), *Bacillus mojavensis* (e.g., a product manufactured by Probelte, Sa using strain SR11), *Bacillus mycoides* (e.g., BmJ (registered trademark) manufactured by Certis USA using isolate J.), *Bacillus nigrificans* (e.g., a product manufactured by Micro Flo Company), *Bacillus popilliae* (e.g., Cronox (registered trademark) manufactured by Bio Crop, CO), *Bacillus pumilus* (e.g., Integral F-33 (registered trademark) manufactured by Becker Underwood, US using strain BU F-33, Yield Shield (registered trademark) manufactured by Bayer Crop Science AG, DE using strain GB34, and Sonata (registered trademark) manufactured by Bayer Crop Science LP, US using strain QST2808), *Bacillus simplex* (e.g., Momi-Hope W P (registered trademark) manufactured by Arysta LifeScience Corporation using strain CGF2856), *Bacillus sphaericus* (e.g., VectoLex (registered trademark) manufactured by Valent BioSciences, US using serotype H5a5b strain 2362), *Bacillus subtilis* (e.g., Botokiller WP (registered trademark) manufactured by Idemitsu Agri Co., Taegro (registered trademark) manufactured by Novozyme Biologicals, Inc. US using strain FZB24, SERENADE MAX (registered trademark) manufactured by Bayer Crop Science LP, US using strain QST713/AQ713, Serenade-DPZ (registered trademark) using strain AQ30002, EcoShot (registered trademark) manufactured by KUMIAI CHEMICAL INDUSTRY Co., Ltd. using strain D747, Agrocare WP (registered trademark) manufactured by Nisso Green Co., Ltd. using strain HAI-0404, Botopika WP (registered trademark) manufactured by Idemitsu Kosan Co., Ltd. using strain MBI600, BaciStar WP (registered trademark) manufactured by Arysta LifeScience Corporation using strain Y1336, and Companion Biological Fungicide Wettable Powder manufactured by A Growth Products Ltd. using strain GB03), *Bacillus thuringiensis* (e.g., VectoBac (registered trademark) manufactured by Valent BioSciences, US using strain AM65-52), *Bacillus thuringienses aizawai* (e.g., XenTari (registered trademark) manufactured by Bayer Crop Science AG, DE using strain ABTS-1857, Florbac W G (registered trademark) manufactured by Valent BioSciences, US using serotype H-7, and Agree WG Biological Insecticide manufactured by Certis USA, US using serotype GC-91), *Bacillus thuringiensis subspecies. Aegypti* (e.g., Agerin (registered trademark)), *Bacillus thuringienses israelensis* (e.g., Aquabac (registered trademark) manufactured by Becker Microbial Products IL using strain BMP144), *Bacillus thuringienses kurstaki* (e.g., a product manufactured by Becker Microbial Products, IL using strain BMP 123, Dipel ES (registered trademark) manufactured by Valent BioSciences, US using strain HD-1, BMP 123 manufactured by Becker Microbial Products using strain BMP123, BMP144/Aquabac manufactured by Becker Microbial Products using strain BMP144, Dipel 10G manufactured by Valent U.S.A. LLC. using strain ABTS-351, Condor Wettable Powder manufactured by Certis USA using strain EG2348, Crymax Bioinsecticide manufactured by Certis USA using strain EG7841, Deliver Biological Insecticide manufactured by Certis USA using strain SA-12, and Bioprotec PLUS manufactured by AEF Global using strain EVB-113-19), *Bacillus thuringiensis galleriae* (e.g., beetleGONE! manufactured by Phyllom BioProducts, and boreGONE! manufactured by Phyllom BioProducts using strain SDS-502), *Bacillus thuringiensis var. colmeri* (e.g., TianBaoBTc (registered trademark) manufactured by Changzhou Jianghai Chemical Factory), *Bacillus thuringienses tenebrionis* (e.g., Novodor FC (registered trademark) manufactured by BioFa DE using strain NB 176), *Bacillus thuringiensis var. san diego* (e.g., M-One (registered trademark) from *Bacillus thuringiensis* var. san diego), *Beauveria bassiana* (e.g., Naturalis (registered trademark) manufactured by Intrachem Bio Italia, Bove Max (registered trademark) manufactured by Novozymes using strain CG716, BioLisa Madara (registered trademark) manufactured by Idemitsu Kosan Co., Ltd. using strain F-263, BotaniGard WP (registered trademark) manufactured by ARYSTA using strain GHA, balEnce manufactured by Terragena, Inc. using strain HF23, BotaniGard ES manufactured by BioWorks Inc. using strain GHA, and BioCeres WP manufactured by BioSafe Systems, Inc. using strain ANT-03), *Beauveria brongniartii* (e.g., Beaupro (registered trademark) manufactured by Andermatt Biocontrol AG), *Bradyrhizobium japonicum* (e.g., Optimize (registered trademark) manufactured by Novozymes), *Burkholderia* spp. (e.g., MBI-206 TGAI (registered trademark) manufactured by Marrone Bio Innovations using strain A396), *Candida oleophila* (e.g., Aspire manufactured by Ecogen Inc., US using strain 1-82 and Nexy manufactured by BioNext using strain 0), *Candida saitoana* (e.g., BIOCURE (registered trademark) manufactured by Micro Flo Company, US (BASF SE)), *Chaetomium cupreum* (e.g., BIOKUPRUM (registered trademark) manufactured by AgriLife), *Chaetomium globosum* (e.g., Rivadiom (registered trademark) manufactured by Rivale), *Chromobacterium subtsugae* (e.g., Grandevo (registered trademark) manufactured by Marrone Bio Innovations using strain PRAA4-1T), *Cladosporium cladosporioides* (e.g., from *Cladosporium cladosporioides*), *Clonostachys rosea f. catenulate* (e.g., PRESTOP (registered trademark) manufactured by Verdera, Finland using strain J1446), *Colletotrichum gloeosporioides* (e.g., Collego (registered trademark) manufactured by Agriultural Research Initiatives), *Coniothyrium minitans* (e.g., Contans (registered trademark) manufactured by Encore Technologies, LLC using strain CON/M/91-08), *Cryptococcus albidus* (e.g., YieldPlus (registered trademark) manufactured by Anchor Bio Technologies, ZA), *Delftia acidovorans* (e.g., BioBoost (registered trademark) manufactured by Brett Young Seeds using strain RAY209), *Dilophosphora alopecuri* (e.g., Twist Fungus (registered trademark)), *Drechsrela monoceras* (e.g., Tasumato herbicide (registered trademark) manufactured by Mitsui Chemicals Agro, Inc. using strain MTB-951), *Entomophthora virulenta* (e.g., Vektor (registered trademark) manufactured by Ecomic),
*Fusarium oxysporum* (e.g., Maruka light manufactured by Eisai Seikaken, Inc. using strain 101-2), *Fusarium oxysporum* (e.g., Fusaclean (registered trademark) manufactured by Natural Plant Protection using strain Fo47), *Gliocladium* spp. (e.g., Prestop (registered trademark) manufactured by AgBio Inc. using strain J1446 and a product manufactured by W.F. Stoneman Company LLC using strain 321U), *Hirsutella thompsonii* (e.g., Mycohit (registered trademark) manufactured by Agro Bio tech Research Centre, IN), *Lactobacillus acidophilus* (e.g., Fruitsan (registered trademark) manufactured by Inagrosa Industrias Agrobiologicas, S.A.), *Lactobacillus plantarum* (e.g., Lactoguard WP manufactured by Meiji Seika Pharma Co., Ltd. using strain BY), *Lecanicillium lecanii* (e.g., Mycotal (registered trademark) manufactured by Koppert/Arysta using conidiospores of strain KV01), *Metarhizium anisopliae* (e.g., BIO 1020 (registered trademark) manufactured by Bayer Crop Science using strain F52, Pirates G (registered trademark) manufactured by Arysta LifeScience Corporation using strain SMZ-2000, and Bio-Blast manufactured by LidoChem Inc using strain ESC1), *Metarhizium anisopliae* var. *acridum* (e.g., Green Muscle (registered trademark) manufactured by Biological Control Products and GreenGuard (registered trademark) manufactured by Becker Underwood, US), *Metschnikowia fructicola* (e.g., Shemer (registered trademark) manufactured by Bayer Crop Science), *Microdochium dimerum* (e.g., ANTIBOT (registered trademark) manufactured by Agrauxine, France), *Microsphaeropsis ochracea* (e.g., Microx (registered trademark) manufactured by Prophyta), *Monacrosporium phymatopagum* (e.g., Nemahiton (registered trademark) manufactured by Tomoe Kagaku Kogyo K. K.), *Mucor haemelis* (e.g., BioAvard (registered trademark) manufactured by Indore Biotech Inputs & Research), *Muscodor albus* (e.g., Arabesque manufactured by Bayer Crop Science using strain QST 20799), *Myrothecium verrucaria* (e.g., DiTera (registered trademark) manufactured by Valent Biosciences using strain AARC-0255), *Paecilomyces fumosoroseus* (e.g., PreFeRal (registered trademark) WG manufactured by Biobest using strain apopka 97, Preferred WP manufactured by Tokai Bussan Co. Ltd., and No Fly (registered trademark) manufactured by Natural Industries Inc. (Novozymes company) using strain FE 9901), *Paecilomyces lilacinus* (e.g., BioAct WG (registered trademark) manufactured by Prophyta using strain 251), *Pacilimyces tenuipes* (e.g., Gottu A manufactured by Idemitsu Kosan Co., Ltd. using strain T1), *Paecilomyces variotii* (e.g., Nemaquim (registered trademark) manufactured by Quimia, M X using strain Q-09), *Paenibacillus polymyxa* (e.g., Topseed (registered trademark) manufactured by Green Biotech Company Ltd. using strain AC-1), *Paenibacillus poppiliae* (e.g., Milky spore disease (registered trademark) manufactured by St. Gabriel Laboratories), *Pasteuria nishizawae* (e.g., oyacyst LF/ST (registered trademark) manufactured by Pasteuria Bioscience, and *Clariva pn* manufactured by Syngenta using strain Pn1), *Pasteuria penetrans* (e.g., Pasteuria (registered trademark) manufactured by Pasteuria Bioscience), *Pasteuria usagae* (e.g., Econem (registered trademark) manufactured by Pasteuria Bioscience), *Pantoea agglomerans* (e.g., Bloomtime Biological FD Biopesticide manufactured by Nufarm U S using strain E325), *Pectobacterium carotovorum* (e.g., Biokeeper (registered trademark) manufactured by Nissan Chemical Corporation and EcoMate (registered trademark) manufactured by KUMIAI CHEMICAL INDUSTRY Co., Ltd. using CGE234M403), *Phoma macrostroma* (e.g., Phoma H (registered trademark) manufactured by Scotts, US using strain 94-44B), *Penicillium bilaii* (e.g., Jump Start (registered trademark) manufactured by Novozymes), *Phlebiopsis gigantea* (e.g., ROTSOP (registered trademark) manufactured by Verdera, Finland using strain FOC PG B22/SP1190/3.2), *Pochonia chlamydosporia* var. *catenulata* (e.g., KlamiC (registered trademark) manufactured by The National Center of Animal and Plant Health (CENSA); CU), *Pseudomonas aureofaciens* (e.g., Spot-Less Biofungicide (registered trademark) manufactured by Eco Soils Systems, CA using strain TX-1), *Pseudomonas chlororaphis* (e.g., ATEze (registered trademark) manufactured by EcoSoil Systems using strain 63-28 and Cedomon (registered trademark) manufactured by Bioagri, S. using strain MA 342), *Pseudomonas fluorescens* (e.g., Frostban D (registered trademark) manufactured by Frost Technology Corp. using strain 1629RS, Blightban (registered trademark) manufactured by Blightban using strain A506, Konae Fukudo (registered trademark) manufactured by Taki Chemical Co., Ltd. using strain FPT-9601, Cell Nae Genki (registered trademark), a mixture of strains FPT-9601 and FPH-9601, manufactured by Taki Chemical Co., Ltd., and Vegikeeper (registered trademark) manufactured by Arysta LifeScience Corporation using strain G7090), *Pseudomonas proradix* (e.g., Proradix (registered trademark) manufactured by Sourcon Padena), *Pseudomonas resinovorans* (e.g., Solanacure (registered trademark) manufactured by Agricultural Research Council, SA), *Pseudomonas syringae* (e.g., Biosave (registered trademark) manufactured by EcoScience, US using strain MA-4, Frostban C (registered trademark) manufactured by Frost Technology Corp using strain 742RS, Bio-save 10LP Biological Fungicide manufactured by Jet Harvest Systems using strain ESC10, Bio-Save 11 LP Biological Fungicide manufactured by Jet Harvest Systems using strain ESC11), *Pseudomonas* spp. (e.g., Masterpiece WP (registered trademark) manufactured by Nippon Soda Co., Ltd. using strain HAI-0804 and Momi-Genki WP manufactured by Nissan Chemical Corporation using strain CAB-02), *Pseudozyma aphidis* (e.g., a product manufactured by Yissum Research Development Company of the Hebrew University of Jerusalem), *Pseudozyma flocculosa* (e.g., Sporodex L manufactured by Plant Products Co. Ltd., CA using strain PF-A22 UL), *Pythium oligandrum* (e.g., Polyversum (registered trademark) manufactured by Biopreprary, CZ using strain DV74 or strain M1), *Reynoutria sachlinensis* (e.g., REGALIA (registered trademark) manufactured by Marrone BioInnovations, US), *Rhizopogon amylopogon* (e.g., Myco-Sol (registered trademark) manufactured by Helena Chemical Company), *Rhizopogon fulvigleba* (e.g., Myco-Sol (registered trademark) manufactured by Helena Chemical Company), *Saccharomyces cerevisiae* (e.g., a product manufactured by Lesaffre et Compagnie, F R), *Sclerotinia minor* (e.g., Sarritor (registered trademark) manufactured by Agrium Advanced Technologies), *Serratia entomophila* (e.g., Invade (registered trademark) manufactured by Wrightson Seeds), *Sporothrix insectorum* (e.g., Sporothrix Es (registered trademark) manufactured by Biocerto, B R), *Steinernema carpocapsae* (e.g., Biosafe (registered trademark) manufactured by SDS Biotech K. K.), *Steinernema kushidai* (e.g., Shibaichi-Nema manufactured by Kubota Corporation), *Steinernema glaseri* (e.g., Biotopia (registered trademark) manufactured by Arysta LifeScience Corporation), *Streptomyces acidiscabies* (e.g., MBI-005EP (registered trademark) manufactured by Marrone Bioinnovations, CA using strain RL-110T), *Streptomyces candidus* (e.g., BioBac (registered trademark) manufactured by Biontech, TW using strain Y21007-2), *Streptomyces galbus* (e.g., Mycostop (registered trademark) manufactured by Verdera using strain K61), *Streptomyces lydicus* (e.g., ACTINOVATE (registered trademark) manufactured by Natural Industries, US using strain WYEC108), *Streptomyces saraceticus* (e.g., Clanda (registered trademark) manufactured by A & A Group (Agro Chemical Corp.)), *Talaromyces flavus* (e.g., Momi-keeper (registered trademark) manufactured by Central Glass Co., Ltd. using strain B-422, Tough Block (registered trademark) manufactured by Idemitsu Kosan Co., Ltd. using strain SAY-Y-94-01, and PROTUS (registered trademark) WG manufactured by Prophyta, DE using strain V117b), *Trichoderma asperellum* (e.g., a product manufactured by Isagro using strain ICC 012, T34 Biocontrol (registered trademark) manufactured by Bioncontrol Technologies, ES using strain T34, and Eco-Hope (registered trademark) manufactured by KUMIAI CHEMICAL INDUSTRY Co., Ltd. using strain SKT-1), *Trichoderma atroviride* (e.g., Esquive (registered trademark) WP manufactured by Agrauxine, FR, Tenet (registered trademark) or SENTINEL (registered trademark) manufactured by Agrimm Technologies Ltd, NZ each using strain LC52, and EcoHope DJ (registered trademark) manufactured by KUMIAI CHEMICAL INDUSTRY Co., Ltd. using strain SKT-1), *Trichoderma gamsii* (e.g., BIO-TAM (registered trademark) manufactured by Bayer Crop Science LP, US), *Trichoderma harzianum* (e.g., T-Gro 7456 (registered trademark) manufactured by Dagutat Biolab using strain DB 103, Trianum-P (registered trademark) manufactured by Koppert using strain ITEM908, Trichoplus (registered trademark) manufactured by Biological Control Products, SA using strain KD, and ROOT PRO (registered trademark) manufactured by Mycontrol Ltd. using strain TH-35), *Trichoderma harzianum Rifai* (e.g., PLANT-SHIELD T-22G (registered trademark) manufactured by Firma BioWorks Inc, US using strain T-22 and TRICHO-DEX (registered trademark) manufactured by Makhteshim Ltd, US using strain T-39), *Trichoderma lignorum* (e.g., Mycotric (registered trademark) manufactured by Futureco Bioscience, ES using strain TL-0601), *Trichoderma polysporum* (e.g., Binab TF WP (registered trademark) manufactured by BINAB Bio-Innovation AB, Sweden), *Trichoderma stromaticum* (e.g., TRICOVAB (registered trademark) manufactured by Ceplac, Brazil), *Trichoderma virens* (e.g., SOILGARD (registered trademark) manufactured by Certis LLC, US using strain GL-21), *Trichoderma viride* (e.g., REMEDIER (registered trademark) WP manufactured by Isagro Ricerca, ITALIA using strain ICC080 and Trianum-P (registered trademark) manufactured by Koppert using strain TV1), *Tsukamurella paurometabola* (e.g., HeberNem (registered trademark) using strain C-924), *Uloclandium oudemansii* (e.g., Botry-Zen (registered trademark) manufactured by Botry-Zen Ltd, NZ using strain HRU3, and BotryStop manufactured by BioWorks Inc. using strain U3), *Variovorax paradoxus* (e.g., Fieldkeeper WP (registered trademark) manufactured by Central Glass using strain CGF4526), *Vesicular-Arbuscular* (VA) mycorrhizal fungi (e.g., Dr. Kinkon (registered trademark) manufactured by Idemitsu Agri), *Verticillium alboatrum* (e.g., Dutch Trig (registered trademark) manufactured by Tree Care Innovations using strain WCS850), *Verticillium lecanii* (e.g., Vertalec (registered trademark) manufactured by Arysta LifeScience Corporation using strain IMI 179172 and Mycotal (registered trademark) manufactured by Arysta LifeScience Corporation using strain IMI 263817), *Xanthomonas campestris* (e.g., Camperico L (registered trademark) manufactured by Taki Chemical), *Xanthomonas campestris pv. poae, Heterorhabditis bacteriophora, Steinernema feltiae, Steinernema kraussei, Steinernema riobrave*, and *Steinernema scapterisci*; and insecticidal and microbicidal strains selected from mutants of the above-listed strains that each have its original distinguishing characteristics, and metabolites that are produced by the above-listed strains and active against plant pathogenic microbes.

Further examples include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Reference Example 1

Production Method of 4-heptafluoroisopropyl imidazole

[Formula 23]

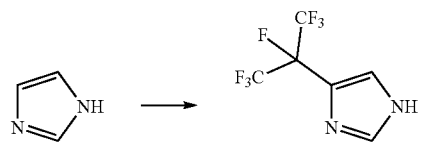

Imidazole (1.0 g, 15 mmol) was dissolved in ethyl acetate (25 mL), and water (25 mL), potassium carbonate (6.1 g, 44 mmol), heptafluoroisopropyl iodide (3.1 mL, 22 mmol), and sodium dithionite (1.3 g, 7.4 mmol) were added thereto at 35° C. The reaction solution was reacted at 35° C. for 3.5 hours, then extracted with ethyl acetate, and the organic layer was dried over magnesium sulfate to distill off the solvent. The obtained crude product was purified by column chromatography thereby to obtain the intended substance (1.3 g, 37%).

Reference Example 2

Production Method of 2-(4-heptafluoroisopropylimidazol-1-yl)benzimidazole

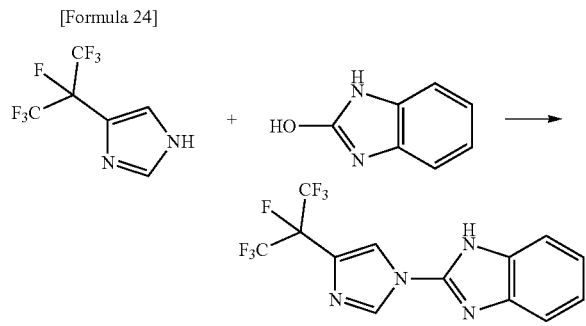

[Formula 24]

4-Heptafluoroisopropyl imidazole (1.27 g, 5.36 mmol), 2-hydroxybenzimidazole (0.863 g, 6.43 mmol), and phosphorus oxychloride (5.00 mL) were refluxed for 5.5 hours. The reaction solution was allowed to cool to room temperature, and then added dropwise to an aqueous solution of 2.0 M sodium hydroxide (100 mL). Subsequently, the solution was neutralized using ammonium chloride and extracted with toluene. The organic layer was dried over magnesium sulfate to distill off the solvent. The obtained crude product was purified by column chromatography thereby to obtain the intended substance (1.28 g, 68%).

Example 1

Production Method of 1-ethanesulfonyl-2-(4-heptafluoroisopropylimidazol-1-yl)benzimidazole (Compound No. 1-22)

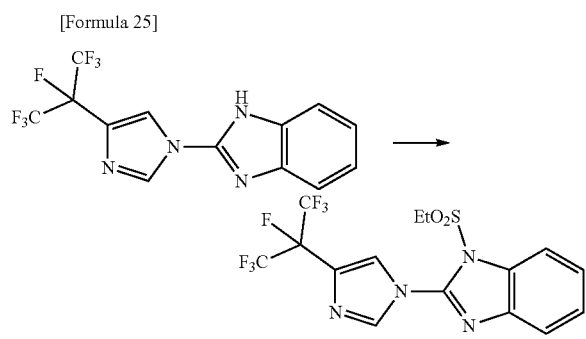

[Formula 25]

2-(4-Heptafluoroisopropylimidazol-1-yl)benzimidazole (985 mg, 2.80 mmol) was dissolved in THF (5.0 mL), and sodium hydride (134 mg, 3.36 mmol) was added in several batches at room temperature. Five minutes later, ethanesulfonyl chloride (449 μL, 4.76 mmol) was added at room temperature and reacted for 4 hours. Subsequently, the reaction was terminated with water, and the reaction solution was extracted with ethyl acetate. The organic layer was dried over magnesium sulfate to distill off the solvent. The obtained crude product was purified using column chromatography thereby to obtain the intended substance (246 mg, 20%).

Reference Example 3

Production Method of 1-methoxymethyl-2-(4-hydroxymethylimidazol-1-yl)benzimidazole

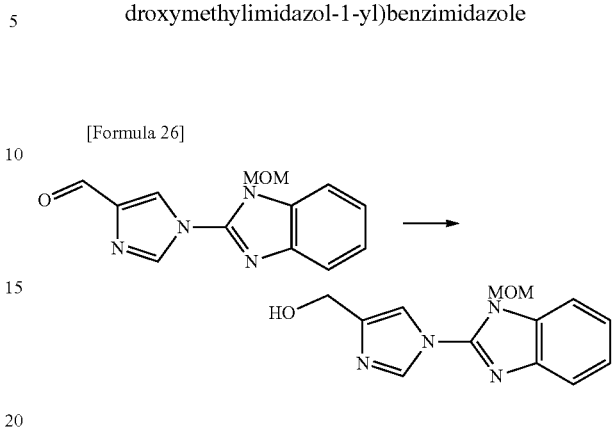

[Formula 26]

1-Methoxymethyl-2-(4-formylimidazol-1-yl) benzimidazole was produced according to the production method of Reference Example 7 using 1-methoxymethyl-2-chlorobenzimidazole produced by MOMCl in place of the SEMCl (2-(trimethylsilyl)ethoxymethylchloride) of Reference Example 12 and 4-formylimidazole. The obtained compound (1.16 g, 4.48 mmol) was dissolved in methanol (10 mL), $NaBH_4$ (339 mg, 8.96 mmol) was added gradually at room temperature and reacted for 1 hour, and then the reaction was terminated with water. The reaction solution was extracted with ethyl acetate thereby to obtain the intended substance (1.04 g, 90%).

Reference Example 4

Production Method of 1-methoxymethyl-2-(4-phenoxymethylimidazol-1-yl)benzimidazole

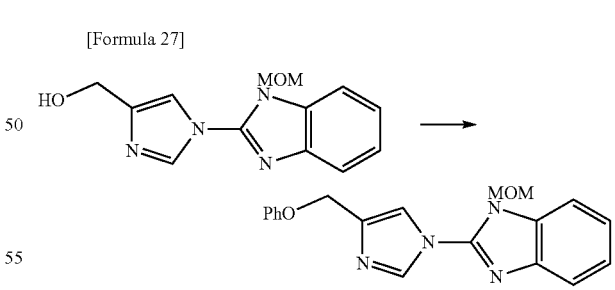

[Formula 27]

1-Methoxymethyl-2-(4-hydroxymethylimidazol-1-yl) benzimidazole (302 mg, 1.17 mmol) was dissolved in toluene (5 mL), triphenylphosphine (399 mg, 1.52 mmol), DEAD (diethyl azodicarboxylate) (691 μL, 1.52 mmol), and phenol (268 μL, 3.04 mmol) were added at 0° C. The reaction solution, at an increased temperature to room temperature, was reacted for 4 hours. The reaction was terminated with water, and the reaction solution was extracted with ethyl acetate thereby to obtain the intended substance.

Reference Example 5

Production Method of 2-(4-phenoxymethylimidazol-1-yl)benzimidazole

[Formula 28]

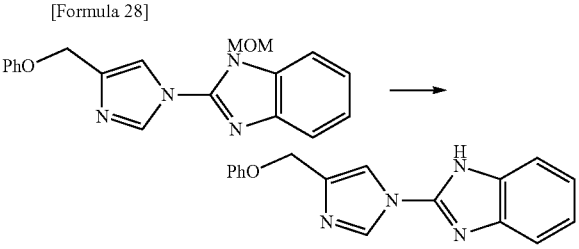

2-(4-Phenoxymethylimidazol-1-yl)benzimidazole was produced by the same method as Reference Example 11.

Example 2

Production Method of 1-ethanesulfonyl-2-(4-phenoxymethylimidazol-1-yl)benzimidazole (Compound No. 1-15)

[Formula 29]

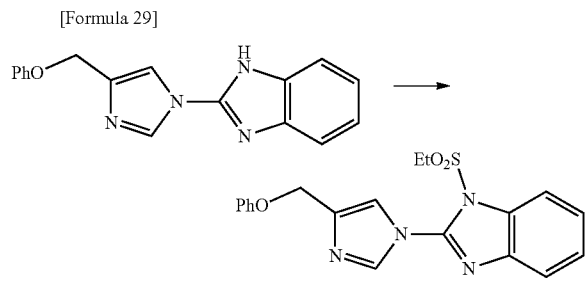

1-Ethanesulfonyl-2-(4-phenoxymethylimidazol-1-yl)benzimidazole was produced by the same method as Example 1.

Reference Example 6

Production Method of t-butyl 3-trifluoromethyl-1H-pyrazole-4-carboxylate

[Formula 30]

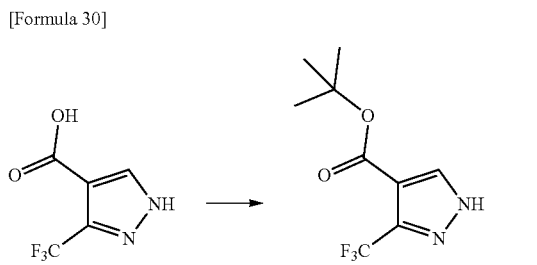

3-Trifluoromethyl-1H-pyrazole-4-carboxylic acid (1.0 g, 5.6 mmol) described in WO2009134750 was dissolved in toluene (28 mL), N,N-dimethylformamide di-t-butyl acetal (6.7 mL, 28 mmol) was added at room temperature. The reaction solution was heated to reflux for 4 hours and then allowed to cool to room temperature. The reaction solution was concentrated, and the obtained crude product was purified by column chromatography thereby to obtain the intended substance (0.89 g, 3.8 mmol, 68%).

Reference Example 7

Production Method of 1-(2-(trimethylsilyl)ethoxymethyl)-2-(4-t-butoxycarbonyl-3-trifluoromethyl-1H-pyrazol-1-yl)benzimidazole

[Formula 31]

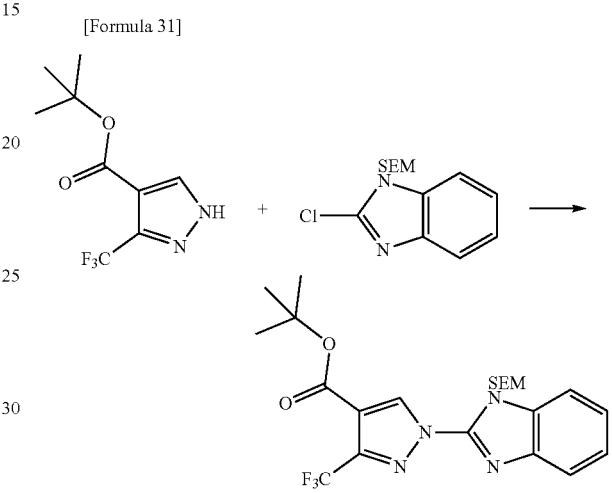

t-Butyl 3-trifluoromethyl-1H-pyrazole-4-carboxylate (1.47 g, 3.05 mmol) was dissolved in NMP (6.0 mL), and 1-(2-(trimethylsilyl)ethoxymethyl)-2-chlorobenzimidazole (1.18 g, 4.16 mmol) produced by the method of Reference Example 12 and potassium carbonate (1.04 g, 7.56 mmol) were added at room temperature. The reaction solution was reacted at 120° C. for 6 hours and then allowed to cool to room temperature. Ethyl acetate and water were added to the reaction solution. The extraction operation was performed with ethyl acetate, and then the organic layer was dried over magnesium sulfate to distill off the solvent. The obtained crude product was purified by column chromatography thereby to obtain the intended substance (1.48 g, 81%).

Reference Example 8

Production Method of 2-(4-t-butoxycarbonyl-3-trifluoromethyl-1H-pyrazol-1-yl) benzimidazole

[Formula 32]

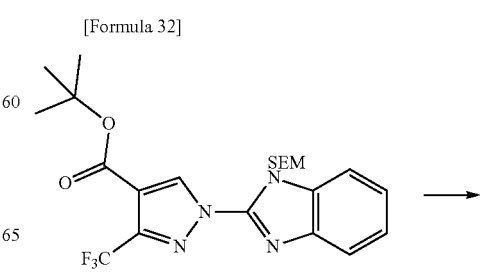

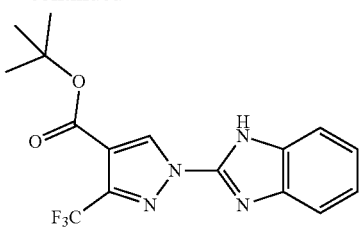

1-(2-(Trimethylsilyl)ethoxymethyl)-2-(4-t-butoxycarbonyl-3-trifluoromethyl-1H-pyrazol-1-yl) benzimidazole (1.47 g, 3.05 mmol) was dissolved in THF/NMP (1:1, 10 mL), TBAF (tetrabutylammonium fluoride) (a 1.0 M THF solution, 6.0 mL, 6.00 mmol) was added at room temperature. The reaction solution was reacted at 90° C. for 3 hours and then allowed to cool to room temperature, and ethyl acetate and water were added to the reaction solution. The extraction operation was performed with ethyl acetate, and then the organic layer was dried over magnesium sulfate to distill off the solvent. The obtained crude product was used for the subsequent reaction as it was.

Example 3

Production Method of 1-ethanesulfonyl-2-(4-t-butoxycarbonyl-3-trifluoromethyl-1H-pyrazol-1-yl) benzimidazole (Compound No. 2-27)

[Formula 33]

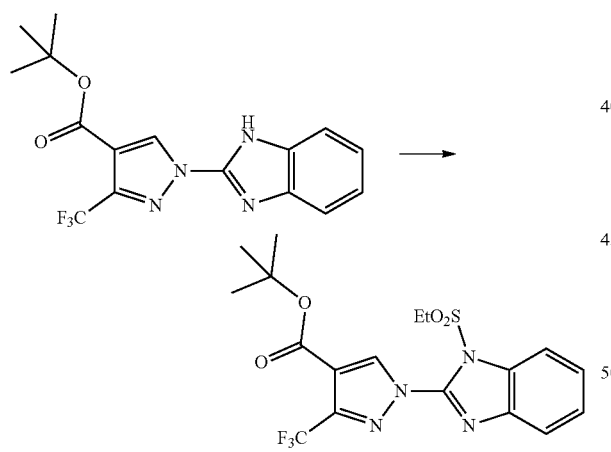

2-(4-t-Butoxycarbonyl-3-trifluoromethyl-1H-pyrazol-1-yl)benzimidazole (1.20 g, 3.41 mmol) was dissolved in THF (10.0 mL), sodium hydroxide (177 mg, 4.43 mmol) was added in several batches at room temperature. Five minutes later, ethanesulfonyl chloride (645 μL, 6.82 mmol) was added at room temperature and reacted for 2 hours. Subsequently, the reaction was terminated with water, and the reaction solution was extracted with ethyl acetate. The organic layer was dried over magnesium sulfate to distill off the solvent. The obtained crude product was purified by column chromatography thereby to obtain the intended substance (266 mg, 18% (2 steps)).

Reference Example 9

Production Method of 4-bromo-3-trifluoromethyl-1H-pyrazole

[Formula 34]

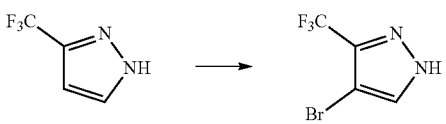

3-Trifluoromethyl-1H-pyrazole (1.4 g, 10 mmol) and DBH (1,3-dibromo-5,5-dimethylhydantoin) (1.7 g, 6.0 mmol) were added to acetonitrile (20 mL) and reacted for 3 hours under reflux. After cooling, the reaction was quenched with a saturated aqueous solution of sodium thiosulfate, neutralized with an aqueous solution of potassium carbonate, and extracted with ethyl acetate. The organic layer was washed with saturated saline solution and dried over sodium sulfate. The solvent was distilled off thereby to obtained the intended substance (2.1 g). The substance was used for the subsequent step without purification.

Reference Example 10

Production Method of 1-methoxymethyl-2-(4-bromo-3-trifluoromethyl-1H-pyrazol-1-yl) benzimidazole

[Formula 35]

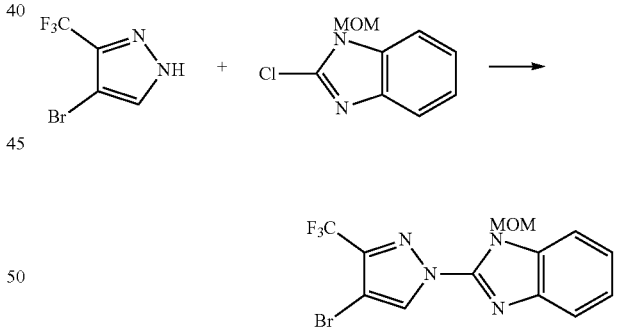

4-Bromo-3-trifluoromethyl-1H-pyrazole (0.54 g, 2.5 mmol), 1-methoxymethyl-2-chlorobenzimidazole (0.49 g, 2.5 mmol) produced by changing SEMCl (2-(trimethylsilyl)ethoxymethylchloride) to MOMCl according to the method of Reference Example 12, and potassium carbonate (1.0 g, 7.5 mmol) were added to NMP (10 mL). The solution was reacted at 120° C. for 3 hours. After cooling to room temperature, water was added, and the reaction solution was extracted with ethyl acetate. The organic layer was washed with a saturated saline solution and dried over sodium sulfate. After distilling off the solvent, the crude product was purified by column chromatography thereby to obtain the intended substance (0.54 g, 54% (2 steps)).

Reference Example 11

Production Method of 2-(4-bromo-3-trifluoromethyl)-1H-pyrazol-1-yl)benzimidazole

[Formula 36]

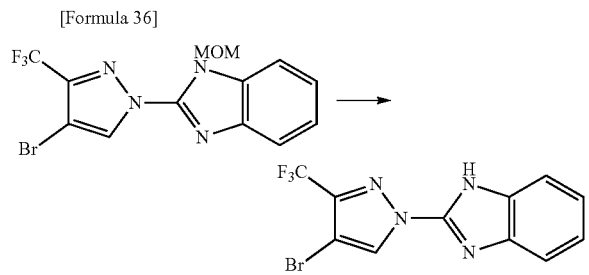

1-Methoxymethyl-2-(4-bromo-3-trifluoromethyl-1H-pyrazol-1-yl)benzimidazole (0.50 g, 1.3 mmol) was added to methanol (20 mL), and concentrated hydrochloric acid (10 mL) was added. Subsequently, the solution was reacted for 2 hours under reflux. After cooling to room temperature, the reaction solution was neutralized by adding an aqueous solution of potassium carbonate and extracted with ethyl acetate. The organic layer was washed with a saturated saline solution and dried over sodium sulfate. The solvent was distilled off to thereby obtain the intended substance (0.36 g, 82%).

Example 4

Production Method of 1-ethanesulfonyl-2-(4-bromo-3-trifluoromethyl)-1H-pyrazol-1-yl)benzimidazole (Compound No. 2-14)

[Formula 37]

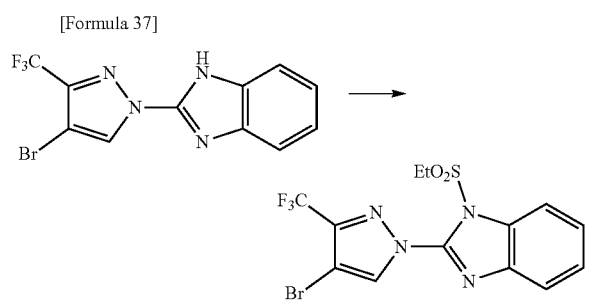

2-(4-Bromo-3-trifluoromethyl-1H-pyrazol-1-yl) benzimidazole (0.15 g, 0.44 mmol) was added to THF (10 mL), and 60% sodium hydride (26 mg, 0.66 mmol) was added. After foaming subsided, ethanesulfonyl chloride (0.11 g, 0.88 mmol) was added dropwise and reacted for 30 minutes. Subsequently, triethylamine (1.0 mL) was added and further reacted for 1 hour. A saturated aqueous solution of ammonium chloride was added to quench the reaction, and reaction solution was extracted with ethyl acetate. The organic layer was washed in the order of triethylamine/water and a saturated saline solution, and dried over sodium sulfate. After distilling off the solvent, the crude product was purified by column chromatography thereby to obtain the intended substance (98 mg, 53%).

Reference Example 12

Production Method of 2-chloro-1-(2-(trimethylsilyl)ethoxymethyl)benzimidazole

[Formula 38]

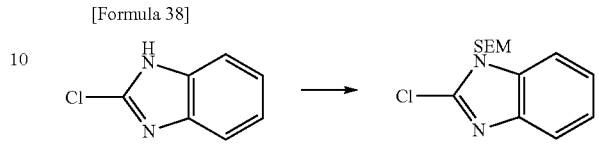

2-Chlorobenzimidazole (10.0 g, 74.6 mmol) was dissolved in DMA (60 mL), and sodium hydride (3.58 g, 89.5 mmol) was added in several batches at room temperature. Five minutes later, SEMCl (2-(trimethylsilyl) ethoxymethylchloride) (17.3 mL, 97.8 mmol) was added at room temperature. After reacting the reaction solution for 3 hours at room temperature, the reaction was terminated with water. The reaction solution was extracted with ethyl acetate, and the organic layer was dried over magnesium sulfate to distill off the solvent. The obtained crude product was purified by column chromatography thereby to obtain the intended substance (16.7 g, 79%).

Hereinafter, formulation examples are shown, but the present invention is not limited thereto. In the formulation examples, "part" means part by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| | |
|---|---|
| Compound of the present invention | 3 parts |
| Clay powder | 82 parts |
| Diatomite powder | 15 parts |

The above ingredients are uniformly mixed and then pulverized to give a dust formulation.

Formulation Example 3

| | |
|---|---|
| Compound of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
|---|---|
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder formulation.

Production Example 5

| Compound of the present invention | 20 parts |
|---|---|
| Polyoxyethylene lauryl ether | 3 parts |
| Sodium dioctyl sulfosuccinate | 3.5 parts |
| Dimethyl sulfoxide | 37 parts |
| 2-Propanol | 36.5 parts |

The above ingredients are uniformly mixed for dissolution to give a water-soluble thickener preparation.

Preparation Example 6

| Compound of the present invention | 2 parts |
|---|---|
| Dimethylsulfoxide | 10 parts |
| 2-Propanol | 35 parts |
| Acetone | 53 parts |

The above ingredients are uniformly mixed for dissolution to give a spray liquid preparation.

Production Example 7

| Compound of the present invention | 5 parts |
|---|---|
| Hexylene glycol | 50 parts |
| Isopropanol | 45 parts |

The above ingredients are uniformly mixed for dissolution to give a liquid preparation for percutaneous administration.

Preparation Example 8

| Compound of the present invention | 5 parts |
|---|---|
| Propylene glycol monomethyl ether | 50 parts |
| Dipropylene glycol | 45 parts |

The above ingredients are uniformly mixed for dissolution to give a liquid preparation for percutaneous administration.

Preparation Example 9

| Compound of the present invention | 2 parts |
|---|---|
| Light liquid paraffin | 98 parts |

The above ingredients are uniformly mixed for dissolution to give a liquid preparation for percutaneous administration (pour-on).

Preparation Example 10

| Compound of the present invention | 2 parts |
|---|---|
| Light liquid paraffin | 58 parts |
| Olive oil | 30 parts |
| ODO-H | 9 parts |
| ShinEtsu Silicone | 1 part |

The above ingredients are uniformly mixed for dissolution to give a liquid preparation for percutaneous administration (pour-on).

Hereinafter, test examples in connection with the present invention are shown, but the present invention is not limited thereto.

Test Example 1

Test for Control Efficacy on Green Peach Aphid (*Myzus persicae*)

Chinese cabbage plants were planted in plastic pots (diameter: 8 cm, height: 8 cm), green peach aphids were propagated on the plants, and the number of surviving Green peach aphids in each pot was counted. The benzimidazole compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

$$\text{Control rate}=100-\{(T\times Ca)/(Ta\times C)\}\times 100 \quad \text{[Expression 1]}$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-4, 1-6, 1-8, 1-12, 1-13, 1-24, 1-25, 1-26, 1-27, 1-30, 1-32, 2-8, 2-10, 2-11, 2-13, 2-15, 2-19, 2-20, 2-24, 2-26, 2-28, 2-34, 2-39, 2-40, 2-43, 2-51, 2-53, 2-54, and 3-1 of the present invention showed the activity level evaluated as D or higher.

Test Example 2

Insecticidal Test on Small Brown Planthopper (*Laodelphax striatellus*)

The benzimidazole compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of small brown planthopper, and then the glass test tubes were capped with cotton plugs. At 8 days after the inoculation, survival rates were calculated from the numbers of surviving larvae and dead larvae, the corrected mortality rate was calculated according to the formula shown below, and the insecticidal efficacy was evaluated according to the criteria shown below.

Corrected mortality rate (%)=(Survival rate in a non-treatment plot−Survival rate in a treatment plot)/(Survival rate in a non-treatment plot)×100 [Expression 2]

Criteria:
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-9, 1-13, 1-22, 1-25, 1-26, 1-27, 1-28, 1-30, 2-12, 2-13, 2-17, 2-18, 2-19, 2-20, 2-21, 2-26, 2-29, 2-32, 2-34, 2-47, 2-48, 2-51, 2-52, 2-53, and 2-54 of the present invention showed the activity level evaluated as D or higher.

Test Example 3

Insecticidal Test on Diamondback Moth (*Plutella xylostella*)

Adults of diamondback moth were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different benzimidazole compound represented by the general formula (1) of the present invention or salt thereof as an active ingredient. After air-dried, the seedlings were kept in a thermostatic chamber at 25° C. At 6 days after the dip treatment, the number of hatched larvae per plot was counted, the corrected mortality rate was calculated according to the formula shown below, and the insecticidal efficacy was evaluated according to the criteria of Test Example 2. This test was conducted in triplicate using 10 adults of diamondback moth per plot.

Corrected mortality rate (%)=(Number of hatched larvae in a non-treatment plot−Number of hatched larvae in a treatment plot)/(Number of hatched larvae in a non-treatment plot)×100 [Expression 3]

As a result, the compounds 1-11, 1-30, 2-3, 2-8, 2-11, 2-18, 2-23, 2-38, 2-39, 2-43, 2-47, 2-48, 2-49, 2-51, and 2-52 of the present invention showed the activity level evaluated as D or higher.

Test Example 4

Acaricidal Action on Two-Spotted Spider Mite (*Tetranychus urticae*)

Leaf disk having a diameter of 2 cm was prepared by leaves of kidney bean, and the leaf disk was placed on the wetted filter paper. Adult hens of two-spotted spider mite were inoculated on the wetted filter paper, and then 50 ml of an agrochemical dispersion, prepared by diluting a formulation containing the benzimidazole compound represented by the general formula (1) of the present invention or salt thereof as an active ingredient to adjust each of the concentrations to 500 ppm, was sprayed on turntable uniformly. After the spraying, it was allowed to stand in a thermostatic chamber at 25° C. Two days after the treatment of an agrochemical dispersion, the dead mites were counted, the corrected mortality rate was calculated according to the formula shown below, and the acaricidal efficacy was evaluated according to the criteria of Test Example 2. This test was conducted in duplicate using 10 adult hens of two-spotted spider per plot.

Corrected mortality(%)=(Number of dead mites in a non-treatment plot−Number of dead mites in a treatment plot)/(Number of dead mites in a non-treatment plot)×100 [Expression 4]

As a result, the compounds 1-2, 1-3, 1-4, 1-5, 1-6, 1-7, 1-8, 1-9, 1-10, 1-11, 1-12, 1-13, 1-14, 1-16, 1-17, 1-18, 1-20, 1-21, 1-22, 1-23, 1-24, 1-25, 1-27, 1-28, 1-31, 1-32, 1-33, 1-36, 1-37, 1-38, 1-39, 1-40, 1-41, 1-42, 1-43, 1-44, 1-45, 1-46, 2-2, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-47, 2-48, 2-49, 2-50, 2-51, 2-52, 2-53, 2-54, 2-55, 2-56, 2-57, 2-58, 2-59, 2-61, 2-62, 2-72, 2-73, 2-74, 2-76, 2-77, 2-78, 2-79, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-122, 2-123, 2-124, 2-125, 2-126, 2-127, 2-128, 2-129, 2-130, 2-131, 2-132, 2-133, 2-134, 2-135, 2-136, 2-137, 2-138, 2-139, 2-140, 2-141, 2-142, 2-143, 2-144, 2-145, 3-1, 3-2, 3-4, 7-1, and 7-6 of the present invention showed the activity level evaluated as D or higher.

Test Example 5

Impact Evaluation Test on Larvae Motility of *Haemonchus* Nematode (*Haemonchus contortus*)

A DMSO dilute solution of the benzimidazole compound represented by the general formula (1) of the present invention or a salt thereof was put in each well of a 96-well plate containing a predetermined prepared solution to give a final concentration of 50 ppm. Twenty L-1 stage larvae of *Haemonchus* nematode were released and allowed to stand for 4 days, and subsequently the motility ability thereof was investigated. The motility impediment rate of each treatment plot was corrected and calculated based on the impediment efficacy by a DMSO solution alone, and evaluated according to the criteria shown below.

Criteria:
A: the corrected motility impediment rate is 100%
B: the corrected motility impediment rate is 99% to 90%
C: the corrected motility impediment rate is 89% to 80%
D: the corrected motility impediment rate is 79% to 50%

As a result, the compounds 1-13, 1-17, 1-28, 2-2, 2-4, 2-8, 2-14, and 2-34 of the present invention showed the activity level evaluated as A.

Test Example 6

Impact Evaluation Test on Larvae Motility of Dog Heartworm (*Dirofilaria immitis*)

Five hundred L-1 stage larvae of dog heartworm diluted in a predetermined prepared solution were inoculated in each well of a 96-well plate, a DMSO dilute solution of the benzimidazole compound represented by the general formula (1) of the present invention or a salt thereof was added to give a final concentration of 50 ppm. Then, the larvae were allowed to stand for 3 days and the mobility ability thereof was investigated. The motility impediment rate of each treatment plot was corrected and calculated based on the impediment efficacy by a DMSO solution alone, and the impact efficacy was evaluated according to the criteria shown below.

Criteria

A: the corrected motility impediment rate is 100%
B: the corrected motility impediment rate is 99% to 90%
C: the corrected motility impediment rate is 89% to 80%
D: the corrected motility impediment rate is 79% to 50%

As a result, the compounds 1-13, 1-17, 1-28, 2-2, 2-4, 2-8, 2-14, and 2-34 of the present invention showed the activity level evaluated as A.

INDUSTRIAL APPLICABILITY

The compound of the present invention is highly effective for the control of a wide range of agricultural and horticultural pests and mites and thus is useful.

The invention claimed is:

1. A benzimidazole compound represented by a general formula (1)

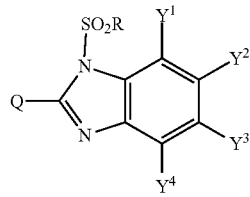

wherein R is
a $(C_1-C_6)$ alkyl group;
a $(C_3-C_6)$ cycloalkyl group;
a $(C_3-C_6)$ cycloalkyl $(C_1-C_6)$ alkyl group;
a halo $(C_1-C_6)$ alkyl group;
a $(C_2-C_6)$ alkenyl group; or
a $(C_2-C_6)$ alkynyl group,
$Y^1$, $Y^2$, $Y^3$ and $Y^4$, the same or different, are
a hydrogen atom;
a halogen atom;
a $(C_1-C_6)$ alkyl group; or
a halo $(C_1-C_6)$ alkyl group,
Q is selected from the following nitrogen-containing 5-membered heterocyclic groups, wherein $X^1$ and $X^4$, the same or different, are
a hydrogen atom; or
a $(C_1-C_6)$ alkyl group,
$X^2$ is
a hydrogen atom;
a halogen atom;
a cyano group;
a $(C_1-C_{12})$ alkyl group;
a $(C_3-C_6)$ cycloalkyl group;
a $(C_2-C_{12})$ alkenyl group;
a $(C_2-C_{12})$ alkynyl group;
a $(C_1-C_6)$ alkoxy group;
a halo $(C_1-C_6)$ alkyl group;
a halo $(C_1-C_6)$ alkoxy group;

a $(C_1-C_6)$ alkylthio group;
a $(C_1-C_6)$ alkylsulfinyl group;
a $(C_1-C_6)$ alkylsulfonyl group;
a halo $(C_1-C_6)$ alkylthio group;
a halo $(C_1-C_6)$ alkylsulfinyl group;
a halo $(C_1-C_6)$ alkylsulfonyl group;
a halo $(C_1-C_6)$ alkoxy $(C_1-C_6)$ alkyl group;
a $(C_3-C_6)$ cycloalkyl $(C_2-C_6)$ alkynyl group;
a $(C_1-C_6)$ alkylcarbonyl group;
a $(C_1-C_6)$ alkoxycarbonyl group;
a $(C_2-C_6)$ alkynyloxycarbonyl group;
a $(C_1-C_6)$ alkylthiocarbonyl group;
a $(C_1-C_6)$ alkoxycarbonyl $(C_1-C_6)$ alkyl group;
a $(C_1-C_6)$ alkoxycarbonyl $(C_2-C_6)$ alkenyl group;
an aryloxy $(C_1-C_6)$ alkyl group;
an aryloxy $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryloxycarbonyl group;
an aryloxycarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an arylcarbonyl group;
an arylcarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryl $(C_1-C_6)$ alkyl group;
an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryl $(C_1-C_6)$ alkoxycarbonyl group;
an aryl $(C_1-C_6)$ alkoxycarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryl $(C_2-C_6)$ alkynyl group;
an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $R^1R^2N$ group, wherein $R^1$ and $R^2$, the same or different, are (aa) a hydrogen atom, (ab) a $(C_1-C_6)$ alkyl group, (ac) a $(C_1-C_6)$ alkoxy group, (ad) a $(C_1-C_6)$ alkoxycarbonyl group, (ae) a $(C_1-C_6)$ alkylsulfonyl group, (af) a halo $(C_1-C_6)$ alkylsulfonyl group, (ag) an aryl group, (ah) a $(C_3-C_6)$ cycloalkyl group, (ai) a halo $(C_1-C_6)$ alkyl group, or (aj) an aryl $(C_1-C_6)$ alkyl group;
a $R^1R^2N$ carbonyl group, wherein $R^1$ and $R^2$ have the same meaning as above;
a $R^1R^2N$ sulfonyl group, wherein $R^1$ and $R^2$ have the same meaning as above;
a halo $(C_1-C_6)$ alkoxycarbonyl group;
a halo $(C_1-C_6)$ alkoxycarbonyl $(C_2-C_6)$ alkenyl group;
an aryl $(C_1-C_6)$ alkoxycarbonyl $(C_2-C_6)$ alkenyl group;
an aryl $(C_1-C_6)$ alkoxycarbonyl $(C_2-C_6)$ alkenyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $(C_3-C_{12})$ cycloalkyl $(C_1-C_6)$ alkoxycarbonyl $(C_2-C_6)$ alkenyl group;
a heteroaryl $(C_2-C_6)$ alkynyl group;
a heteroaryl $(C_2-C_6)$ alkynyl group having the same or different one to four substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $(C_3-C_6)$ cycloalkyl $(C_1-C_6)$ alkyl group;
a $(C_1-C_6)$ alkoxy $(C_2-C_6)$ alkynyl group;
a $(C_1-C_6)$ alkoxy $(C_1-C_6)$ alkyl group;
a $(C_1-C_6)$ alkylcarbonyloxy $(C_2-C_6)$ alkynyl group;
a $(C_1-C_6)$ alkylcarbonyloxy $(C_1-C_6)$ alkyl group;
a halo $(C_1-C_6)$ alkoxy $(C_2-C_6)$ alkynyl group;
an aryloxy $(C_2-C_6)$ alkynyl group;
an aryloxy $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a 1-$(C_1-C_6)$ alkoxyimino $(C_1-C_6)$ alkyl group;
a $(C_1-C_6)$ alkylaminocarbonyl $(C_2-C_6)$ alkenyl group;
a halo $(C_1-C_6)$ alkylaminocarbonyl $(C_2-C_6)$ alkenyl group;
an aryl $(C_1-C_6)$ alkylthio group; or an aryl $(C_1-C_6)$ alkylthio group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group, $X^3$ is a hydrogen atom;

a halogen atom;

a ($C_1$-$C_6$) alkyl group;

a halo ($C_1$-$C_6$) alkyl group;

a ($C_1$-$C_6$) alkoxy group;

a halo ($C_1$-$C_6$) alkoxy group;

a ($C_1$-$C_6$) alkoxycarbonyl ($C_2$-$C_6$) alkenyl group;

a ($C_1$-$C_6$) alkylthio group;

a ($C_1$-$C_6$) alkoxycarbonyl ($C_1$-$C_6$) alkoxy group;

a ($C_1$-$C_6$) alkoxycarbonyl group;

a ($C_2$-$C_6$) alkynyloxycarbonyl group;

an aryl ($C_1$-$C_6$) alkyl group;

an aryl ($C_1$-$C_6$) alkyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

an arylsulfonyl group;

an arylsulfonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

an aryloxycarbonyl group;

an aryloxycarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

an aryl ($C_1$-$C_6$) alkoxycarbonyl group;

an aryl ($C_1$-$C_6$) alkoxycarbonyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

an aryl ($C_1$-$C_6$) alkoxy group;

an aryl ($C_1$-$C_6$) alkoxy group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

a ($C_3$-$C_6$) cycloalkyl group;

a ($C_3$-$C_6$) cycloalkyl ($C_2$-$C_6$) alkenyl group;

a ($C_3$-$C_6$) cycloalkyl ($C_1$-$C_6$) alkyl group;

a ($C_2$-$C_6$) alkenyl group;

an aryl ($C_2$-$C_6$) alkynyl group;

an aryl ($C_2$-$C_6$) alkynyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

a ($C_1$-$C_6$) alkoxy ($C_1$-$C_6$) alkyl group;

a ($C_2$-$C_6$) alkynyloxy group;

a cyano group;

a ($C_2$-$C_6$) alkynyl group;

a ($C_1$-$C_6$) alkoxycarbonyl ($C_1$-$C_6$) alkyl group;

a ($C_1$-$C_6$) alkoxy ($C_2$-$C_6$) alkynyl group;

a halo ($C_1$-$C_6$) alkoxy ($C_2$-$C_6$) alkynyl group;

a $R^1R^2N$ carbonyl group, wherein $R^1$ and $R^2$ have the same meaning as above;

a $R^1R^2N$ carbonyl ($C_1$-$C_6$) alkoxy group, wherein $R^1$ and $R^2$ have the same meaning as above;

a $R^1R^2N$ carbonyl halo ($C_1$-$C_6$) alkoxy group, wherein $R^1$ and $R^2$ have the same meaning as above; or $X^2$ and $X^3$ may be combined to form a 5- to 8-membered aliphatic ring together with the carbon atoms to which they are bound, and the aliphatic ring may have one to five substituents selected from a ($C_1$-$C_6$) alkyl group and an oxo group, wherein the moiety at which the • mark is shown binds to benzimidazole;

or a salt thereof.

2. The benzimidazole compound according to claim 1, wherein

R is a ($C_1$-$C_6$) alkyl group; or a halo ($C_1$-$C_6$) alkyl group, $Y^1$, $Y^2$, $Y^3$ and $Y^4$, the same or different, are a hydrogen atom;

a halogen atom;

a ($C_1$-$C_6$) alkyl group; or a halo ($C_1$-$C_6$) alkyl group, $X^1$ and $X^4$, the same or different, are a hydrogen atom; or a ($C_1$-$C_6$) alkyl group, $X^2$ is a hydrogen atom;

a halogen atom;

a cyano group;

a ($C_1$-$C_{12}$) alkyl group;

a ($C_3$-$C_6$) cycloalkyl group;

a ($C_2$-$C_{12}$) alkenyl group;

a ($C_2$-$C_{12}$) alkynyl group;

a halo ($C_1$-$C_6$) alkyl group;

a ($C_1$-$C_6$) alkylthio group;

a ($C_1$-$C_6$) alkylsulfinyl group;

a ($C_1$-$C_6$) alkylsulfonyl group;

a halo ($C_1$-$C_6$) alkylthio group;

a halo ($C_1$-$C_6$) alkoxy ($C_1$-$C_6$) alkyl group;

a ($C_3$-$C_6$) cycloalkyl ($C_2$-$C_6$) alkynyl group;

a ($C_1$-$C_6$) alkylcarbonyl group;

a ($C_1$-$C_6$) alkoxycarbonyl group;

a ($C_2$-$C_6$) alkynyloxycarbonyl group;

a ($C_1$-$C_6$) alkylthiocarbonyl group;

a ($C_1$-$C_6$) alkoxycarbonyl ($C_1$-$C_6$) alkyl group;

a $(C_1-C_6)$ alkoxycarbonyl $(C_2-C_6)$ alkenyl group;
an aryloxy $(C_1-C_6)$ alkyl group;
an aryloxy $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryloxycarbonyl group;
an aryloxycarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an arylcarbonyl group;
an arylcarbonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryl $(C_1-C_6)$ alkyl group;
an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an aryl $(C_2-C_6)$ alkynyl group;
an aryl $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $R^1R^2N$ carbonyl group, wherein $R^1$ and $R^2$ have the same meaning as above;
a $R^1R^2N$ sulfonyl group, wherein $R^1$ and $R^2$ have the same meaning as above;
a halo $(C_1-C_6)$ alkoxycarbonyl group;
a halo $(C_1-C_6)$ alkoxycarbonyl $(C_2-C_6)$ alkenyl group;
an aryl $(C_1-C_6)$ alkoxycarbonyl $(C_2-C_6)$ alkenyl group;
an aryl $(C_1-C_6)$ alkoxycarbonyl $(C_2-C_6)$ alkenyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $(C_3-C_{12})$ cycloalkyl $(C_1-C_6)$ alkoxycarbonyl $(C_2-C_6)$ alkenyl group;
a heteroaryl $(C_2-C_6)$ alkynyl group;
a heteroaryl $(C_2-C_6)$ alkynyl group having the same or different one to four substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $(C_3-C_6)$ cycloalkyl $(C_1-C_6)$ alkyl group;
a $(C_1-C_6)$ alkoxy $(C_2-C_6)$ alkynyl group;
a $(C_1-C_6)$ alkoxy $(C_1-C_6)$ alkyl group;
a $(C_1-C_6)$ alkylcarbonyloxy $(C_2-C_6)$ alkynyl group;
a $(C_1-C_6)$ alkylcarbonyloxy $(C_1-C_6)$ alkyl group;
a halo $(C_1-C_6)$ alkoxy $(C_2-C_6)$ alkynyl group;
an aryloxy $(C_2-C_6)$ alkynyl group;
an aryloxy $(C_2-C_6)$ alkynyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
a $(C_1-C_6)$ alkylaminocarbonyl $(C_2-C_6)$ alkenyl group;
a halo $(C_1-C_6)$ alkylaminocarbonyl $(C_2-C_6)$ alkenyl group;
an aryl $(C_1-C_6)$ alkylthio group; or
an aryl $(C_1-C_6)$ alkylthio group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group,
$X^3$ is
a hydrogen atom;
a halogen atom;
a $(C_1-C_6)$ alkyl group;
a halo $(C_1-C_6)$ alkyl group;
a $(C_1-C_6)$ alkoxy group;
a halo $(C_1-C_6)$ alkoxy group;
a $(C_1-C_6)$ alkoxycarbonyl $(C_2-C_6)$ alkenyl group;
a $(C_1-C_6)$ alkylthio group;
a $(C_1-C_6)$ alkoxycarbonyl $(C_1-C_6)$ alkoxy group;
a $(C_1-C_6)$ alkoxycarbonyl group;
an aryl $(C_1-C_6)$ alkyl group;
an aryl $(C_1-C_6)$ alkyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a $(C_1-C_6)$ alkylthio group, (g) a halo $(C_1-C_6)$ alkylthio group, (h) a $(C_1-C_6)$ alkylsulfinyl group, (i) a halo $(C_1-C_6)$ alkylsulfinyl group, (j) a $(C_1-C_6)$ alkylsulfonyl group, and (k) a halo $(C_1-C_6)$ alkylsulfonyl group;
an arylsulfonyl group;
an arylsulfonyl group having the same or different one to five substituents selected from (a) a halogen atom, (b) a $(C_1-C_6)$ alkyl group, (c) a halo $(C_1-C_6)$ alkyl group, (d) a $(C_1-C_6)$ alkoxy group, (e) a halo $(C_1-C_6)$ alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

an aryl ($C_1$-$C_6$) alkoxy group;

an aryl ($C_1$-$C_6$) alkoxy group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

a ($C_3$-$C_6$) cycloalkyl group;

a ($C_3$-$C_6$) cycloalkyl ($C_2$-$C_6$) alkenyl group;

a ($C_3$-$C_6$) cycloalkyl ($C_1$-$C_6$) alkyl group;

a ($C_2$-$C_6$) alkenyl group;

an aryl ($C_2$-$C_6$) alkynyl group;

an aryl ($C_2$-$C_6$) alkynyl group having the same or different one to five substituents selected from (a) a halogen atom, (b) a ($C_1$-$C_6$) alkyl group, (c) a halo ($C_1$-$C_6$) alkyl group, (d) a ($C_1$-$C_6$) alkoxy group, (e) a halo ($C_1$-$C_6$) alkoxy group, (f) a ($C_1$-$C_6$) alkylthio group, (g) a halo ($C_1$-$C_6$) alkylthio group, (h) a ($C_1$-$C_6$) alkylsulfinyl group, (i) a halo ($C_1$-$C_6$) alkylsulfinyl group, (j) a ($C_1$-$C_6$) alkylsulfonyl group, and (k) a halo ($C_1$-$C_6$) alkylsulfonyl group;

a ($C_1$-$C_6$) alkoxy ($C_1$-$C_6$) alkyl group;

a ($C_2$-$C_6$) alkynyloxy group;

a cyano group;

a ($C_2$-$C_6$) alkynyl group;

a ($C_1$-$C_6$) alkoxycarbonyl ($C_1$-$C_6$) alkyl group;

a ($C_1$-$C_6$) alkoxy ($C_2$-$C_6$) alkynyl group;

a halo ($C_1$-$C_6$) alkoxy ($C_2$-$C_6$) alkynyl group;

a $R^1R^2N$ carbonyl group, wherein $R^1$ and $R^2$ have the same meaning as above;

a $R^1R^2N$ carbonyl ($C_1$-$C_6$) alkoxy group, wherein $R^1$ and $R^2$ have the same meaning as above;

a $R^1R^2N$ carbonyl halo ($C_1$-$C_6$) alkoxy group, wherein $R^1$ and $R^2$ have the same meaning as above; or $X^2$ and $X^3$ may be combined to form a 5- to 8-membered aliphatic ring together with the carbon atoms to which they are bound, and the aliphatic ring may have one to five substituents selected from a ($C_1$-$C_6$) alkyl group and an oxo group;

or a salt thereof.

3. The benzimidazole compound or a salt thereof according to claim 1, wherein Q is Q-2, Q-3, or Q-4.

4. An agricultural and horticultural insecticidal and acaricidal agent, comprising the benzimidazole compound or a salt thereof according to claim 1 as an active ingredient.

5. A method for using an agricultural and horticultural insecticidal and acaricidal agent, comprising applying an effective amount of the benzimidazole compound or a salt thereof according to claim 1 to plants or soil.

6. An ectoparasite control agent for animals, comprising the benzimidazole compound or a salt thereof according to claim 1 as an active ingredient.

7. An endoparasite control agent for animals, comprising the benzimidazole compound or a salt thereof according to claim 1 as an active ingredient.

8. A method for controlling ectoparasites, comprising orally or parenterally administering, to an animal in need thereof, an effective amount of the benzimidazole compound or a salt thereof according to claim 1 as an active ingredient.

9. A method for controlling endoparasites, comprising orally or parenterally administering, to an animal in need thereof, an effective amount of the benzimidazole compound or a salt thereof according to claim 1 as an active ingredient.

* * * * *